US012746391B2

(12) United States Patent
Sharma et al.

(10) Patent No.: US 12,746,391 B2
(45) Date of Patent: Sep. 29, 2026

(54) SYSTEMS FOR CLOSED-LOOP ULTRASOUND-IMAGING BASED CONTROL AND RELATED METHODS

(71) Applicant: NORTH CAROLINA STATE UNIVERSITY, Raleigh, NC (US)

(72) Inventors: Nitin Sharma, Raleigh, NC (US); Qiang Zhang, Raleigh, NC (US); Albert Dodson, Raleigh, NC (US); Ashwin Iyer, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 1028 days.

(21) Appl. No.: 17/937,946

(22) Filed: Oct. 4, 2022

(65) Prior Publication Data

US 2023/0116271 A1 Apr. 13, 2023

Related U.S. Application Data

(60) Provisional application No. 63/251,878, filed on Oct. 4, 2021.

(51) Int. Cl.

| | |
|---|---|
| ***A61H 3/00*** | (2006.01) |
| ***A61H 1/02*** | (2006.01) |
| ***A61N 1/36*** | (2006.01) |

(52) U.S. Cl.

CPC ....... *A61N 1/36031* (2017.08); *A61H 1/0266* (2013.01); *A61H 3/00* (2013.01);

(Continued)

(58) Field of Classification Search

CPC ...... A61H 1/0237; A61H 1/0266; A61H 3/00; A61H 2201/5005; A61H 2201/5058;

(Continued)

(56) References Cited

U.S. PATENT DOCUMENTS

| | | | |
|---|---|---|---|
| 9,107,614 | B2 | 8/2015 | Halkias et al. |
| 9,389,733 | B2 | 7/2016 | Kristensson et al. |

(Continued)

FOREIGN PATENT DOCUMENTS

| | | | |
|---|---|---|---|
| WO | 2005011494 | 2/2005 | |
| WO | WO-2017120484 A1 * | 7/2017 | ......... A61N 1/36003 |

OTHER PUBLICATIONS

Aagaard, J. L. Andersen, P. Dyhre-Poulsen, A.-M. Leffers, A. Wag-ner, S. P. Magnusson, J. Halkjær-Kristensen, and E. B. Simonsen, "A mechanism for increased contractile strength of human pennate muscle in response to strength training: changes in muscle architecture," J. Physiol., vol. 534, No. 2, pp. 613-623, 2001.

(Continued)

*Primary Examiner* — Bradley H Philips
*Assistant Examiner* — Tyler A Raubenstraw
(74) *Attorney, Agent, or Firm* — Meunier Carlin & Curfman LLC

(57) ABSTRACT

Systems and methods for closed-loop ultrasound imaging-based control are described herein. An example system includes an ultrasound transducer, and a controller operably coupled to the ultrasound transducer. The controller includes a processor and memory, the memory having computer executable instructions stored thereon. The controller is configured to receive an ultrasound imaging signal associated with a subject's muscular activity from the ultrasound transducer; process the ultrasound imaging signal to obtain a feedback signal; and control a device interfacing with the subject based on the feedback signal.

40 Claims, 49 Drawing Sheets

(52) U.S. Cl.
CPC .. *A61N 1/36003* (2013.01); *A61H 2201/5005* (2013.01); *A61H 2201/5058* (2013.01); *A61H 2201/5061* (2013.01); *A61H 2201/5069* (2013.01); *A61H 2201/5084* (2013.01); *A61H 2205/12* (2013.01); *A61H 2230/085* (2013.01); *A61H 2230/605* (2013.01)

(58) Field of Classification Search
CPC .... A61H 2201/5084; A61H 2201/5069; A61H 2201/5061; A61H 2205/12; A61H 2230/085; A61H 2230/605; A61H 2230/60; A61N 1/36003; A61N 1/36; A61N 1/36067; A61N 1/36031; B25J 9/0006
See application file for complete search history.

(56) References Cited

U.S. PATENT DOCUMENTS

| | | | | |
|---|---|---|---|---|
| 10,363,413 | B2 | 7/2019 | Nagel et al. | |
| 10,625,074 | B2 | 4/2020 | Rosenbluth et al. | |
| 11,148,279 | B1 * | 10/2021 | Mooney | A61H 1/0266 |
| 11,596,785 | B2 * | 3/2023 | Hamner | A61N 1/36031 |
| 11,853,034 | B2 * | 12/2023 | Zealand | G06F 3/01 |
| 2002/0161415 | A1 * | 10/2002 | Cohen | A61N 1/36003 607/48 |
| 2012/0109020 | A1 * | 5/2012 | Wagner | A61N 7/00 607/45 |
| 2015/0360039 | A1 * | 12/2015 | Lempka | A61N 1/37264 607/59 |
| 2017/0065249 | A1 * | 3/2017 | Egorov | A61B 5/227 |
| 2017/0123487 | A1 * | 5/2017 | Hazra | G06F 3/0482 |
| 2017/0156662 | A1 * | 6/2017 | Goodall | A61N 2/002 |
| 2018/0193649 | A1 * | 7/2018 | Schouenborg | A61N 1/36132 |
| 2018/0207450 | A1 * | 7/2018 | Sanchez | A61N 7/00 |
| 2019/0001121 | A1 * | 1/2019 | Lara | A61N 1/36082 |
| 2019/0183724 | A1 * | 6/2019 | Sifferlin | A61H 1/00 |
| 2019/0209431 | A1 * | 7/2019 | Warlick | A61H 39/007 |
| 2019/0247650 | A1 * | 8/2019 | Tran | A61N 1/3704 |
| 2019/0269914 | A1 * | 9/2019 | Moaddeb | A61N 1/36031 |
| 2019/0283247 | A1 * | 9/2019 | Chang | A61B 5/1121 |
| 2019/0357810 | A1 * | 11/2019 | Spoof | A61B 5/1106 |
| 2020/0009371 | A1 * | 1/2020 | Langer | A61N 1/36007 |
| 2020/0230408 | A1 * | 7/2020 | Errico | A61N 1/36014 |
| 2020/0230413 | A1 * | 7/2020 | Madhavan | A61B 5/0042 |
| 2020/0376266 | A1 * | 12/2020 | Toong | A61N 1/36007 |
| 2020/0405188 | A1 * | 12/2020 | Sharma | A61N 1/36031 |
| 2021/0121355 | A1 * | 4/2021 | Behboodi | B25J 9/0006 |
| 2021/0267834 | A1 * | 9/2021 | Lerner | A61H 1/0237 |
| 2021/0291355 | A1 * | 9/2021 | Lerner | B25J 9/0006 |
| 2021/0370063 | A1 * | 12/2021 | Abouelsoud | A61N 1/36025 |

OTHER PUBLICATIONS

Ahmed-Ali, T., Van Assche, V., Massieu, J.-F., and Dorleans, P., 2013. "Continuous-Discrete Observer for State Affine Systems With Sampled and Delayed Measurements". IEEE Trans. Automat. Contr., 58(4), pp. 1085-1091.

Alexander, Harold L. "State estimation for distributed systems with sensing delay." Data Structures and Target Classification. vol. 1470. SPIE, 1991.

Alibeji, et al., "A modified dynamic surface controller for delayed neuromuscular electrical stimulation," IEEE/ASME Transactions on Mechatronics, vol. 22, No. 4, pp. 1755-1764, Aug. 2017.

Alibeji, N. A., Molazadeh, V., Dicianno, B. E., and Sharma, N., 2018. "A control scheme that uses dynamic postural synergies to coordinate a hybrid walking neuroprosthesis: Theory and experiments". Front. Neurosci., 12, p. 159.

Alibeji, N. A., Molazadeh, V., Moore-Clingenpeel, F., and Sharma, N., 2018. "A muscle synergy-inspired control design to coordinate functional electrical stimulation and a powered exoskeleton: Artificial generation of synergies to reduce input dimensionality". IEEE Cont. Syst. Mag., 38(6), pp. 35-60.

Alibeji, N., Kirsch, N., and Sharma, N., 2015. "Dynamic surface control of neuromuscular electrical stimulation of a musculoskeletal system with activation dynamics and an input delay". In Proc. of ACC, IEEE, pp. 631-636.

Alibeji, N., Kirsch, N., Farrokhi, S., and Sharma, N., 2015. "Further results on predictor-based control of neuromuscular electrical stimulation". IEEE Trans. Neural Syst. Rehabil. Eng., 23(6), pp. 1095-1105.

Ambrosini, E.; Ferrante, S.; Schauer, T.; Klauer, C.; Gaffuri, M.; Ferrigno, G.; Pedrocchi, A. A myocontrolled neuroprosthesis integrated with a passive exoskeleton to support upper limb activities. J. Electromyogr. Kinesiol. 2014, 24, 307-317.

Ao, et al, "Movement Performance of Human-Robot Cooperation Control Based on EMG-Driven Hill-Type and Proportional Models for an Ankle Power-Assist Exoskeleton Robot," IEEE Trans. Neural Syst. Rehabil. Eng., vol. 25, No. 8, pp. 1125-1134, 2017.

Asbeck, S. M. De Rossi, K. G. Holt, and C. J. Walsh, "A biologically inspired soft exosuit for walking assistance," Int. J. Rob. Res., vol. 34, No. 6, pp. 744-762, 2015.

Asl, T. Narikiyo, and M. Kawanishi, "Adaptive neural network-based saturated control of robotic exoskeletons," Nonlinear Dyn., vol. 94, No. 1, pp. 123-139, 2018.

Banala, S. H. Kim, S. K. Agrawal, and J. P. Scholz, "Robot assisted gait training with active leg exoskeleton (ALEX)," IEEE Trans. Neural Syst. Rehabil. Eng., vol. 17, No. 1, pp. 2-8, 2009.

Baud, A. R. Manzoori, A. Ijspeert, and M. Bouri, "Review of control strategies for lower-limb exoskeletons to assist gait," J. Neuroeng. Rehabil., vol. 18, No. 1, pp. 1-34, 2021.

Begovic, G -Q. Zhou, T. Li, Y. Wang, and Y.-P. Zheng, "Detection of the electromechanical delay and its components during voluntary isometric contraction of the quadriceps femoris muscle," Front. Phys-iol., vol. 5, p. 494, 2014.

Bhatia, P. Bain, N. Bajaj, R. J. Elble, M. Hallett, E. D. Louis, J. Raethjen, M. Stamelou, C. M. Testa, G. Deuschl et al., "Consensus statement on the classification of tremors. from the task force on tremor of the international parkinson and movement disorder society," Movement Disorders, vol. 33, No. 1, pp. 75-87, 2018.

Blackburn, D. R. Bell, M. F. Norcross, J. D. Hudson, and L. A. Engstrom, "Comparison of hamstring neuromechanical properties between healthy males and females and the influence of musculotendinous stiffness," J. Electromyogr. Kinesiol., vol. 19, No. 5, pp. e362-e369, 2009.

Blaya, J., and Herr, H., 2004. "Adaptive Control of a Variable-Impedance Ankle-Foot Orthosis to Assist Drop-Foot Gait". IEEE Trans. Neural Syst. Rehabil. Eng., 12(1), mar, pp. 24-31.

Bryan, et al., "A hip-knee-ankle exoskeleton emulator for studying gait assistance," Int. J. Robot. Res., vol. 40, No. 4-5, pp. 722-746, 2021.

Buchanan, D. G. Lloyd, K. Manal, and T. F. Besier, "Neuromusculoskeletal Modeling: Estimation of Muscle Forces and Joint Moments and Movements from Measurements of Neural Command," J. Appl. Biomech., vol. 20, No. 4, pp. 367-395, 2004.

Burne, M. Hayes, V. Fung, C. Yiannikas, and D. Boljevac, "The contribution of tremor studies to diagnosis of parkinsonian and essential tremor: a statistical evaluation," Journal of Clinical Neuroscience, vol. 9, No. 3, pp. 237-242, 2002.

Cavanagh, P. R., and Komi, P. V., 1979. "Electromechanical delay in human skeletal muscle under concentric and eccentric contractions.". Eur. J. Appl. Physiol. Occup. Physiol., 42(3), pp. 159-163.

Cifrek, M.; Medved, V.; Tonkovic0, S .; Ostojic0, S. Surface EMG based muscle fatigue evaluation in biomechanics. Clin. Biomech. 2009, 24, 327-340.

Cornwall, M. W., and Mcpoil, T. G., 1994. "The Influence of Tibialis Anterior Muscle Activity on Rearfoot Motion during Walking". Foot Ankle Int., 15(2), pp. 75-79.

Crouch, D.L.; Pan, L.; Filer, W.; Stallings, J.W.; Huang, H. Comparing Surface and Intramuscular Electromyography for Simultaneous and Proportional Control Based on a Musculoskeletal Model: A Pilot Study. IEEE Trans. Neural Syst. Rehabil. Eng. 2018, 26, 1735-1744. doi: 10.1109/TNSRE.2018.2859833.

(56) References Cited

OTHER PUBLICATIONS

Cunningham, P. J. Harding, and I. D. Loram, "The application of deep convolutional neural networks to ultrasound for modelling of dynamic states within human skeletal muscle," arXiv preprint arXiv:1706.09450, 2017.
Daubney, M. E., and Culham, E. G., 1999. "Lower-Extremity Muscle Force and Balance Performance in Adults Aged 65 Years and Older". Phys. Ther., 79(12), pp. 1177-1185.
Dawson, M.J.; Gadian, D.; Wilkie, D. Muscular fatigue investigated by phosphorus nuclear magnetic resonance. Nature 1978, 274, 861-866.
De Oliveira and L. Luporini Menegaldo, "Individual-specific muscle maximum force estimation using ultrasound for ankle joint torque prediction using an EMG-driven Hill-type model," J. Biomech., vol. 43, No. 14, pp. 2816-2821, 2010.
Del-Ama, A. Gil-Agudo, J. L. Pons, and J. C. Moreno, "Hy-brid FES-robot cooperative control of ambulatory gait rehabilitation exoskeleton," J. Neuroeng. Rehabil., vol. 11, No. 1, p. 27, 2014.
Delp, F. C. Anderson, A. S. Arnold, P. Loan, A. Habib, C. T. John, E. Guendelman, and D. G. Thelen, "Opensim: open-source software to create and analyze dynamic simulations of movement," IEEE Trans. Biomed. Eng., vol. 54, No. 11, pp. 1940-1950, 2007.
Delp, Surgery simulation: a computer graphics system to analyze and design musculoskeletal reconstructions of the lower limb. Stanford University, 1990.
Deuschl, P. Bain, M. Brin, and A. H. S. Committee, "Consensus statement of the movement disorder society on tremor," Movement Disorders, vol. 13, No. S3, pp. 2-23, 1998.
Dick, A. A. Biewener, and J. M. Wakeling, "Comparison of human gastrocnemius forces predicted by Hill-type muscle models and estimated from ultrasound images," J. Exp. Biol., vol. 220, No. 9, pp. 1643-1653, 2017.
Ding, et al., "Human-in-the-loop optimization of hip assistance with a soft exosuit during walking," Sci. Robot., vol. 3, No. 15, 2018.
Downey, R. J., Merad, M., Gonzalez, E. J., and Dixon, W. E., 2016. "The time-varying nature of electromechanical delay and muscle control effectiveness in response to stimulation-induced fatigue". IEEE Trans. Neural Syst. Rehabil. Eng., 25(9), pp. 1397-1408.
Downey, R.J.; Bellman, M.J.; Kawai, H.; Gregory, C.M.; Dixon, W.E. Comparing the induced muscle fatigue between asynchronous and synchronous electrical stimulation in able-bodied and spinal cord injured populations. IEEE Trans. Neural Syst. Rehabil. Eng. 2014, 23, 964-972.
Downey, R.J.; Cheng, T.H.; Bellman, M.J.; Dixon, W.E. Closed-loop asynchronous neuromuscular electrical stimulation prolongs functional movements in the lower body. IEEE Trans. on Neural Syst. and Rehabil. Eng. 2015, 23, 1117-1127.
Du, H., Qian, C., and Li, S., 2013. "Global stabilization of a class of uncertain upper-triangular systems under sampleddata control". Int. J. Robust Nonlinear Control., 23(6), pp. 620-637.
Durandau, W. Rampeltshammer, H. van der Kooij, and M. Sartori, "Neuromechanical model-based control of bi-lateral ankle exoskeletons: biological joint torque and electromyogram reduction across walking conditions," arXiv preprint arXiv:2108.00980, 2021. IEEE Trans. Robot., vol. 38, No. 3, pp. 1380-1394, 2022.
Eilenberg, H. Geyer, and H. Herr, "Control of a powered ankle-foot prosthesis based on a neuromuscular model," IEEE Trans. Neural Syst. Rehabil. Eng., vol. 18, No. 2, pp. 164-173, 2010.
Everaert, D.G.; Thompson, A.K.; Su Ling Chong, S.L.; Stein, R.B. Does Functional Electrical Stimulation for Foot Drop Strengthen Corticospinal Connections? Neurorehabil. Neural Repair 2010, 24, 168-177. doi: 10.1177/1545968309349939.
Fang, N. Hettiarachchi, D. Zhou, and H. Liu, "Multi-modal sensing techniques for interfacing hand prostheses: A review," IEEE Sens. J., vol. 15, No. 11, pp. 6065-6076, 2015.
Fleischer and G. Hommel, "A human-exoskeleton interface utilizing electromyography," IEEE Trans. Robot., vol. 24, No. 4, pp. 872-882, 2008.
Fukunaga, T. E. T. S. U. O., et al. "Tendinous movement of a human muscle during voluntary contractions determined by real-time ultrasonography." Journal of Applied Physiology 81.3 (1996): 1430-1433.
Galle, et al., "Reducing the metabolic cost of walking with an ankle exoskeleton: interaction between actuation timing and power," J. Neuroeng. Rehabil., vol. 14, No. 1, pp. 1-16, 2017.
Gavin, H.P. The Levenberg-Marquardt algorithm for nonlinear least squares curve-fitting problems. Dept. Civil Environ. Eng., Duke Univ. 2019, pp. 1-19.
Gillijns and B. De Moor, "Unbiased minimum-variance input and state estimation for linear discrete-time systems with direct feedthrough," Automatica, vol. 43, No. 5, pp. 934-937, 2007.
Granat, M.H.; Maxwell, D.J.; Ferguson, A.C.; Lees, K.R.; Barbenet, J.C. Peroneal stimulator: Evaluation for the correction of spastic drop foot in hemiplegia. Arch. Phys. Med. Rehabil. 1996, 77, 19-24. doi: 10.1016/S0003-9993(96)90214-2.
Gregg, et al., "Virtual constraint control of a powered prosthetic leg: From simulation to experiments with transfemoral amputees," IEEE Trans. Robot., vol. 30, No. 6, pp. 1455-1471, 2014.
Grimaldi et al., "Neurological tremor: sensors, signal processing and emerging applications," Sensors, vol. 10, No. 2, pp. 1399-1422, 2010.
Gui, H. Liu, and D. Zhang, "A practical and adaptive method to achieve emg-based torque estimation for a robotic exoskeleton," IEEE/ASME Trans. Mechatron., vol. 24, No. 2, pp. 483-494, 2019.
Gui, U.-X. Tan, H. Liu, and D. Zhang, "Electromyography-driven progressive assist-as-needed control for lower limb exoskeleton," IEEE Trans. Med. Robot. Bionics., vol. 2, No. 1, pp. 50-58, 2020.
Guo, Y.-P. Zheng, H.-B. Xie, and X. Chen, "Continuous monitoring of electromyography (EMG), mechanomyography (MMG), sonomyography (SMG) and torque output during ramp and step isometric contractions," Med. Eng. Phys., vol. 32, No. 9, pp. 1032-1042, 2010.
Ha, S. A. Murray, and M. Goldfarb, "An approach for the cooperative control of fes with a powered exoskeleton during level walking for persons with paraplegia," IEEE Trans. Neural Syst. Rehabil. Eng., vol. 24, No. 4, pp. 455-466, 2016.
Hatze, "A myocybernetic control model of skeletal muscle," Biol. Cybern., vol. 25, No. 2, pp. 103-119, 1977.
Hill, "The heat of shortening and the dynamic constants of muscle," Philos. Trans. R. Soc. Lond., B, Biol. Sci., vol. 126, No. 843, pp. 136-195, 1938.
Hodges, L. Pengel, R. Herbert, and S. Gandevia, "Measurement of muscle contraction with ultrasound imaging," Muscle & Nerve, vol. 27, No. 6, pp. 682-692, 2003.
Hussain, P. K. Jamwal, M. H. Ghayesh, and S. Q. Xie, "Assistas-needed control of an intrinsically compliant robotic gait training orthosis," IEEE Trans. Ind. Electron., vol. 64, No. 2, pp. 1675-1685, 2016.
Ibitoye, M.O.; Estigoni, E.H.; Hamzaid, N.A.; Wahab, A.K.A.; Davis, G.M. The effectiveness of FES-evoked EMG potentials to assess muscle force and fatigue in individuals with spinal cord injury. Sensors 2014, 14, 12598-12622.
Ibitoye, M.O.; Hamzaid, N.A.; Zuniga, J.M.; Wahab, A.K.A. Mechanomyography and muscle function assessment: A review of current state and prospects. Clin. Biomech. 2014, 29, 691-704.
Iezzoni, L.I.; McCarthy, E.P.; Davis, R.B.; Siebens, H. Mobility difficulties are not only a problem of old age. J. Gen. Intern. Med. 2001, 16, 235-243.
Jackson and S. H. Collins, "Heuristic-based ankle exoskeleton control for co-adaptive assistance of human locomotion," IEEE Trans. Neural Syst. Rehabil. Eng., vol. 27, No. 10, pp. 2059-2069, 2019.
Jiménez-Fabián and O. Verlinden, "Review of control algorithms for robotic ankle systems in lower-limb orthoses, prostheses, and exoskeletons," Med. Eng. Phys., vol. 34, No. 4, pp. 397-408, 2012.
Karafyllis, I., and Krstic, M., 2011. "Nonlinear stabilization under sampled and delayed measurements, and with inputs subject to delay and zero-order hold". IEEE Trans. Autom. Control, 57(5), pp. 1141-1154.

(56) References Cited

OTHER PUBLICATIONS

Karafyllis, I., Malisoff, M., de Queiroz, M., Krstic, M., and Yang, R., 2015. "Predictor-based tracking for neuromuscular electrical stimulation". Int. J. Robust Nonlinear Control, 25(14), pp. 2391-2419.
Kawamoto and Y. Sankai, "Comfortable power assist control method for walking aid by hal-3," in IEEE International Conference on Systems, Man and Cybernetics, vol. 4, pp. 6-pp, IEEE, 2002.
Khazoom, et al., "Design and control of a multifunctional ankle exoskeleton powered by magnetorheological actuators to assist walking, jumping, and landing," IEEE Robot. Autom. Lett., vol. 4, No. 3, pp. 3083-3090, 2019.
Killeen, et al., "Minimum toe clearance:probing the neural control of locomotion," Sci. Rep., vol. 7, No. 1, pp. 1-10, 2017.
Kim and S. H. Collins, "Once-per-step control of ankle push-off work improves balance in a three-dimensional simulation of bipedal walking," IEEE Trans. Robot., vol. 33, No. 2, pp. 406-418, 2017.
Kim, et al., "Reducing the metabolic rate of walking and running with a versatile, portable exosuit," Science, vol. 365, No. 6454, pp. 668-672, 2019.
Kirsch, N.; Alibeji, N.; Sharma, N. Nonlinear model predictive control of functional electrical stimulation. Control Eng. Practice 2017, 58, 319-331.
Kirsch, X. Bao, N. Alibeji, B. Dicianno, and N. Sharma, "Modelbased dynamic control allocation in a hybrid neuroprosthesis," IEEE Trans. Neural Syst. Rehabil. Eng., vol. 26, No. 1, pp. 224-232, 2018.
Kluding, P.M.; Dunning, K.; O'Dell, M.W.; Wu, S.S.; Ginosian, J.; Feld, J.; McBride, K. Foot Drop Stimulation Versus Ankle Foot Orthosis After Stroke. Stroke 2013, 44, 1660-1669. doi: 10.1161/STROKEAHA.111.000334.
Kobravi and Erfanian, "Decentralized adaptive robust control based on sliding mode and nonlinear compensator for the control of ankle movement using functional electrical stimulation of agonist-antagonist muscles," J. Neural Eng., vol. 6, No. 4, p. 046007, 2009.
Koller, C. D. Remy, and D. P. Ferris, "Biomechanics and energetics of walking in powered ankle exoskeletons using myoelectric control versus mechanically intrinsic control," J. Neuroeng. Rehabil., vol. 15, No. 1, pp. 1-14, 2018.
Kottink, A.I.; Oostendorp, L.J.; Buurke, J.H.; Nene, A.V.; Hermens, H.J.; IJzerman, M.J. The Orthotic Effect of Functional Electrical Stimulation on the Improvement of Walking in Stroke Patients with a Dropped Foot: A Systematic Review. Artif. Organs 2004, 28, 577-586. doi:10.1111/j.1525-1594.2004.07310.x.
Lenzi, S. M. M. De Rossi, N. Vitiello, and M. C. Carrozza, "Intention-based emg control for powered exoskeletons," IEEE Trans. Biomed. Eng., vol. 59, No. 8, pp. 2180-2190, 2012.
Lerner, G. M. Gasparri, M. O. Bair, J. L. Lawson, J. Luque, T. A. Harvey, and A. T. Lerner, "An untethered ankle exoskeleton improves walking economy in a pilot study of individuals with cerebral palsy," IEEE Trans. Neural Syst. Rehabil. Eng., vol. 26, No. 10, pp. 1985-1993, 2018.
Li, Z. Huang, W. He, and C.-Y. Su, "Adaptive impedance control for an upper limb robotic exoskeleton using biological signals," IEEE Trans. Ind. Electron., vol. 64, No. 2, pp. 1664-1674, 2016.
Li, Z.; Guiraud, D.; Andreu, D.; Benoussaad, M.; Fattal, C.; Hayashibe, M. Real-time estimation of FES-induced joint torque with evoked EMG. J. Neuroeng. Rehabil. 2016, 13, 60.
Liberson, W.; Holmquest, H.; Scot, D.; Dow, M. Functional electrotherapy: stimulation of the peronea nerve synchronized with the swing phase of the gait of hemiplegic patients. Arch. Phys. Med., 1961, 42, 101-105.
Liu, Z. Wang, and X. Liu, "On global exponential stability of generalized stochastic neural networks with mixed time-delays," Neurocomputing, vol. 70, No. 1-3, pp. 314-326, 2006.
Lloyd and T. F. Besier, "An EMG-driven musculoskeletal model to estimate muscle forces and knee joint moments in vivo," J. Biomech., vol. 36, No. 6, pp. 765-776, 2003.
Lubinski, S. Y. Emelianov, and M. O'Donnell, "Speckle tracking methods for ultrasonic elasticity imaging using short-time correlation," IEEE transactions on ultrasonics.
Lyons, G.; Sinkjaer, T.; Burridge, J.; Wilcox, D. A review of portable FES-based neural orthoses for the correction of drop foot. IEEE Trans. Neur. Sys. and Rehab. Eng., 2002, 10, 260-279.
Mandrile, F.; Farina, D.; Pozzo, M.; Merletti, R. Stimulation artifact in surface EMG signal: effect of the stimulation waveform, detection system, and current amplitude using hybrid stimulation technique. IEEE Trans. Neural Sys. Rehabil. Eng. 2003, 11,407-415.
Marinakis and M. Marinaki, "A hybrid genetic-particle swarm optimization algorithm for the vehicle routing problem," Expert Syst. Appl., vol. 37, No. 2, pp. 1446-1455, 2010.
Matsumoto, M. Seki, T. Ando, Y. Kobayashi, H. Iijima, M. Nagaoka, and M. G. Fujie, "Analysis of emg signals of patients with essential tremor focusing on the change of tremor frequency," in 2012 Annual International Conference of the IEEE Engineering in Medicine and Biology Society. IEEE, 2012, pp. 2244-2250.
McCain, T. J. Dick, T. N. Giest, R. W. Nuckols, M. D. Lewek, K. R. Saul, and G. S. Sawicki, "Mechanics and energetics of poststroke walking aided by a powered ankle exoskeleton with speedadaptive myoelectric control," J. Neuroeng. Rehabil., vol. 16, No. 1, pp. 1-12, 2019.
Melo, P.; Silva, M.; Martins, J.; Newman, D. Technical developments of functional electrical stimulation to correct drop foot: sensing, actuation and control strategies. Clin. Biomech. 2015, 30, 101-113.
Miller, et al. "Depression symptoms in movement disorders: comparing parkinson's disease, dystonia, and essential tremor," Movement Disorders, vol. 22, No. 5, pp. 666-672, 2007.
Molazadeh, et al., "An Iteratively Learning Time-Invariant Controllerfor a Switched Cooperative Allocation Strategyduring Sit-to-Stand Task with a Hybrid Exoskeleton," IEEE Trans. Control Syst. Technol., IEEE Trans. Control Syst. Technol., vol. 30, No. 3, pp. 1021-1036, 2021. Accepted, 2021.
Nguyen, R.; Masani, K.; Micera, S.; Morari, M.; Popovic, M.R. Spatially distributed sequential stimulation reduces fatigue in paralyzed triceps surae muscles: a case study. Artif. Organs 2011, 35, 1174-1180.
Nuckols, et al. "Individualization of exosuit assistance based on measured muscle dynamics during versatile walking," Sci. Robot., vol. 6, No. 60, p. eabj1362, 2021.
Page, et al., "Point-to-point repetitive control of functional electrical stimulation for drop-foot," Control Eng. Pract., vol. 96, p. 104280, 2020.
Peternel, T. Noda, T. Petric0̌, A. Ude, J. Morimoto, and J. Babic0̌, "Adaptive control of exoskeleton robots for periodic assistive behaviours based on emg feedback minimisation," PloS one, vol. 11, No. 2, p. e0148942, 2016.
Pilkar, R.; Yarossi, M.; Ramanujam, A.; Rajagopalan, V.; Bayram, M.B.; Mitchell, M.; Canton, S.; Forrest, G. Application of empirical mode decomposition combined with notch filtering for interpretation of surface electromyograms during functional electrical stimulation. IEEE Trans. Neural Sys. Rehabil. Eng. 2016, 25, 1268-1277.
Popovi0́ c, D., Stein, R., O0guztöreli, M., Lebiedowska, M., and Joni0c, S., 1999. "Optimal control of walking with functional electrical stimulation: a computer simulation study". IEEE Trans. Rehabil. Eng., 7(1), pp. 69-79.
Praagman, M.; Veeger, H.; Chadwick, E.; Colier, W.; Van Der Helm, F. Muscle oxygen consumption, determined by NIRS, in relation to external force and Emg. J. Biomech. 2003, 36, 905-912.
Quinlivan, S. Lee, P. Malcolm, D. Rossi, M. Grimmer, C. Siviy, N. Karavas, D. Wagner, A. Asbeck, I. Galiana et al., "Assistance magnitude versus metabolic cost reductions for a tethered multiarticular soft exosuit," Sci. Robot., vol. 2, No. 2, p. eaah4416, 2017.
Rabe and N. P. Fey, "Evaluating electromyography and sonomyography sensor fusion to estimate lower-limb kinematics using gaussian process regression," Front. Robot. AI, vol. 9, 2022 https://doi.org/10.3389/frobt.2022.716545.
Rabe, T. Lenzi, and N. P. Fey, "Performance of sonomyographic and electromyographic sensing for continuous estimation of joint torque during ambulation on multiple terrains," IEEE Trans. Neural Syst. Rehabil. Eng., vol. 29, pp. 2635-2644, 2021.

(56) References Cited

OTHER PUBLICATIONS

Rajasekaran, et al., "Volition-adaptive control for gait training using wearable exoskeleton: preliminary tests with incomplete spinal cord injury individuals," J. Neuroeng. Rehabil., vol. 15, No. 1, pp. 1-15, 2018.
Riener and Fuhr, "Patient-driven control of FES-supported standing up: A simulation study," IEEE Trans. Rehabil. Eng., vol. 6, pp. 113-124, 1998.
Rigas, et al. "Assessment of tremor activity in the parkinsons disease using a set of wearable sensors," IEEE Transactions on Information Technology in Biomedicine, vol. 16, No. 3, pp. 478-487, 2012.
Rogers, D.R.; MacIsaac, D.T. EMG-based muscle fatigue assessment during dynamic contractions using principal component analysis. J. Electromyogr. Kinesiol. 2011, 21, 811-818.
Rouse, L. J. Hargrove, E. J. Perreault, and T. A. Kuiken, "Estimation of human ankle impedance during the stance phase of walking," IEEE Trans. Neural Sys. Rehabil. Eng., vol. 22, No. 4, pp. 870-878, 2014.
Sadoyama, T.; Miyano, H. Frequency analysis of surface EMG to evaluation of muscle fatigue. Eur. J. Appl. Physiol. Occupational Physiol. 1981, 47, 239-246.
Savitzky and M. J. Golay, "Smoothing and differentiation of data by simplified least squares procedures." Analytical chemistry, vol. 36, No. 8, pp. 1627-1639, 1964.
Sayenko, D.G.; Nguyen, R.; Hirabayashi, T.; Popovic, M.R.; Masani, K. Method to reduce muscle fatigue during transcutaneous neuromuscular electrical stimulation in major knee and ankle muscle groups. Neurorehabil. Neural Repair 2015, 29, 722-733.
Sayenko, D.G.; Nguyen, R.; Popovic, M.R.; Masani, K. Reducing muscle fatigue during transcutaneous neuromuscular electrical stimulation by spatially and sequentially distributing electrical stimulation sources. Eur. J. Appl. Physiol. 2014, 114, 793-804.
Scano, A.; Pirovano, I.; Manunza, M.; Spinelli, L.; Contini, D.; Torricelli, A.; Re, R. Sustained fatigue assessment during isometric exercises with time-domain near infrared spectroscopy and surface electromyography signals. Biomed. Opt. Express 2020, 11, 7357-7375.
Schauer, N. O. Negard, F. Previdi, K. J. Hunt, M. H. Fraser, E. Ferchland, and J. Raisch, "Online identification and nonlinear control of the electrically stimulated quadriceps muscle," Control Eng. Pract., vol. 13, pp. 1207-1219, 2005.
Seel, et al., "Iterative learning control of a drop foot neuroprosthesis-generating physiological foot motion in paretic gait by automatic feedback control," Control Eng. Pract., vol. 48, pp. 87-97, 2016.
Selfslagh, et al., "Non-invasive, brain-controlled functional electrical stimulation for locomotion rehabilitation in individuals with paraplegia," Sci. Rep., vol. 9, No. 1, pp. 1-17, 2019.
Seynnes, O.R.; Cronin, N.J. Simple Muscle Architecture Analysis (SMA): An ImageJ macro tool to automate measurements in B-mode ultrasound scans. Plos one 2020, 15, e0229034.
Sharma, C. Gregory, M. Johnson, and W. Dixon, "Closed-loop neural network-based NMES control for human limb tracking," IEEE Trans. Control Syst. Technol., vol. 20, No. 3, pp. 712-725, 2012.
Sharma, et al., "Nonlinear neuromuscular electrical stimulation tracking control of a human limb," IEEE Trans. Neural Syst. Rehabil. Eng., vol. 17, No. 6, pp. 576-584, 2009.
Sharma, N.; Kirsch, N.A.; Alibeji, N.A.; Dixon, W.E. A Non-Linear Control Method to Compensate for Muscle Fatigue during Neuromuscular Electrical Stimulation. Front. Robot. AI 2017, 4, 68. doi:10.3389/frobt.2017.00068.
Shen, Y., Zhang, D., and Xia, X., 2017. "Continuous observer design for a class of multi-output nonlinear systems with multi-rate sampled and delayed output measurements measurements". Automatica, 75, pp. 127-132.
Sheng, Z.; Sharma, N.; Kim, K. Quantitative Assessment of Changes in Muscle Contractility Due to Fatigue During NMES: An Ultrasound Imaging Approach. IEEE Trans. Biomed. Eng. 2019, 67, 832-841.
Sheng, Z.; Sharma, N.; Kim, K. Ultra-High-Frame-Rate Ultrasound Monitoring of Muscle Contractility Changes Due to Neuromuscular Electrical Stimulation. Ann. Biomed. Eng. 2021, pp. 1-14.
Sheng, Zhiyu, Nitin Sharma, and Kang Kim. "Ultra-high-frame-rate ultrasound monitoring of muscle contractility changes due to neuromuscular electrical stimulation." Annals of biomedical engineering 49 (2021): 262-275.
Shi, J.; Zheng, Y.P.; Chen, X.; Huang, Q.H. Assessment of muscle fatigue using sonomyography: muscle thickness change detected from ultrasound images. Med. Eng. Phys. 2007, 29, 472-479.
Shi, Y. P. Zheng, Q. H. Huang, and X. Chen, "Continuous monitoring of sonomyography, electromyography and torque generated by normal upper arm muscles during isometric contraction: Sonomyography assessment for arm muscles," IEEE Trans. Biomed. Eng., vol. 55, No. 3, pp. 1191-1198, 2008.
Sikdar, H. Rangwala, E. B. Eastlake, I. A. Hunt, A. J. Nelson, J. Devanathan, A. Shin, and J. J. Pancrazio, "Novel method for predicting dexterous individual finger movements by imaging muscle activity using a wearable ultrasonic system," IEEE Trans. Neural Syst. Rehabil. Eng., vol. 22, No. 1, pp. 69-76, 2013.
Sikdar, S.; Rangwala, H.; Eastlake, E.B.; Hunt, I.A.; Nelson, A.J.; Devanathan, J.; Shin, A.; Pancrazio, J.J. Novel method for predicting dexterous individual finger movements by imaging muscle activity using a wearable ultrasonic system. IEEE Trans. Neural Syst. Rehabil. Eng. 2013, 22, 69-76.
Stein, R. B., Bélanger, M., Wheeler, G., Wieler, M., Popovi6c, D. B., Prochazka, A., and Davis, L. A., 1993. "Electrical systems for improving locomotion after incomplete spinal cord injury: An assessment". Arch. Phys. Med. Rehabil., 74(9), pp. 954-959.
Takahashi, et al., "A neuromechanics based powered ankle exoskeleton to assist walking post-stroke: a feasibility study," J. Neuroeng. Rehabil., vol. 12, No. 1, p. 23, 2015.
Tamburella, et al., "Neuromuscular controller embedded in a powered ankle exoskeleton: Effects on gait, clinical features and subjective perspective of incomplete spinal cord injured subjects," IEEE Trans. Neural Syst. Rehabil. Eng., vol. 28, No. 5, pp. 1157-1167, 2020.
The National SCI Statistical Center. Spinal Cord Injury (SCI) facts and figures at a glance, 2017.
Tzu-wei Huang, et al., "Mechanical and energetic consequences of reduced ankle plantarflexion in human walking," J. Exp. Biol., vol. 218, No. 22, pp. 3541-3550, 2015.
Vaillancourt and K. M. Newell, "The dynamics of resting and postural tremor in parkinson's disease," Clinical Neurophysiology, vol. 111, No. 11, pp. 2046-2056, 2000.
Vigotsky, et al., "Interpreting signal amplitudes in surface electromyography studies in sport and rehabilitation sciences," Front. Physiol., vol. 8, p. 985, 2018.
Villarreal and R. D. Gregg, "A survey of phase variable candidates of human locomotion," in 2014 36th Annual International Conference of the IEEE Engineering in Medicine and Biology Society. IEEE, 2014, pp. 4017-4021.
Virani, S.S.; Alonso, A.; Benjamin, E.J.; Bittencourt, M.S.; Callaway, C.W.; Carson, A.P.; Chamberlain, A.M.; Chang, A.R.; Cheng, S.; Delling, F.N.; others. Heart disease and stroke statistics—2020 update: a report from the American Heart Association. Circulation 2020, 141, e139-e596.
Vøllestad, N.K. Measurement of human muscle fatigue. J. Neurosci. Methods 1997, 74, 219-227.
Wilhelm, A. Rech, F. Minozzo, R. Radaelli, C. E. Botton, and R. S. Pinto, "Relationship between quadriceps femoris echo intensity, muscle power, and functional capacity of older men," Age, vol. 36, No. 3, pp. 1113-1122, Jun. 2014.
Witte, J. Zhang, R. W. Jackson, and S. H. Collins, "Design of two lightweight, high-bandwidth torque-controlled ankle exoskeletons," in 2015 IEEE International Conference on Robotics and Automation (ICRA), pp. 1223-1228, IEEE, 2015.
Witte, R.S.; Kim, K.; Martin, B.J.; O'Donnell, M. Effect of fatigue on muscle elasticity in the human forearm using ultrasound strain imaging. Proc. IEEE Int. Conf. Eng. Med. Biol. Soc. IEEE, 2006, pp. 4490-4493.

(56) References Cited

OTHER PUBLICATIONS

Wolbrecht, V. Chan, D. J. Reinkensmeyer, and J. E. Bobrow, "Optimizing compliant, model-based robotic assistance to promote neurorehabilitation," IEEE Trans. Neural Sys. Rehabil. Eng., vol. 16, No. 3, pp. 286-297, 2008.
Yoshitake, Y.; Ue, H.; Miyazaki, M.; Moritani, T. Assessment of lower-back muscle fatigue using electromyography, mechanomyography, and near-infrared spectroscopy. Eur. J. Appl. Physiol. 2001, 84, 174-179.
Young and Ferris, "State of the art and future directions for lower limb robotic exoskeletons," IEEE Trans. Neural Sys. Rehabil. Eng., vol. 25, No. 2, pp. 171-182, 2017.
Zajac, "Muscle and tendon: properties, models, scaling, and application to biomechanics and motor control.," Crit. Rev. Biomed. Eng., vol. 17, No. 4, pp. 359-411, 1989.
Zhang, A. Iyer, Z. Sun, A. Dodson, and N. Sharma, "Sampled data observer based dynamic surface control of delayed neuromuscular functional electrical stimulation," in Dynamic Systems and Control Conference, vol. 84270. American Society of Mechanical Engineers, 2020, p. V001T14A003.
Zhang, A. Iyer, Z. Sun, K. Kim, and N. Sharma, "A Dual-Modal Approach Using Electromyography and Sonomyography Improves Prediction of Dynamic Ankle Movement: A Case Study," IEEE Trans. Neural Syst. Rehabil. Eng., vol. 29, pp. 1944-1954, 2021.
Zhang, D., and Shen, Y., 2017. "Global output feedback sampled-data stabilization for upper-triangular nonlinear systems with improved maximum allowable transmission delay". Int. J. Robust Nonlinear Control, 27(2), pp. 212-235.
Zhang, et al., "Ultrasound-based sensing and control of functional electrical stimulation for ankle joint dorsiflexion: Preliminary study," in International Symposium on Wearable Robotics. Springer, 2020, pp. 307-311.
Zhang, N. Fragnito, A. Myers, and N. Sharma, "Plantarflexion Moment Prediction during the Walking Stance Phase with an sEMGUltrasound Imaging-Driven Model," in 2021 Annual International Conference of the IEEE Engineering in Medicine and Biology Society. IEEE, 2021, Accepted.
Zhang, N. Fragnito, J. Franz, and N. Sharma, "Fused Ultrasound and Electromyography-drivenNeuromuscular model to improve PlantarflexionMoment Prediction across Multiple Walking Speeds," J. Neuroeng. Rehabil., vol. 86, No. 19, pp. 1-20, 2022.
Zhang, P. Fiers, K. A. Witte, R. W. Jackson, K. L. Poggensee, C. G. Atkeson, and S. H. Collins, "Human-in-the-loop optimization of exoskeleton assistance during walking," Science, vol. 356, No. 6344, pp. 1280-1284, 2017.
Zhang, Q., Sheng, Z., Kim, K., and Sharma, N., 2019. "Observer design for a nonlinear neuromuscular system with multi-rate sampled and delayed output measurements". In Proc. Am. Control Conf., IEEE, pp. 872-877.
Zhang, Q.; Hayashibe, M.; Fraisse, P.; Guiraud, D. FES-induced torque prediction with evoked EMG sensing for muscle fatigue tracking. IEEE/ASME Trans. Mechatronics 2011, 16, 816-826.
Zhang, Q.; Iyer, A.; Kim, K.; Sharma, N. Evaluation of Non-invasive Ankle Joint Effort Prediction Methods for Use in Neuro-rehabilitation Using Electromyography and Ultrasound Imaging. IEEE Trans. Biomed. Eng. 2021, 68, 1044-1055.
Zhang, Q.; Iyer, A.; Lambeth, K.; Kim, K.; Sharma, N. Ultrasound Echogenicity-based Assessment of Muscle Fatigue During Functional Electrical Stimulation. 2021 Annual International Conference of the IEEE Engineering in Medicine and Biology Society. IEEE, 2021, Accepted.
Zhang, Q.; Iyer, A.; Sun, Z.; Kim, K.; Sharma, N. A Dual-modal Approach Using Electromyography and Sonomyography Improves Prediction of Dynamic Ankle Dorsiflexion Motion. IEEE Trans. Neural Syst. Rehabil. Eng. 2021, Accepted.
Zhang, Q.; Kim, K.; Sharma, N. Prediction of Ankle Dorsiflexion Moment by Combined Ultrasound Sonography and Electromyography. IEEE Trans. Neural Syst. Rehabil. Eng. 2020, 28, 318-327.
Zhang, Qiang, et al. "A deep learning method to predict ankle joint moment during walking at different speeds with ultrasound imaging: A framework for assistive devices control." Wearable Technologies 3 (2022): e20.
Zhang, Qiang, et al. "Evaluation of a fused sonomyography and electromyography-based control on a cable-driven ankle exoskeleton." IEEE Transactions on Robotics (2023).
Zhang, Qiang, et al. "Personalized fusion of ultrasound and electromyography-derived neuromuscular features increases prediction accuracy of ankle moment during plantarflexion." Biomedical Signal Processing and Control 71 (2022): 103100.
Zhang, Qiang, et al. "Ultrasound echogenicity as an indicator of muscle fatigue during functional electrical stimulation." Sensors 22.1 (2022): 335.
Zhang, Qiang, et al. "Ultrasound Imaging-Based Closed-Loop Control of Functional Electrical Stimulation for Drop Foot Correction." IEEE Transactions on Control Systems Technology (2022).
Zhang, W. H. Clark, J. R. Franz, and N. Sharma, "Personalized fusion of ultrasound and electromyography-derived neuromuscular features increases prediction accuracy of ankle moment during plantarflexion," Biomed. Signal Process. Control, 2021, Accepted.
Zhou, D. L. Lawson, W. E. Morrison, and I. Fairweather, "Electromechanical delay in isometric muscle contractions evoked by vol-untary, reflex and electrical stimulation," Eur. J. Appl. Physiol. Occup. Physiol., vol. 70, No. 2, pp. 138-145, 1995.
Zhuang, et al., "Admittance control based on emg-driven musculoskeletal model improves the human-robot synchronization," IEEE Trans. Ind. Inform., vol. 15, No. 2, pp. 1211-1218, 2018.

* cited by examiner (c)

(b)

(a)

(a) Typical tracking results without disturbance in Task 5.

(b) Typical tracking results with disturbance in Task 5.

FIG. 29
Cycle 4, R: 0.335
Cycle 8, R: 0.347
Cycle 12, R: 0.365
Cycle 16, R: 0.366
Cycle 20, R: 0.382
Cycle 24, R: 0.406
Cycle 28, R: 0.412
Cycle 32, R: 0.417
Cycle 36, R: 0.419
Cycle 40, R: 0.421
Cycle 44, R: 0.423
Cycle 48, R: 0.423
Cycle 52, R: 0.424
Cycle 56, R: 0.427
Cycle 60, R: 0.427
Cycle 64, R: 0.436
Cycle 68, R: 0.439
Cycle 72, R: 0.441
Cycle 76, R: 0.441
Cycle 80, R: 0.456
Cycle 84, R: 0.46
Cycle 88, R: 0.462
Cycle 92, R: 0.462
Cycle 96, R: 0.474
Cycle 100, R: 0.484
Cycle 104, R: 0.484
Cycle 108, R: 0.5
Cycle 112, R: 0.5
Cycle 116, R: 0.501
Cycle 120, R: 0.502

Mean and SD values of net plantarflexion torque prediction RMSE results based on different HNMs across all stance cycles within the recorded one-minute walking duration and peak torque from benchmark measurements.

(Unit: N ·m)

| Condition | S1 | | | | | S2 | | | | | S3 | | | | |
|---|---|---|---|---|---|---|---|---|---|---|---|---|---|---|---|
| Subject | sEMG | | sEMG-US | | Peak | sEMG | | sEMG-US | | Peak | sEMG | | sEMG-US | | Peak |
| | Mean | SD | Mean | SD | | Mean | SD | Mean | SD | | Mean | SD | Mean | SD | |
| A01 | 18.89 | 6.19 | 15.32* | 4.01 | 107.08 | 10.53 | 6.69 | 6.91* | 4.39 | 100.44 | 11.13 | 4.36 | 8.81* | 3.61 | 107.05 |
| A02 | 14.32 | 5.99 | 9.74* | 4.45 | 106.55 | 14.85 | 5.29 | 10.48* | 4.06 | 111.77 | 10.86 | 5.04 | 7.47* | 4.96 | 119.97 |
| A03 | 16.97 | 6.54 | 13.94* | 5.43 | 130.26 | 12.41 | 2.32 | 10.18 | 2.68 | 130.05 | 12.06 | 4.09 | 11.05 | 4.06 | 128.11 |
| A04 | 16.47 | 7.72 | 13.76* | 9.61 | 109.48 | 13.19 | 5.94 | 10.46 | 5.28 | 112.79 | 16.37 | 7.09 | 13.25* | 5.65 | 111.41 |
| A05 | 19.64 | 5.48 | 16.16* | 4.61 | 108.44 | 21.36 | 7.51 | 16.12* | 6.95 | 126.66 | 24.11 | 8.88 | 19.62* | 8.64 | 130.05 |

* represents that the torque prediction RMSE when using sEMG-US imaging-driven HNM is significantly less than that when using sEMG-driven HNM with respect to the given scenario and participant.

FIG. 41

Necessary design parameters and control gains for the proposed AAN framework. $I_{10}$ - 10×10 identity matrix.

| Parameter/gain | Value | Parameter/gain | Value |
|---|---|---|---|
| $h_s$ | 0.001 $s$ | $N_1$ | 10 |
| $N_s$ | 0.128 $s$ | $N_2$ | 10 |
| $M_s$ | 0.01 $s$ | $\delta_1$ | 0.5 |
| $J_A$ | 0.15 $kgm^2$ | $\delta_2$ | 1.0 |
| $C_d$ | 0.15 $Nms/rad/kg$ | $\gamma_1$ | 0.01 |
| $K_d$ | 4.0 $Nm/rad/kg$ | $\gamma_2$ | 0.02 |
| $\alpha$ | 6.8 | $\Gamma_1$ | $I_{10}$ |
| $\beta$ | 0.02 | $\Gamma_2$ | $I_{10}$ |
| $k_s$ | 2.2 | | |

FIG. 42

Results of muscle activation decay constant $T_a$ and EMD $\tau_M$ from the system identification testing under isometric configuration on individual participants.

| Participant | A01 | A02 | A03 | A04 | A05 | Mean | SD |
|---|---|---|---|---|---|---|---|
| $T_a$ [s] | 0.26 | 0.41 | 0.33 | 0.24 | 0.30 | 0.31 | 0.07 |
| $\tau_M$ [ms] | 103 | 121 | 108 | 118 | 95 | 109 | 10 |

FIG. 43

Mean and SD values of ankle joint real trajectories in 30 swing phases in *Task* 1, *Task* 2, and *Task* 3 on each participant. (Unit: °)

| Condition | *Task* 1 | | *Task* 2 | | *Task* 3 | |
|---|---|---|---|---|---|---|
| Participant | Mean | SD | Mean | SD | Mean | SD |
| A01 | -4.16 | 5.96 | -19.80 | 2.19 | -11.57 | 4.69 |
| A02 | -7.76 | 4.77 | -17.36 | 5.62 | -8.32 | 7.67 |
| A03 | -7.09 | 2.67 | -14.55 | 5.44 | -7.62 | 4.75 |
| A04 | -3.73 | 3.74 | -23.61 | 5.67 | -5.38 | 5.21 |
| A05 | -0.74 | 4.01 | -11.12 | 3.26 | -1.66 | 4.41 |
| Mean | -4.70 | 4.23 | -17.28 | 4.43 | -6.91 | 5.35 |

FIG. 44

Summarized results of disturbance rejection performance by using the US-based DSC-DC controller. (Data are from the first 20 swing cycles in *Task* 3 and *Task* 5, and $Dis_{on}$ ($Dis_{off}$) represents with (without) plantarflexion disturbance.)

| | A01 RMSE | | A02 RMSE | | A03 RMSE | | A04 RMSE | | A05 RMSE | |
|---|---|---|---|---|---|---|---|---|---|---|
| Unit [°] | Mean | SD | Mean | SD | Mean | SD | Mean | SD | Mean | SD |
| $Dis_{on}$ | 3.61 | 1.38 | 3.15 | 1.66 | 4.07 | 0.74 | 3.38 | 1.26 | 4.18 | 1.89 |
| $Dis_{off}$ | 2.92 | 1.15 | 2.63 | 0.74 | 3.61 | 0.86 | 3.21 | 0.92 | 3.32 | 1.43 |
| | A01 RMSPW | | A02 RMSPW | | A03 RMSPW | | A04 RMSPW | | A05 RMSPW | |
| Unit [$\mu s$] | Mean | SD | Mean | SD | Mean | SD | Mean | SD | Mean | SD |
| $Dis_{on}$ | 288.62 | 26.66 | 374.05 | 29.97 | 240.23 | 42.76 | 270.14 | 50.72 | 258.68 | 43.99 |
| $Dis_{off}$ | 238.09 | 22.53 | 281.22 | 60.33 | 225.43 | 26.49 | 144.55 | 56.21 | 219.17 | 75.75 |

FIG. 45

FES pulse width threshold and saturation values from each participant (Unit: μs)

| Participant | Sub01 | Sub02 | Sub03 | Sub04 | Sub05 | Sub06 | Sub07 | Sub08 |
|---|---|---|---|---|---|---|---|---|
| Threshold | 100 | 40 | 20 | 20 | 60 | 80 | 60 | 40 |
| Saturation | 420 | 580 | 520 | 500 | 520 | 500 | 400 | 560 |

FIG. 46

Coefficients of exponential regression models ($y = a \exp(bx) + c$) and $R^2$ values between each variable and the TA muscle contraction cycles.

| Participants | Coefficients and $R^2$ of exponential regression models | | | | | | | |
|---|---|---|---|---|---|---|---|---|
| | Isometric condition | | | | Dynamic condition | | | |
| | *a* | *b* | *c* | $R^2$ | *a* | *b* | *c* | $R^2$ |
| Sub01 | 0.955 | -0.022 | 0.015 | 0.929 | 0.952 | -0.016 | 0.115 | 0.923 |
| Sub02 | 0.948 | -0.018 | 0.098 | 0.919 | 0.600 | -0.020 | 0.405 | 0.904 |
| Sub03 | 0.931 | -0.019 | 0.005 | 0.876 | 0.894 | -0.034 | 0.186 | 0.965 |
| Sub04 | 0.515 | -0.020 | 0.502 | 0.942 | 0.732 | -0.048 | 0.453 | 0.940 |
| Sub05 | 0.616 | -0.019 | 0.760 | 0.957 | 0.733 | -0.037 | 0.377 | 0.926 |
| Sub06 | 0.981 | -0.011 | 0.428 | 0.803 | 0.478 | -0.037 | 0.526 | 0.888 |
| Sub07 | 0.824 | -0.018 | 0.301 | 0.904 | 0.518 | -0.049 | 0.567 | 0.911 |
| Sub08 | 0.835 | -0.031 | 0.165 | 0.925 | 0.457 | -0.053 | 0.631 | 0.907 |
| Sub01 | 0.581 | -0.082 | 0.598 | 0.967 | 0.634 | -0.025 | 0.436 | 0.919 |
| Sub02 | 0.390 | -0.036 | 0.193 | 0.772 | 0.751 | -0.013 | 0.119 | 0.763 |
| Sub03 | 0.643 | -0.073 | 0.497 | 0.899 | 0.867 | -0.062 | 0.350 | 0.857 |
| Sub04 | 0.695 | -0.060 | 0.452 | 0.966 | 0.622 | -0.026 | 0.449 | 0.919 |
| Sub05 | 0.730 | -0.036 | 0.193 | 0.771 | 0.751 | -0.013 | 0.119 | 0.763 |
| Sub06 | 0.665 | -0.055 | 0.455 | 0.966 | 0.642 | -0.046 | 0.408 | 0.919 |
| Sub07 | 0.618 | -0.057 | 0.398 | 0.891 | 0.691 | -0.038 | 0.309 | 0.863 |
| Sub08 | 0.724 | -0.046 | 0.344 | 0.895 | 0.685 | -0.039 | 0.308 | 0.865 |

FIG. 47

Coefficients of linear regression models ($y = ax + b$) and $R^2$ values between dorsiflexion torque/angle normal- ization and ERC normalization.

| Participants | Coefficients and $R^2$ of linear regression models | | | | | | | | | |
|---|---|---|---|---|---|---|---|---|---|---|
| | Isometric condition | | | | | Dynamic condition | | | | |
| | $a$ | $p$- value | $b$ | $p$- value | $R^2$ | $a$ | $p$- value | $b$ | $p$- value | $R^2$ |
| Sub01 | 0.895 | $1.30e^{-6}$ | 0.245 | 0.091 | 0.889 | 1.009 | $2.22e^{-14}$ | -0.014 | 0.773 | 0.879 |
| Sub02 | 0.894 | $2.81e^{-5}$ | -0.118 | 0.025 | 0.852 | 1.036 | $1.92e^{-8}$ | -0.155 | 0.079 | 0.682 |
| Sub03 | 0.879 | $3.44e^{-10}$ | 0.124 | 0.002 | 0.879 | 0.752 | $6.55e^{-9}$ | 0.161 | 0.003 | 0.827 |
| Sub04 | 1.475 | $3.30e^{-8}$ | -0.555 | $1.17e^{-4}$ | 0.911 | 0.900 | $6.14e^{-13}$ | 0.126 | $5.90e^{-3}$ | 0.847 |
| Sub05 | 0.928 | $1.65e^{-5}$ | -0.168 | 0.117 | 0.763 | 0.800 | $5.80e^{-8}$ | 0.068 | 0.274 | 0.756 |
| Sub06 | 0.754 | $2.18e^{-5}$ | 0.206 | 0.224 | 0.843 | 1.245 | $1.25e^{-12}$ | -0.144 | 0.036 | 0.839 |
| Sub07 | 1.319 | $4.65e^{-6}$ | -0.248 | 0.026 | 0.811 | 1.019 | $1.35e^{-11}$ | 0.005 | 0.261 | 0.763 |
| Sub08 | 1.169 | $1.23e^{-5}$ | -0.234 | 0.083 | 0.771 | 0.955 | $1.34e^{-7}$ | 0.133 | 0.155 | 0.755 |
| Mean | 1.039 | — | -0.094 | — | 0.840 | 0.965 | — | 0.023 | — | 0.794 |
| Standard deviation | 0.253 | — | 0.271 | — | 0.054 | 0.154 | — | 0.123 | — | 0.065 |

FIG. 48

LIST OF PARAMETERS USED IN EXPERIMENT

| Parameter | $\alpha$ | $\beta$ | $K_u$ | $K_v$ | $r_e$ | $\omega_f$ ($s^{-1}$) | $\omega_r$ ($s^{-1}$) | sat (mA) | thresh (mA) |
|---|---|---|---|---|---|---|---|---|---|
| Value | 80 | 2 | 2 | 2 | 0.05 | 1/11 | 1/25 | 50 | 21 |

RESULTS OF KNEE JOINT TRACKING USING THE DESIGNED CLOSED-LOOP CONTROL SYSTEM.

| Trial number | | 1 | 2 | 3 | 4 | 5 | 6 | 7 |
|---|---|---|---|---|---|---|---|---|
| RMSE (°) | | 1.60 | 1.84 | 1.48 | 1.85 | 1.75 | 1.98 | 1.89 |
| Switch threshold | upper | 0.9 | 0.9 | 0.9 | 0.9 | 0.9 | 0.9 | 0.9 |
| | lower | 0.8 | 0.8 | 0.8 | 0.8 | 0.8 | 0.8 | 0.8 |
| Ultrasound frame rate (Hz) | | 1600 | 250 | 500 | 500 | 1000 | 1000 | 800 |
| Ultrasound trigger delay (ms) | | 100 | 100 | 100 | 160 | 160 | 160 | 160 |

FIG. 49

SYSTEMS FOR CLOSED-LOOP ULTRASOUND-IMAGING BASED CONTROL AND RELATED METHODS

CROSS-REFERENCE TO RELATED APPLICATIONS

This application claims priority to and incorporates by reference herein U.S. Patent Application Ser. No. 63/251,878, entitled SYSTEMS FOR CLOSED-LOOP ULTRASOUND-IMAGING BASED CONTROL AND RELATED METHODS, the contents of which is hereby incorporated by this reference in its entirety as if fully set forth herein.

STATEMENT REGARDING FEDERALLY FUNDED RESEARCH

This invention was made with government support under Grant no. CBET2002261 awarded by the National Science Foundation. The government has certain rights in the invention.

BACKGROUND

Drop foot is a typical symptom of weakened ankle dorsiflexion after cerebral vascular accidents and neurological disorders such as multiple sclerosis or incomplete spinal cord lesions. Affected persons are unable to exhibit normal foot ground clearance during the swing phase, resulting in unnatural steppage gait to avoid tripping/falls. To correct drop foot, functional electrical stimulation (FES), which is an artificial technique to apply electrical potentials across skeletal muscles, can be applied on the tibialis anterior (TA) muscle and induce orthotic effects at the ankle joint. Traditionally, the TA muscle is activated during the swing phase using discrete sensors that detect either heel contact or leg inclination. Here, FES is applied through an open-loop or a trigger-based control method. The stimulation amplitude is fixed or uses a pre-determined trapezoidal shape. Thus, current commercial drop foot stimulators' inability to modulate the stimulation intensity accordingly is a major drawback, given the nonlinear and time-varying nature of FES.

SUMMARY

An example system includes an ultrasound transducer, and a controller operably coupled to the ultrasound transducer. The controller includes a processor and memory, the memory having computer-executable instructions stored thereon. The controller is configured to receive an ultrasound imaging signal associated with a subject's muscular activity from the ultrasound transducer; process the ultrasound imaging signal to obtain a feedback signal; and control a device interfacing with the subject based on the feedback signal.

Another example system includes an ultrasound transducer; a plurality of kinematic sensors; a stimulation device including a stimulus generator and at least two electrodes, where the at least two electrodes are operably coupled to the stimulus generator; and a controller. The controller includes a processor and memory, the memory having computer-executable instructions stored thereon. The controller is configured to: receive an ultrasound imaging signal associated with a subject's muscular activity from the ultrasound transducer; process the ultrasound imaging signal to obtain a first feedback signal; process respective kinematic sensor signals from the kinematic sensors to obtain a second feedback signal; and control the stimulation device based on the first and second feedback signals.

Another example system includes an ultrasound transducer; a sensor configured to measure a subject's muscular activity; a powered joint exoskeleton; and a controller. The controller includes a processor and memory, the memory having computer-executable instructions stored thereon. The controller is configured to: receive an ultrasound imaging signal associated with the subject's muscular activity from the ultrasound transducer; receive a sensor signal from the sensor; combine data from the ultrasound imaging signal and the sensor signal to create a fused signal; analyze the fused signal to detect the subject's muscular activity; predict a joint torque based on the subject's detected muscular activity; and control a torque assistance of the powered joint exoskeleton based on the predicted joint torque.

Another example system includes an ultrasound transducer; a stimulation device including a stimulus generator and at least two electrodes, where the at least two electrodes are operably coupled to the stimulus generator; and a controller. The controller includes a processor and memory, the memory having computer-executable instructions stored thereon. The controller is configured to: receive an ultrasound imaging signal associated with a subject's muscular activity from the ultrasound transducer; process the ultrasound imaging signal to quantify the subject's muscular activity; and control the stimulation device based on based on the subject's quantified muscular activity to suppress a tremor.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 41 is a schematic diagram according to implementations described herein.

FIG. 42 is a schematic diagram according to implementations described herein.

FIG. 43 is a schematic diagram according to implementations described herein.

FIG. 44 is a schematic diagram according to implementations described herein.

FIG. 45 is a schematic diagram according to implementations described herein.

FIG. 46 is a schematic diagram according to implementations described herein.

FIG. 47 is a schematic diagram according to implementations described herein.

FIG. 48 is a schematic diagram according to implementations described herein.

FIG. 49 is a schematic diagram according to implementations described herein.

DETAILED DESCRIPTION

Figure 1:
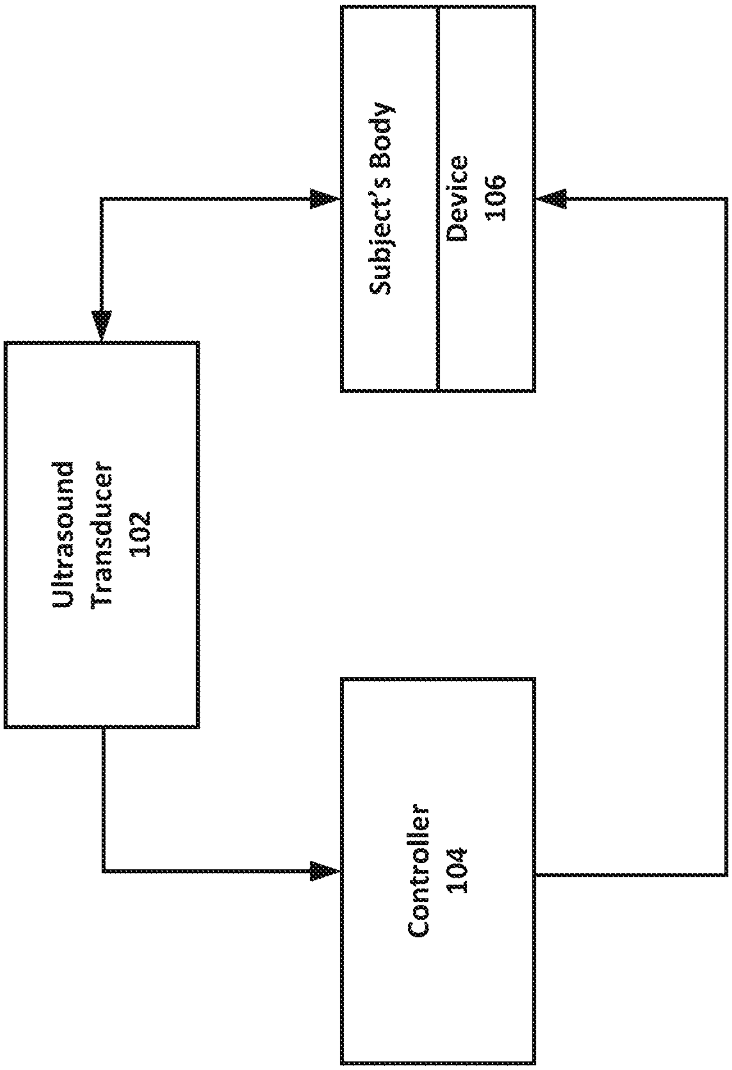
FIG. 1 is a block diagram of a closed-loop control system according to implementations described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "about" or "approximately" when referring to a measurable value such as an amount, a percentage, and the like, is meant to encompass variations of ±20%, ±10%, ±5%, or ±1% from the measurable value.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

A non-invasive system and method for controlling functional electrical stimulation (FES) and a cable-driven ankle exoskeleton using ultrasound imaging and electromyography are described below. The systems and methods can be used to predict a person's voluntary ankle torque during walking from a fused signal obtained from ultrasound imaging and electromyography. A control system that uses the torque prediction to provide necessary assistance using either FES or ankle exoskeleton or a combination of both is also described herein.

This is a first-time demonstration of a closed-loop system that uses signals derived from ultrasound imaging to control FES and/or an ankle exoskeleton. These ultrasound imaging signals capture mechanical features of a human muscle such as echogenicity, muscle fascicle length, pennation angle, muscle thickness, muscle strength, etc. Also described herein are techniques to fuse the ultrasound imaging signals with electromyography (EMG) in real-time. Current technologies are unable to fuse these two signals as the EMG is sampled at a higher rate while ultrasound imaging has a lower sampling rate. The methods described herein address how signals can be made available to a controller that operates at a higher control frequency. A bidirectional wearable cable-driven exoskeleton is also described, including a technique to map the desired torque at the cable end to the electric motor. This torque assistance is computed based on the predicted torque determined using the fused ultrasound imaging+EMG modeled torque. The designed system can be used to assist or restore mobility after an ankle impairment such as a drop foot as seen in people who have a stroke, incomplete spinal cord injury, or multiple sclerosis.

Another non-invasive system and method for measuring tremor frequency of muscles in people who have essential tremor or Parkinson disease is described below. The method uses ultrasound to quantify muscle contractility during tremor. The measured frequency is used to determine stimulation current and frequency to a set of non-invasive electrodes that are attached to the forearm. The electrodes send electrical currents to the tremoring muscles that upon stimulated, out of phase to the tremor frequency, suppress tremor. Further, the ultrasound is also optionally used to distinguish volitional muscle intent from the tremor. The closed-loop system can facilitate tremor suppression without inhibiting desired muscle movements.

The system can be worn on the forearm. Current methods require instrumentation on the hands and fingers that are visible and may look unsightly for day-to-activities. The current methodologies are limited to suppress tremor activity in fewer muscles. The system and method described herein instead uses distributed electrodes to suppress activity in multiple locations. Ultrasound can detect not only tremor but also predict volitional intent, which current technology does not provide. Thus, the systems and method described herein can not only suppress tremor but also provide additional assistance to persons with advanced disease where the disease patients have difficulty initiating limb movements despite their intent to move. Ultrasound based technique can provide additional assistance by reading the intent in the muscle contraction despite the presence of tremor.

Example Closed Loop Control Systems

Referring now to FIG. 1, a block diagram of an example closed-loop control system is shown. As described herein, closed-loop control is based on ultrasound imaging and performed in real time (i.e., online as opposed to offline). The system includes an ultrasound transducer 102, and a controller 104 operably coupled to the ultrasound transducer 102. This disclosure contemplates that the ultrasound transducer 102 and controller 104 can be coupled through one or more communication links. This disclosure contemplates the communication links are any suitable communication link. For example, a communication link may be implemented by any medium that facilitates data exchange between the ultrasound transducer 102 and controller 104 including, but not limited to, wired, wireless and optical links. Example communication links include, but are not limited to, a local area network (LAN), a wireless local area network (WLAN), a wide area network (WAN), a metropolitan area network (MAN), Ethernet, the Internet, or any other wired or wireless link such as WiFi, WiMax, 3G, 4G, or 5G.

The ultrasound transducer 102 can optionally be the L7.5SC Prodigy Probe from S-Sharp Corporation of New Taipei City, Taiwan. It should be understood that the above probe is provided only as an example. This disclosure contemplates that the ultrasound transducer 102 can be another ultrasound transducer known in the art. As described herein, the ultrasound transducer 102 is attached to the subject's body, for example, to a muscle of the subject. In some implementations, the ultrasound transducer 102 is attached to the subject's tibialis anterior muscle. In other implementations, the ultrasound transducer 102 is attached to the subject's forearm muscle. It should be understood that the tibialis anterior and forearm muscles are provided only as examples. This disclosure contemplates attaching the ultrasound transducer 102 to other muscles. Optionally, the ultrasound transducer 102 is attached to the body with a holder to facilitate ultrasound imaging.

Figure 2:
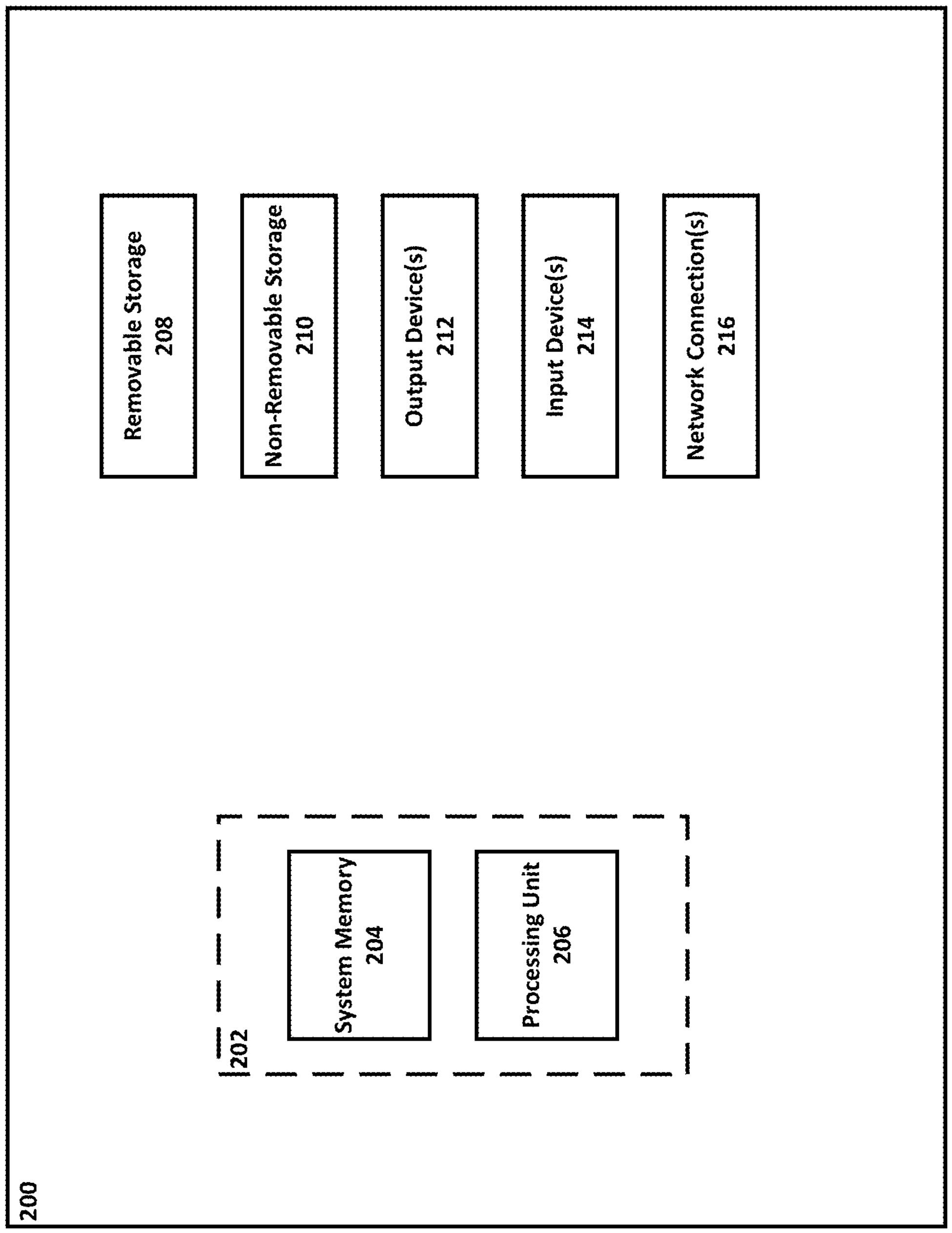
FIG. 2 is an example computing device.

The controller 104 includes at least a processor and memory (e.g., the basic configuration illustrated in FIG. 2 by dashed line 202). The controller 104 is configured to receive an ultrasound imaging signal associated with a subject's muscular activity from the ultrasound transducer 102. As described herein, the ultrasound transducer 102 is attached to the subject's body and configured to image the subject's muscle. Additionally, the controller 104 is configured to process the ultrasound imaging signal to obtain a feedback signal. Such processing can include, but is not limited to, determining a feature associated with a muscle. For example, the feature is at least one of echogenicity, a pennation angle of the muscle, a fascicle length of the muscle, or a thickness of the muscle.

Alternatively or additionally, such processing can include sampling the ultrasound imaging signal at a relatively low sampling rate as compared to other data as described herein. Optionally, this can be accomplished using a sampled-data based observer (SDO) module or a multi-rate observer module. The lower sampling rate enables use of the ultrasound imaging signal for real-time control, which would otherwise be prohibited due to processing overhead. As described herein, the ultrasound imaging signal is used to detect muscle activation. For example, the ultrasound imaging signal is used to detect stimulation-induced muscle contraction as described herein. Ultrasound imaging provides advantages over conventional electrical-based muscle activation detection techniques (e.g., EMG) because ultrasound is not impacted by stimulation artifact. In another example, the ultrasound imaging signal is used to detect voluntary muscle contraction as described herein. In yet another example, the ultrasound imaging signal is used to detect involuntary tremors as described herein.

Optionally, in some implementations, the system further includes a sensor configured to measure the subject's muscular activity. Such sensors can include, but are not limited to, an accelerometer, a gyroscope, a magnetometer, an inertial measurement unit (IMU), a force sensor, a strain sensor, or an electromyography (EMG) sensor. In these implementations, sensor fusion is used to detect muscle activation. In other words, data from the ultrasound imaging signal is combined (or merged) with data from one or more other sensors to create a fused signal. The controller 104 processes the fused signal to obtain the feedback signal.

The controller 104 is further configured to control a device 106 interfacing with the subject based on the feedback signal (i.e., closed-loop control). In some implementations, the device 106 includes a stimulus generator and at least two electrodes. The stimulus generator can be a voltage source or a current source. Optionally, the stimulus generator can be battery-powered. Optionally, the stimulus generate includes its own programmable logic (e.g., the basic configuration illustrated in FIG. 2 by dashed line 202). Stimulus generators are known in the art and therefore not described in further detail herein. Additionally, the at least two electrodes can be surface electrodes, e.g., electrodes configured to be applied to the subject's skin. This disclosure contemplates that the stimulus generator and the at least two electrodes can be coupled using a wired or wireless (e.g., radiofrequency (RF)) link. Electrodes are known in the art and therefore not described in further detail herein. In these implementations, the step of controlling the device 106 based on the feedback signal includes adjusting a characteristic of stimulation delivered to the subject by the stimulus generator. For example, the characteristic of the stimulation can be a current, a frequency, a pulse shape, a pulse width, a modulation scheme, etc. The stimulation can be designed to evoke muscle activity in some implementations. Alternatively, the stimulation can be designed to suppress or counteract muscle activity.

In other implementations, the device 106 includes a powered joint exoskeleton. In these implementations, the step of controlling the device 106 based on the feedback signal includes adjusting a torque assistance of the powered joint exoskeleton. Optionally, the powered joint exoskeleton is applied to the subject's ankle. The powered joint exoskeleton includes a frame, an actuation unit, an end-effector unit, and a cable. The frame can be constructed of three-dimensional printed material. The actuation unit and end-effector unit can be designed to be spaced apart (e.g., actuator at subject's hip and end-effector at subject's ankle). The cable operably couples the actuation unit and the end-effector unit. It should be understood that this reduces the weight of the exoskeleton in proximity to the joint.

Another example system according to one implementation described herein includes an ultrasound transducer; and a controller comprising a processor and memory, the memory having computer-executable instructions stored thereon that, when executed by the processor, cause the processor to: receive an ultrasound imaging signal associated with a subject's muscular activity from the ultrasound transducer; process the ultrasound imaging signal to obtain a feedback signal; and control a device interfacing with the subject based on the feedback signal.

In some implementations, processing the ultrasound imaging signal comprises determining a feature associated with a muscle.

In some implementations, the feature is at least one of echogenicity, a pennation angle of the muscle, a fascicle length of the muscle, a thickness of the muscle, or muscle strength.

In some implementations, the system further includes a sensor configured to measure the subject's muscular activity, wherein the memory has further computer-executable instructions stored thereon that, when executed by the processor, cause the processor to: receive a sensor signal from the sensor; combine data from the ultrasound imaging signal and the sensor signal to create a fused signal; and process the fused signal to obtain the feedback signal.

In some implementations, the sensor is at least one of an accelerometer, a gyroscope, a magnetometer, an inertial measurement unit (IMU), a force sensor, a strain sensor, or an electromyography (EMG) sensor.

In some implementations, the system further includes the device.

In some implementations, the device comprises a stimulus generator and at least two electrodes, wherein the at least two electrodes are operably coupled to the stimulus generator.

In some implementations, controlling the device based on the feedback signal comprises adjusting a characteristic of stimulation delivered to the subject by the stimulus generator.

In some implementations, the device includes a powered joint exoskeleton.

In some implementations, controlling the device based on the feedback signal comprises adjusting a torque assistance of the powered joint exoskeleton.

In some implementations, controlling the device based on the feedback signal comprises stopping stimulation based on at least one muscle feature.

In some implementations, the at least one muscle feature comprises echogenicity or muscle strength.

In some implementations, the subject's muscular activity is a voluntary or involuntary muscle contraction.

In some implementations, the voluntary or involuntary muscle contraction is ankle dorsiflexion or plantarflexion.

In some implementations, the voluntary or involuntary muscle contraction is a tremor.

In some implementations, the subject's muscular activity is a stimulation-induced muscle contraction.

In some implementations, the controller is configured for real-time control of the device based on the feedback signal.

In some implementations, the memory has further computer-executable instructions stored thereon that, when executed by the processor, cause the processor to: process the ultrasound imaging signal or controlling the device using a machine learning technique.

As used herein, the term "artificial intelligence" is defined herein to include any technique that enables one or more computing devices or comping systems (i.e., a machine) to mimic human intelligence. Artificial intelligence (AI) includes, but is not limited to, knowledge bases, machine learning, representation learning, and deep learning. The term "machine learning" is defined herein to be a subset of AI that enables a machine to acquire knowledge by extracting patterns from raw data. Machine learning techniques include, but are not limited to, logistic regression, support vector machines (SVMs), decision trees, Naïve Bayes classifiers, and artificial neural networks. The term "representation learning" is defined herein to be a subset of machine learning that enables a machine to automatically discover representations needed for feature detection, prediction, or classification from raw data. Representation learning techniques include, but are not limited to, autoencoders. The term "deep learning" is defined herein to be a subset of machine learning that that enables a machine to automatically discover representations needed for feature detection, prediction, classification, etc. using layers of processing. Deep learning techniques include, but are not limited to, artificial neural network or multilayer perceptron (MLP).

Machine learning models include supervised, semi-supervised, and unsupervised learning models. In a supervised learning model, the model learns a function that maps an input (also known as feature or features) to an output (also known as target or targets) during training with a labeled data set (or dataset). In an unsupervised learning model, the model learns patterns (e.g., structure, distribution, etc.) within an unlabeled data set. In a semi-supervised model, the model learns a function that maps an input (also known as feature or features) to an output (also known as target or target) during training with both labeled and unlabeled data.

The machine learning technique used to for processing the ultrasound imaging signal or controlling the device may be a supervised machine learning model. As described above, a supervised machine learning model is trained to learn patterns and uncover relationships between at least one target and at least one feature in a dataset. For example, machine learning models are trained with a data set. During training, weights, biases, parameters, rewards (e.g., Q-values), etc. associated with the machine learning model are adjusted to maximize or minimize a cost function. Once complete, the trained machine learning model is configured for inference mode, e.g., the trained machine learning model can make predictions based upon new data. Accordingly, in some implementations, this disclosure contemplates that a trained machine learning model can be deployed to process and obtain a feedback signal from the ultrasound imaging signal. Alternatively, or additionally, in some implementations, this disclosure contemplates that a trained machine learning model can be deployed to control the device.

In some implementations, the machine learning model may be an artificial neural network. An artificial neural network (ANN) is a computing system including a plurality of interconnected neurons (e.g., also referred to as "nodes"). This disclosure contemplates that the nodes can be implemented using a computing device (e.g., a processing unit and memory as described herein). The nodes can be arranged in a plurality of layers such as input layer, output layer, and optionally one or more hidden layers. An ANN having hidden layers can be referred to as deep neural network or multilayer perceptron (MLP). Each node is connected to one or more other nodes in the ANN. For example, each layer is made of a plurality of nodes, where each node is connected to all nodes in the previous layer. The nodes in a given layer are not interconnected with one another, i.e., the nodes in a given layer function independently of one another. As used herein, nodes in the input layer receive data from outside of the ANN, nodes in the hidden layer(s) modify the data between the input and output layers, and nodes in the output layer provide the results. Each node is configured to receive an input, implement an activation function (e.g., binary step, linear, sigmoid, tan H, or rectified linear unit (ReLU) function), and provide an output in accordance with the activation function. Additionally, each node is associated with a respective weight. ANNs are trained with a dataset to maximize or minimize an objective function. In some implementations, the objective function is a cost function, which is a measure of the ANN's performance (e.g., error such as L1 or L2 loss) during training, and the training algorithm tunes the node weights and/or bias to minimize the cost function. This disclosure contemplates that any algorithm that finds the maximum or minimum of the objective function can be used for training the ANN. Training algorithms for ANNs include, but are not limited to, backpropagation. It should be understood that an artificial neural network is provided only as an example supervised machine learning model. Optionally, the supervised machine learning model is a logistic regression, support vector machines (SVMs), decision trees, or Naïve Bayes classifiers. Logistic regression, support vector machines (SVMs), decision trees, and Naïve Bayes classifiers are known in the art and therefore not described in further detail herein. This disclosure contemplates that the machine learning model can be any supervised learning model, semi-supervised learning model, or unsupervised learning model.

Another example system according to one implementation described herein includes an ultrasound transducer; a plurality of kinematic sensors; a stimulation device including a stimulus generator and at least two electrodes, where the at least two electrodes are operably coupled to the stimulus generator; and a controller. The controller includes a processor and memory, the memory having computer-executable instructions stored thereon. The controller is configured to: receive an ultrasound imaging signal associated with a subject's muscular activity from the ultrasound transducer; process the ultrasound imaging signal to obtain a first feedback signal; process respective kinematic sensor signals from the kinematic sensors to obtain a second feedback signal; and control the stimulation device based on the first and second feedback signals.

Additionally, the kinematic sensors include one or more of a ground force sensor, an inertial measurement unit, or a joint angle encoder.

Alternatively or additionally, the step of processing the ultrasound imaging signal includes sampling the ultrasound imaging signal at a first sampling rate, and the step of processing the respective kinematic signals includes sampling the respective kinematic sensor signals at a second sampling rate. The first sampling rate is less than the second sampling rate. Optionally, the controller includes a sampled-data based observer (SDO) module configured to sample the ultrasound imaging signal at the first sampling rate.

Alternatively or additionally, the controller includes a dynamic surface control-delay compensation (DSC-DC) module configured to account for the subject's muscle activation dynamics and electromechanical delay.

In some implementations, processing the ultrasound imaging signal comprises determining a feature associated with a muscle.

Alternatively or additionally, the step of processing the ultrasound imaging signal includes determining a feature associated with a muscle. For example, the feature is at least one of echogenicity, a pennation angle of the muscle, a fascicle length of the muscle, a thickness of the muscle, or muscle strength.

Alternatively or additionally, the subject's muscular activity is a stimulation-induced muscle contraction. For example, the stimulation-induced muscle contraction is ankle dorsiflexion.

In some implementations, the controller is configured for real-time control of the stimulation device based on the first and second feedback signals.

In some implementations, the controller is configured to stop the stimulation device based on detected echogenicity or muscle strength.

Another example system according to one implementation described herein includes an ultrasound transducer; a sensor configured to measure a subject's muscular activity; a powered joint exoskeleton; and a controller. The controller includes a processor and memory, the memory having computer-executable instructions stored thereon. The controller is configured to: receive an ultrasound imaging signal associated with the subject's muscular activity from the ultrasound transducer; receive a sensor signal from the sensor; combine data from the ultrasound imaging signal and the sensor signal to create a fused signal; analyze the fused signal to detect the subject's muscular activity; predict a joint torque based on the subject's detected muscular activity; and control a torque assistance of the powered joint exoskeleton based on the predicted joint torque.

Additionally, the sensor is a surface electromyography (sEMG) sensor.

Alternatively or additionally, the step of combining data from the ultrasound imaging signal and the sensor signal includes sampling the ultrasound imaging signal at a first sampling rate and sampling the sensor signal at a second sampling rate. The first sampling rate is less than the second sampling rate.

Alternatively or additionally, the controller includes a multi-rate observer module configured to sample the ultrasound imaging signal and the sensor signal at the first and second sampling rates, respectively.

Alternatively or additionally, the controller includes a neuromuscular model module configured to predict the joint torque based on the subject's detected muscular activity.

Alternatively or additionally, the controller includes an adaptive impedance control (AIC) module configured to control the torque assistance of the powered joint exoskeleton based on the predicted joint torque.

Alternatively or additionally, the ultrasound imaging signal captures at least one of echogenicity, muscle pennation angle, muscle fascicle length, muscle thickness, or muscle strength.

Alternatively or additionally, the subject's muscular activity is ankle plantarflexion.

In some implementations, the powered joint exoskeleton includes a frame, an actuation unit, an end-effector unit, and a cable. The cable operably couples the actuation unit and the end-effector unit.

In some implementations, the controller is configured for real-time control of the torque assistance of the powered joint exoskeleton based on the predicted joint torque In some implementations, the controller is configured to stop torque assistance of the powered joint exoskeleton based on a detected echogenicity or muscle strength.

Another example system according to one implementation described herein includes an ultrasound transducer; a stimulation device including a stimulus generator and at least two electrodes, where the at least two electrodes are operably coupled to the stimulus generator; and a controller. The controller includes a processor and memory, the memory having computer-executable instructions stored thereon. The controller is configured to: receive an ultrasound imaging signal associated with a subject's muscular activity from the ultrasound transducer; process the ultrasound imaging signal to quantify the subject's muscular activity; and control the stimulation device based on based on the subject's quantified muscular activity to suppress a tremor.

Additionally, the step of processing the ultrasound imaging signal to quantify the subject's muscular activity includes determining a frequency of muscle contraction.

Alternatively or additionally, the step of controlling the stimulation device based on based on the subject's detected muscular activity to suppress the tremor includes selecting a characteristic of stimulation delivered to the subject by the stimulus generator.

In some implementations, the memory has further computer-executable instructions stored thereon that, when executed by the processor, cause the processor to differentiate between involuntary tremor and volitional muscle contraction.

In some implementations, the controller is configured for real-time control of the stimulation device based on based on the subject's detected muscular activity to suppress the tremor.

Example Computing Device

It should be appreciated that the logical operations described herein with respect to the various figures may be implemented (1) as a sequence of computer implemented acts or program modules (i.e., software) running on a computing device (e.g., the computing device described in FIG. 2), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Referring to FIG. 2, an example computing device 200 upon which the methods described herein may be implemented is illustrated. It should be understood that the example computing device 200 is only one example of a suitable computing environment upon which the methods described herein may be implemented. Optionally, the computing device 200 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 200 typically includes at least one processing unit 206 and system memory 204. Depending on the exact configuration and type of computing device, system memory 204 may be volatile (such as random-access memory (RAM)), non-volatile (such as read-only memory (ROM), flash memory, etc.), or some combination of the two. This most basic configuration is illustrated in FIG. 2 by dashed line 202. The processing unit 206 may be a standard programmable processor that performs arithmetic and logic operations necessary for operation of the computing device 200. The computing device 200 may also include a bus or other communication mechanism for communicating information among various components of the computing device 200.

Computing device 200 may have additional features/functionality. For example, computing device 200 may include additional storage such as removable storage 208 and non-removable storage 210 including, but not limited to, magnetic or optical disks or tapes. Computing device 200 may also contain network connection(s) 216 that allow the device to communicate with other devices. Computing device 200 may also have input device(s) 214 such as a keyboard, mouse, touch screen, etc. Output device(s) 212 such as a display, speakers, printer, etc. may also be included. The additional devices may be connected to the bus in order to facilitate communication of data among the components of the computing device 200. All these devices are well known in the art and need not be discussed at length here.

The processing unit 206 may be configured to execute program code encoded in tangible, computer-readable media. Tangible, computer-readable media refers to any media that is capable of providing data that causes the computing device 200 (i.e., a machine) to operate in a particular fashion. Various computer-readable media may be utilized to provide instructions to the processing unit 206 for execution. Example tangible, computer-readable media may include, but is not limited to, volatile media, non-volatile media, removable media and non-removable media implemented in any method or technology for storage of information such as computer readable instructions, data structures, program modules or other data. System memory 204, removable storage 208, and non-removable storage 210 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 206 may execute program code stored in the system memory 204. For example, the bus may carry data to the system memory 204, from which the processing unit 206 receives and executes instructions. The data received by the system memory 204 may optionally be stored on the removable storage 208 or the non-removable storage 210 before or after execution by the processing unit 206.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high-level procedural or object-oriented programming language to communicate with a computer system. However, the program(s) can be implemented in assembly or machine language, if desired. In any case, the language may be a compiled or interpreted language and it may be combined with hardware implementations.

Embodiments of the present disclosure present an assist-as-needed (AAN) control framework for exoskeleton assistance based on human volitional effort prediction via a Hill-type neuromuscular model (HNM). In some embodiments, a sequential processing algorithm-based multi-rate observer is applied to continuously estimate muscle activation levels by fusing surface electromyography (sEMG) and ultra-sound (US) echogenicity signals from the ankle muscles. In some embodiments, an adaptive impedance controller (AIC) manipulates the exoskeleton's impedance for a more natural behavior by following a desired intrinsic impedance model. Two neural networks provide robustness to uncertainties in the overall ankle joint-exoskeleton model and the prediction error in the volitional ankle joint torque. A rigorous Lyapunov-based stability analysis proves that the AAN control framework achieves uniformly ultimately bounded tracking for the overall system. Experimental studies on five participants with no neurological disabilities walking on a treadmill validate the effectiveness of the designed ankle exoskeleton and the proposed AAN approach. Results illustrate that the AAN control approach with fused sEMG and US echogenicity signals maintained a higher human volitional effort prediction accuracy, less ankle joint trajectory tracking error, and less robotic assistance torque than the AAN approach with the sEMG-based volitional effort prediction alone. The findings support our hypotheses that the proposed controller increases human motion intent prediction accuracy, improves the exoskeleton's control performance, and boosts voluntary participation from human subjects. The new framework potentially paves a foundation for using multi-modal biological signals to control rehabilitative or assistive robots.

Locomotion accounts for a dominant part of human activities of daily living, such as moving around the community, going to work or school, doing errands, etc. The human ankle plantarflexors play an essential role in achieving locomotion, especially for generating a large burst of "push-off" mechanical power during the late stance phase that enables forward and upward acceleration of the center of mass. However, a variety of neurological disorders, like spinal cord injury, stroke, and multiple sclerosis, weaken the plantarflexion function, cause a dramatic decrease in the "push-off" power that impairs walking, lead to a poor energy economy, and disrupt both physical and emotional well-being [2].

Recent advanced robotic devices such as powered ankle exoskeletons [3]-[6], ankle emulators [7], [8], soft exosuits [9], [10], and hybrid neuroprostheses [11]-[15] either aim to help people with neurological disorders regain ankle joint mobility and improve gait patterns or augment limb function and improve energy economy in persons without disabilities. Controllers in these robotic devices predominantly provide a priori defined torque/angle profiles [7], [10], [16]-[18], while some use neuromuscular reflexive rules [5], [19] that are event-triggered during different gait phases. The predefined joint torque profiles have also been optimized via human-in-the-loop optimization methods to reduce metabolic cost [7], [16] or muscles' electromyography (EMG)/surface EMG (sEMG) activities [19]. However, these control approaches mainly emphasize human augmentation and may not be designed to encourage human volitional effort, a relevant objective for neurorehabilitation.

A user-driven assistive device control approach can arguably expedite gait recovery in people with neurological disorders [20]. Considering human motion intent/voluntary effort while computing minimal robotic assistance, also known as assist-as-needed (AAN) control, is essential to increase muscle activities of the subject, encourage neuroplasticity, and maximize the recovery effects during rehabilitation training [21]-[23]. In [21], The inventors have developed a model-based adaptive AAN approach to learn the patient's abilities and assist in completing movements while remaining compliant. Hussain et al. [22]proposed an AAN control architecture for providing seamless adaptive robotic assistance to hip and knee joints during gait training, powered by pneumatic muscle actuators. In [23], Asl et al. proposed a novel adaptive neural network (NN) controller with input saturation to address the unknown system dynamics and external disturbances on the hip and knee joints of a lower limb robotic exoskeleton. These studies used NNs to estimate human volitional effort, which depended on the measures of interaction dynamics or estimates of the joint torque from inverse dynamics (ID). However, the nature of interaction dynamics and ID may not be appropriate in some cases, as the users must produce a torque on the joints that exceeds some threshold to initiate the motion before the devices can generate assistance. For example, if the users have a high-level muscle weakness and are not able to produce sufficient torques on their joints, such as may be the case for individuals with severe impairments, the robotic devices may not be successfully controlled. Fortunately, this disadvantage can be avoided by using human intent-based control of robotic devices according to physiological signals, like surface electromyography (sEMG), that are sent from the central nervous system (CNS) to the functional motor units.

Computing appropriate robotic assistance in an AAN control approach may be accomplished by predicting the user-generated volitional effort or motion intent from skeletal muscles' sEMG signals. In recent years, the use of sEMG-driven Hill-type neuromuscular model (HNM), as a human-machine-interface (HMI) to estimate the motion intent or residual volitional effort, has been particularly motivated to implement bio-inspired AAN control for enhancing voluntary participation of the user. For example, myoelectric controllers [19], [24]-[26]proportionally assist the user based on real-time recorded EMG signals. However, these model-free methods directly relied on sEMG signals and disregarded the highly nonlinear transformation from sEMG onset to joint torque generation. Instead, the neuromuscular model-based AAN control methods [27]-[30] use a nonlinear mapping to predict limb torques from sEMG signals. Subsequently, the proportional adjustment of the robotic assistance according to the biological joint torque estimation could be achieved [28]-[30]. Some studies bypassed the use of the complex neuromuscular model [31], [32] in the AAN control. Instead, the rectified and low-pass filtered EMG signals were used as inputs to a radial basis function NN (RBFNN) that was incorporated into a Slotine-Li adaptive controller [33].

Despite sEMG's impressive performance and wide application in rehabilitative/assistive devices control, its susceptibility to signal interference coming from neighboring muscles, low signal-to-noise ratio (SNR), and inability to measure contractions of deeply-located muscles [34]-[36] are significant hurdles for sEMG's use in HMIs and accurate muscle activation measures. As an alternative to sEMG-based HMIs, ultrasound (US) imaging has recently been applied to quantitatively measure muscle contractility. Its advantages over sEMG include direct muscle visualization, high SNR, and access to deep muscle layers. One-dimensional (pennation angle, fascicle length, muscle thickness [37], and echogenicity/image intensity [36], [38]-[40]), two-dimensional (tissue displacement or strain [41], [42]), and high-dimensional (implicit features from deep learning [43]) features have been investigated to characterize the muscle contraction force, net joint torque, and joint movement. However, nearly all studies above were offline due to computationally intensive US imaging beamforming and post-processing. In a recent disclosure [44], the soleus muscle average velocity profiles during versatile walking tasks were measured through pre-recorded US images and then used to estimate the muscle force and determine the exosuit assistance profile, which was proportional to the estimated muscle force. The muscle-based assistance approach was evaluated by calculating the reduction of metabolic cost with a bilateral ankle exosuit in a variety of walking conditions. Although this muscle-based approach enables rapid generation of individualized assistance profiles, the US images were processed offline; thus, the real-time feedback from US image-derived signals that estimate muscle force remains unexplored. Importantly, given the time-varying nature of the muscle force generation among gait cycles and the highly nonlinear relationship between muscle contractility and muscle force/joint moment, the desired assistance may deteriorate in the absence of real-time US imaging-derived feedback.

Figure 3:
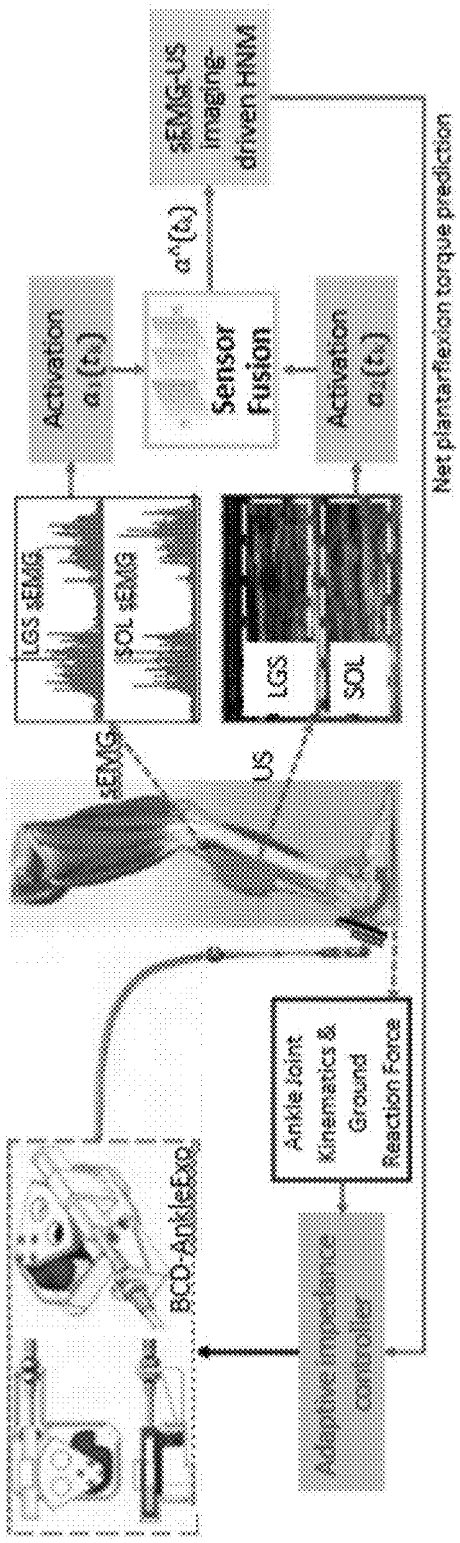
FIG. 3 is a schematic diagram according to implementations described herein.

Considering the aforementioned corresponding advantages from both sEMG and US imaging-based HMIs, recent evidence from offline studies has shown that the joint torque or motion intent prediction accuracy can be further increased by fusing US imaging-derived and sEMG-derived measures of muscle contractility [35], [45]-[47]. A probable reason for the improved accuracy of the dual-modal approach is that the dual-modal signals provide complementary electrical and mechanical information regarding the same muscle contraction activity. From the perspective of human volitional effort or motion intent prediction, since there is a lack of real-time methods for fusing sEMG and the US-derived signals, motivation exists to develop a data fusion algorithm for predicting the joint torque or motion intent online. Furthermore, few AAN control studies for robotic assistive devices have focused on the ankle joint or used any real-time sensor fusion between sEMG and US imaging signals, especially for locomotion tasks. Therefore, there is also a need for incorporating the novel data fusion algorithm into the control design of wearable robotic assistive devices, thus promoting a greater symbiosis between the robotic assistive device and the human user. To tackle these motivations, there are two main challenges: 1) the sparsity of US imaging measurement feedback, which causes different sampling rates of the US imaging and sEMG signals when used in the real-time closed-loop control framework; 2) the design of an intuitive AAN controller to adapt to the time-varying residual volitional effort or motion intent from HMIs. A combination of US imaging-derived echogenicity signals with sEMG signals is used to continuously predict human ankle joint net plantarflexion torque online during a walking task is proposed. The AAN control design incorporates the volitional effort prediction and an adaptive impedance controller (AIC) to automatically adjust the assistance levels from a bidirectional cable-driven ankle exoskeleton (BCD-AnkleExo). Referring now to FIG. 3, a schematic diagram depicting an overview of an exemplary system in accordance with some embodiments of the present disclosure is provided. As depicted, a voluntary torque prediction via an sEMG-US imaging-driven HNM that incorporates an AIC for adjusting the assistance of a BCD-AnkleExo is provided.

In some embodiments, a skeletal muscle's US imaging signals are used online in a real-time closed-loop control design of assistive robotic devices.

In some embodiments, a volitional net plantarflexion torque is predicted by using an sEMG-US imaging-driven Hill-type neuromuscular model (HNM), where the synthesized muscle activation signal is estimated by fusing both real-time low-sampled US imaging-derived echogenicity signals and high-sampled sEMG signals through a sequential processing algorithm-based multi-rate observer.

In some embodiments, the predicted torque is implemented in an NN-based adaptive impedance control (AIC)-based AAN framework that automatically adjusts the BCD-AnkleExo assistance while guaranteeing the uniformly ultimately bounded stability of the overall closed-loop system according to the Lyapunov stability analysis.

As discussed herein, the proposed AAN control framework is experimentally validated on five unimpaired participants when wearing the BCD-AnkleExo and walking on the treadmill. The comparison results show that the proposed control framework exhibits a superior performance over a traditional AAN control approach that only uses sEMG signals, where control outcomes include joint trajectory tracking error and assistance level from the exoskeleton.

Human Ankle Joint Volitional Effort Prediction

In accordance with some embodiments of the present disclosure a plantarflexion torque prediction model by synthesizing muscle activation from sEMG and US imaging-derived signals is provided. In some embodiments, a HNM-based torque prediction model that takes input from a fused muscle activation model is provided. In some embodiments, an approach to synthesize muscle activation from high-sampled sEMG and low-sampled US imaging signals is provided.

HNM-Based Formulation of Net Plantarflexion Torque Prediction

The main contributors for the net plantarflexion torque generation include lateral gastrocnemius (LGS) and soleus (SOL) muscles. An anatomical diagram of the ankle joint musculoskeletal system is shown in FIG. 4A-C.

Figure 4C:
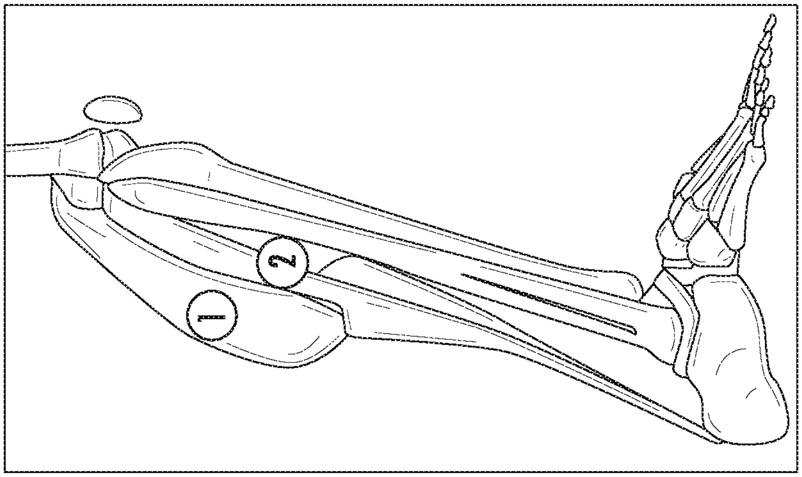
FIGS. 4A, 4B and 4C are schematic diagrams according to implementations described herein.
Figure 4B:
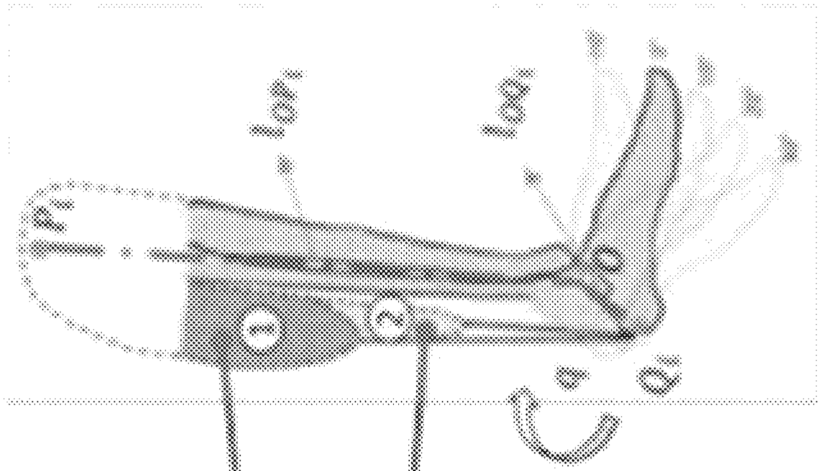
Figure 4A:
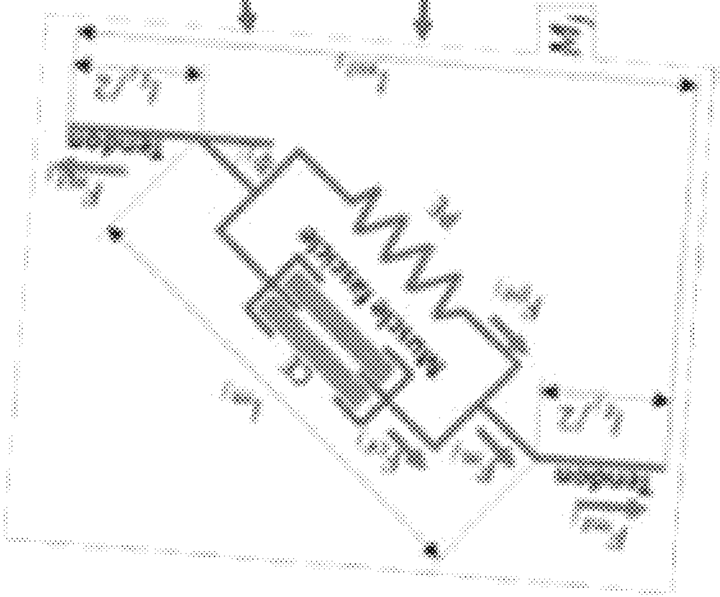

Referring now to FIG. 4A-C, an illustration of the Hill-type neuromuscular model for both the LGS and SOL muscles when performing ankle plantarflexion function is provided. As depicted: FIG. 4A is the LGS and SOL muscles' dynamic contraction diagram, FIG. 4*b* is a schematic representation of both LGS and SOL muscles' geometry model around the ankle joint, and FIG. 4(*c*) is the anatomical representation of both LGS and SOL muscles during the walking stance phase.

According to the HNM [48]-[52], the volitional net plantarflexion torque τnet(t) at the ankle, when only considering LGS and SOL muscles, is given as:

$$\tau_{net}(t) = \sum_{j=1}^{2} M_j(t) \tag{1}$$

where the individual torque produced by each muscle-tendon unit (MTU) is calculated as $$M_j(t) = Fmt_j(t) rmt_j(t) \tag{2}$$

where $F_{mtj}(t) \in R$ (j=1, 2 represents the LGS and SOL muscles, respectively) denotes the individual contraction force applied on the corresponding MTU. It is represented as $$Fmt_j(t) = (Fce_j(t) + Fpe_j(t))\cos(\phi_j(t)) \tag{3}$$

where $\phi_j(t) \in R$ denotes the pennation angle that can be determined based on the method in [46]. $F_{cej}(t) \in R$ and $F_{pej}(t) \in R$ denote the corresponding forces generated by the parallelly located contractile element (CE) and passive element (PE) and can be calculated as [48], [49], [52]

$$\begin{bmatrix} Fce_j(t) \\ Fpe_j(t) \end{bmatrix} = \begin{bmatrix} F_j^{max} fl_j(lm_j(t)) fv_j(vm_j(t)) a_j(t) \\ F_j^{max} fp_j(lm_j(t)) \end{bmatrix} \tag{4}$$

where $$F_j^{max}$$

$\in R$ denotes the muscle contraction force at maximum volitional isometric contraction (MVIC), which can be referred from the literature [50], [53], [54] or identified based on an optimization algorithm in the HNM calibration procedures. $fl_j(lm_j(t))$, $fv_j(vm_j(t))$, and $fp_j(lm_j(t))$ denote the generic muscle contractile force-fascicle length, force-fascicle velocity, and passive elastic force-fascicle velocity curves, respectively. These curves were normalized to $$F_j^{max},$$

optimal fascicle length $$l_{mj}^0$$

$\in R$, and maximum fascicle contraction velocity $$V_{mj}^{max}$$

$\in R$. The values of $$l_{mj}^0$$

and $$V_{mj}^{max}$$

were fixed and reported by [53]. The explicit expressions of $fl_j(lm_j(t))$, $fv_j(v_m(t))$, and $fp_j(lm_j(t))$ can be found in [28], [35], [52], The CE length and velocity were determined by using data from OpenSim (National Institutes of Health for Biomedical Computation, Stanford, USA) [56] and the scaling method therein. For both the LGS and SOL muscles, a third-order polynomial relationship between the CE length and ankle joint position was built, as well as between the CE velocity and ankle joint velocity, according to the data from OpenSim. These two polynomial functions were used in the HNM to determine the CE length and velocity for either LGS or SOL muscle in real-time. $a_j(t) \in R$ denotes the muscle activation that will be derived by using the proposed sEMG-US imaging fusion subsequently.

In (2), $r_{mtj}(t) \in R$ represents the moment arm of each MTU and is calculated by using the musculoskeletal geometry model in FIG. 4. Consider the ankle joint dorsi-flexion/plantarflexion's rotation center in the sagittal plane as point O, the proximal and distal osteotendinous junction points of each MTU as $P_j$ and $Q_j$, and the angle between $O_{Pj}$ and $O_{Qj}$ as q(t). Then each MTU length, $I_{mtj}(t)R$, is represented as the distance between $P_j$ and $Q_j$ and calculated based on the law of cosines as $$lmt_j(t) = \sqrt{l_{OP_j}^2 + l_{OQ_j}^2 - 2lOP_j lOQ_j \cos(q(t))} \quad (5)$$

Where $I_{OPj} \in R$ and $I_{OQj} \in R$ represent the distance of $OP_j$ and $OQ_j$ in FIG. 2 that are obtained from OpenSim. By using the law of sines, we can derive $r_{mtj}(t)$ as $$rmt_j(t) = \frac{\partial lmt_j(t)}{\partial(q(t))} = \frac{2lOP_j lOQ_j \sin(q(t))}{lmt_j(t)} \quad (6)$$

Sequential Processing for the Muscle Activation Fusion

The objective of the sensor fusion is to obtain an estimation of muscle activation $a_j(t)$ in (4), noted as $\hat{a}_j(t)$, by combing the sEMG-derived muscle activation, a1, and the US imaging-derived muscle activation, a2. Our pilot disclosure in [35] investigated one possible way to fuse the muscle activation components from both sEMG and US imaging signals through adding an allocation ratio. The optimal al-location ratio was determined based on the HNM model calibration by using offline processed experimental data (with a lower sampling rate of 20 Hz). However, some challenges still remain to be solved, including 1) a generalized optimal allocation ratio for different participants, 2) online generation of US imaging-derived features, and 3) fusion of signals with asynchronous sampling rates. To address the above challenges, use of the subsequent stochastic approach to obtain the optimal estimation of muscle activation is provided herein. The discrete-time form of the 1st-order activation dynamics, shown in [57], can be written as $$a_j(t_{k+1}) = A_{j,k} a_j(t_k) + B_{j,k} u_j(t_k) + v_j^*(t_k) \quad (7)$$

where $A_{j,k}$, $B_{j,k}$, and $v_j^*(t_k) \in \mathbb{R}$ are calculated as, $$A_{j,k} = e^{-\frac{1}{Ta_j}(t_{k+1}-t_k)},\ B_{j,k} = 1 - e^{-\frac{1}{Ta_j}(t_{k+1}-t_k)},\text{ and}$$

$$v_j^*(t_k) = \int_{t_k}^{t_{k+1}} e^{-\frac{1}{Ta_j}(t_{k+1}-t_k)} vj(t)dt.$$

Figure 5:
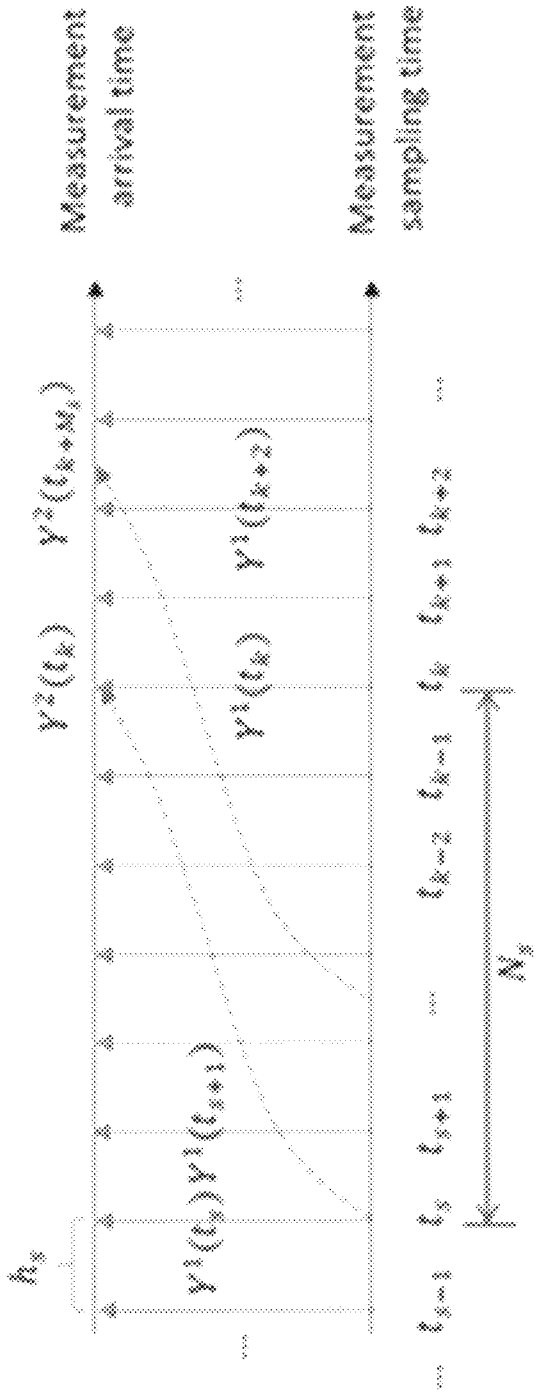
FIG. 5 is a schematic diagram according to implementations described herein.

Since the input of the muscle activation dynamics is from the central nervous system, which is very challenging to acquire directly, it is hypothesized that $u_j(t_k) \in R$ is an unknown input signal. $T_{aj} \in R^+$ is the time constant of each muscle activation, and $v_j(t) \in R$ is assumed to be an additive white Gaussian noise signal. The index j=1, 2 represents the LGS and SOL muscles, and the index k=1, 2, . . . represents the discrete sampling time instant. The high-sampled and low-sampled muscle activation signals measurements from sEMG and US imaging are depicted in FIG. 5. Referring now to FIG. 5, a schematic diagram depicting multi-rate and delayed muscle activation measurements from sEMG signals and US imaging is provided. The vertical lines represent the sEMG measurements, which are immediately available without considering delay, and the dashed lines represent the US imaging measurement that Here, $t_k$ is the current measurement instant, $t_s$ is the sampling instant for the US imaging measurement that is available at $t_k$, $h_s \in R+$ is the basic sampling interval, and $Y^1(t_k) \in R$ and $Y^2(t_k) \in R$ represent the sEMG-induced and US imaging-induced muscle activation measurements, respectively.

There exists a delay $N_s$ from the sampling instant $t_s \in R^+$ to the instant $t_k \in R^+$ when the US-derived measurement is available. The time instants when only sEMG signals are available and when both sEMG and US imaging signals are available are defined as the minor instance and major instance, respectively. The US imaging is sampled at a low rate, and the next sample is taken at $t_s+M_s$, where $M_s \in R^+$ is a constant number of intervals between two successive US imaging samples. Given the description above, the measurement models for sEMG signals and US imaging are presented as $$\begin{bmatrix} Y_j^1(t_k) \\ Y_j^2(t_k) \end{bmatrix} = \begin{bmatrix} a_j(t_k) + v_j^1(t_k) \\ a_j(t_s) + v_j^2(t_s),\ \text{if}\ k - s + N_s \end{bmatrix} \quad (8)$$

where Y1 and Y2 are the normalized measurements from the sEMG linear envelope and US imaging-derived echogenicity, respectively, which will be detailed below. The noise sources $v_j^*(t_k)$, $$v_j^1(t_k),$$

and $$v_j^2(t_s)$$

$\in R$ are assumed to be additive white Gaussian noise signals with respective covariance matrices $Q_j$, $$R_j^1,$$

and $$R_j^2$$

$\in R$. To fuse the multi-rate measurements with delays, a sequential processing scheme [58] was applied here. This sequential processing occurs whenever the individual measurement from either sEMG or US imaging is available. The measurements $$Y_j^1$$

$(t_k)$ are first processed by a Kalman filter. Starting with the filtered state estimate $$a^{\wedge}{}_j^1$$

$(t_k-1|t_k-1)$ and its error covariance matrix $$P_j^1$$

($t_k-1|t_k-1$), the state estimation at time $t_k$ is computed recursively as $$\hat{a}_j^1(t_k|t_{k-1}) = A_{j,k-1}\hat{a}_j^1(t_{k-1}|t_{k-1}) + B_{j,k}\hat{u}_j(t_{k-1}) \quad (9)$$

$$\hat{u}_j(t_k) = S_j(t_k)\left(Y_j^1(t_k) - \hat{a}_j^1(t_k|t_{k-1})\right) \quad (10)$$

$$\hat{a}_j^1(t_k|t_k) = \hat{a}_j^1(t_k|t_{k-1}) + K_j^1(t_k)\left(Y_j^1(t_k) - \hat{a}_j^1(t_k|t_{k-1})\right) \quad (11)$$

where $S_j(t_k)$ is an optimal gain that is calculated iteratively based on the approach mentioned in Section 4 of [59]. $K^1(t_k)$ R is the Kalman gain for sEMG measurement and is also calculated iteratively. At minor instances, only $$Y_j^1$$

($t_k$) are available, so the following can be set:

$$\hat{a}_j(t_k|t_k) = \hat{a}_j^1(t_k|t_k) \text{ and } P_j(t_k|t_k) = P_j^1(t_k|t_k)$$

For a linear system, the error covariance and the Kalman gain are only dependent on the variance of the error in the measurement and not on the measured value [58]. Therefore, even though the US imaging measurement $$Y_j^2$$

($t_k$) is not immediately available at time instant $t_k$, the error covariance and Kalman gain with respect to this measurement can still be updated as below as soon as the US imaging is sampled:

$$K_j^2(t_k) = P_j^1(t_k \mid t_k)\left[P_j^1(t_k \mid t_k) + R_j^2\right]^{-1}, \quad (12)$$

$$P_1^2(t_k \mid t_k) = \left[I - K_j^2(t_k)\right]P_j^1(t_k \mid t_k) \quad (13)$$

During the time period $t_s$ and $t_k$, since $Y^2(t_s)$ is not available, the state estimation continues to be updated by using only the sEMG measurements. At the major instance $t_{s+Ns}$, the US imaging measurements are available, and the correction term is added to the previous estimated state $\hat{a}_j(t_k|t_k)$ as $$\hat{a}_j(t_k|t_k) = \hat{a}_j^1(t_k|t_k) + \delta\hat{a}_j(t_k) \quad (14)$$

Where $\delta\hat{a}_j(t_k)$ is the correction term that is defined as $$\delta\hat{a}_j(t_k) = W_s K_j^2(t_s)\left(Y_j^2(t_k) - \hat{a}_j(t_s \mid t_{s-1})\right), \quad (15)$$

where Ws is an accumulated term that accounts for the delay and is calculated by $$W_s = \prod_{i=1}^{i=N_a}\left(I - K_j^*(s+i)\right)A_{j,s+1-1} \quad (16)$$

In (16), $$K_j^*$$

(t)∈R is used to distinguish it from $$K_j^1$$

(t)∈R, where t∈[$_{ts+1}$, $t_s+N_{s-1}$]. In other words, $$K_j^*$$

($t_k$)∈R is computed with the condition $P_j(t_k|t_k)$=

$$P_j^2$$

($t_k|t_k$), while $$K_j^1$$

($t_k$)∈R is computed with the condition Pj(tk|tk)=

$$P_j^1$$

($t_k|t_k$). Therefore, the muscle activation state estimates in the time interval [$t_{s+1}$, $t_{s+Ns-1}$] are sub-optimal, but the above correction (15) offers the optimal state estimates at the major instance. The convergence proof can be found in [58].

Assist-as-Needed Control Development

Figure 6:
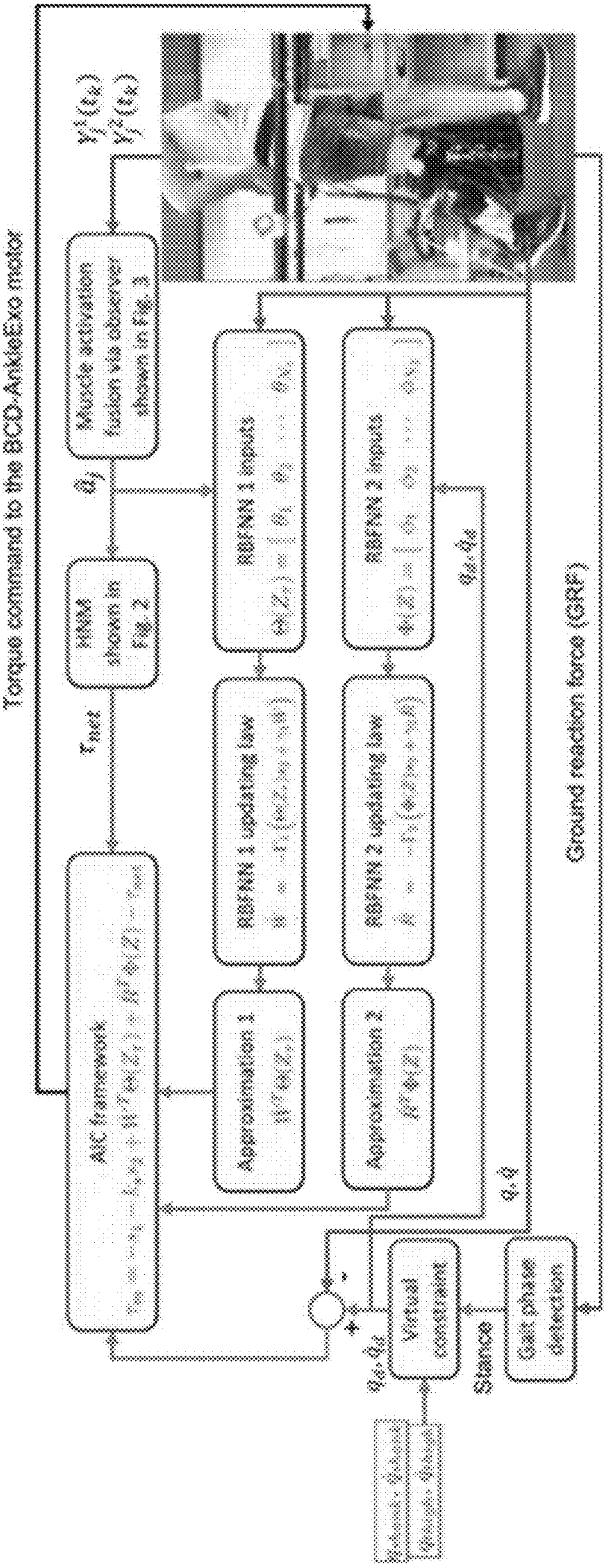
FIG. 6 is a schematic diagram according to implementations described herein.

FIG. 6 presents the overall diagram of the proposed AIC-based AAN control framework for the BCD-AnkleExo to provide plantarflexion assistance during the walking stance phase with the consideration of the ankle joint volitional effort that is predicted via the sEMG-US imaging-driven HNM. The red, blue, black lines with arrows represent the direct sensor measurements, the intermediate signals in the control system, and the torque command to the BCD-AnkleExo, respectively. The details for each component are given below.

System Dynamics and Impedance Matching Error

The dynamics of the ankle joint with the exoskeleton is given as $$J\ddot{q}(t) + C\dot{q}(t) + G(q(t)) + \int dis(t) = \tau_h(t) + \tau_m(t) \quad (17)$$

where q(t), q'(t), q"(t)∈R represent the angular position, velocity, and acceleration, respectively, of the ankle joint relative to the static standing posture. J, C, G R are the unknown system inertia, damping, and gravitational terms. $f_{dis}(t) \in R$ is the combination of the unknown external disturbances and the modeling uncertainties, including the Bowden cable friction, the impact with the environment, and so on. The variable $T_h(t) \in R$ is the voluntary plantarflexion torque exerted by the wearer, and $T_m(t) \in R$ is the applied assistance torque from the BCD-AnkleExo. To facilitate the controller design and stability analysis, the following assumptions are provided:

Assumption 1: The external disturbance and modeling uncertainties term $f_{dis}$ is uniformly upper bounded by $f \in R^+$, $\nabla^t \in [0,\infty)$.

Assumption 2: The unknown system inertia J is lower and upper bounded by $J \in R^+$ and $J \in R^+$, $\nabla t \in [0,\infty)$, respectively.

In general, the terms, J, C, and G of the overall dynamic system cannot be obtained accurately beforehand in actual applications. Thus, reference impedance parameters are introduced to the sole human ankle joint system as $$J_d\ddot{q} + C_d\dot{q} + K_d = \tau_h \tag{18}$$

where $J_d$, $C_d$, $K_d \in R^+$ are known reference inertia, damping, and stiffness coefficients of the ankle joint during the walking stance phase [60]. Define the error between the actual angular position and desired angular position as $e=q-q_d$, where $q_d \in R$ is continuously differentiable, bounded, and generated online based on the virtual constraints by using the shank and thigh orientations and angular velocities. Also, the first- and second-order time derivatives of $q_d$ are continuously differentiable and bounded. Using (18), the desired impedance model is equivalent to $$J_d\ddot{e} + C_d\dot{e} + K_de \triangleq \tau_h - J_d\ddot{q}_d - C_d\dot{q}_d - K_dq_d \tag{19}$$

In (19), the reference impedance model can be achieved (the right-hand side is equal to 0) if the real angular position q accurately tracks the desired impedance trajectory $q_d$. Therefore, the control objective here is to find an appropriate control input $T_m$ such that the ankle joint-ankle exoskeleton dynamics mentioned in (17) can precisely match the reference model dynamics in (19). Due to the fact that the human volitional effort $\tau_h$ can only be predicted from the HNM, noted as $\tau_{net}$, and because a difference exists between the system dynamics and the reference model dynamics, an impedance matching error can be introduced as $$\varepsilon = J_d\ddot{e} + C_d\dot{e} + K_de - \tau_{net} + J_d\ddot{q}_d + C_d\dot{q}_d + K_dq_d \tag{20}$$

where the control objective will be fulfilled when the impedance matching error meets $\varepsilon(t)=0$. Since $J_d$ is a positive constant, the newly augmented matching error can be written as $$\varepsilon_J = \ddot{e} + C_J\dot{e} + K_Je + K_\sigma\sigma \text{ where } \varepsilon_J = \frac{\varepsilon}{J_d},\ C_J = \frac{C_d}{J_d}, \tag{21}$$

$$K_J = \frac{K_d}{J_d},\ K_\sigma = \frac{1}{J_d}, \text{ and } \sigma = J_d\ddot{q}_d + C_d\dot{q}_d - \tau_{net}$$

Selecting two positive constants α and β that satisfy the conditions CJ=α+β and KJ=αβ, the augmented matching error is rewritten as $$\varepsilon_J = \ddot{e} + (\alpha+\beta)\dot{e} + \alpha\beta e + \dot{\eta} + \alpha\eta \tag{22}$$

where η is elaborately selected to satisfy the condition that $K_\sigma\sigma=\eta'+\alpha\eta$. In addition, by defining a filtered matching error term $r=e'+\beta e+\eta$, the augmented matching error can be rewritten as $$\varepsilon_J = \dot{r} + \alpha r \tag{23}$$

Neural Networks-Based Controller Development

The overall system dynamics given in (17) can be written in a state-space form as $$\begin{bmatrix}\dot{x}_1\\ \dot{x}_2\end{bmatrix} = \begin{bmatrix} x_2 \\ \left(\tau_h + \tau_m - Cx_2 - G - \int dis\right)/J\end{bmatrix} \tag{24}$$

where $[x_1\ x_2]^T=[q,\ q']^T$. Defining $q'_s=q'_d$ ße η, the following is provided: $q''_s=q''_d$ ße'η'. Considering that r=e'+ße+η, the following is obtained $q'_s=q'r$, which implies $q''_s=q''\ r''$. To facilitate the stability analysis, variables are defined as $s_1=x_1\ q_d=e$, $s_2=x_2\ q'_s$. Since only one degree of freedom exists in the targeted system, $q_s \in R$, $s_1 \in R$, and $s_2 \in R$. By taking the time derivatives of $s_1$ and $s_2$, the following is provided:

$$\begin{bmatrix}\dot{s}_1\\ \dot{s}_2\end{bmatrix} = \begin{bmatrix} s_2 - \beta e - \eta \\ \left(\tau_h + \tau_m - Cx_2 - G - \int dis\right)/J - \ddot{q}_s\end{bmatrix} \tag{25}$$

Considering the error between the ankle joint torque estimation $r_{net}$ from the sEMG-US imaging-driven HNM and the actual exact torque rh in (17), the following is defined: $\tau=\tau_{net}\ \tau_h$, which is unknown. In addition, the external disturbance and ankle exoskeleton dynamics are also unknown. Inspired by [21], [27], two Gaussian radial basis function neural networks (GRBFNNs) are exploited to represent these two unknown functions as $$\Delta\tau = W^{*T}\theta(Z_\tau) + \epsilon_\tau \tag{26}$$

$$C_{s2} + C\dot{q}_s + G(x_1) + J\ddot{q}_s = R^{*T}\phi(Z) + \epsilon_e \tag{27}$$

where $W^* \in R^{N_1}$ and $R^* \in R^{N_2}$ are optimal weights for the two NNs and $N_1$ and $N_2$ are the number of neurons in the hidden layers. $\Theta(Z_\tau)$: $R^5 \rightarrow R^{N_1}$ and $\phi(Z)$: $R^6 \rightarrow R^{N_2}$ are the basis function matrices of the two NNs, and $\epsilon \in R$ and $\epsilon_e$ R are approximation errors of the two NNs, which are upper bounded by positive constants that can be written as $\epsilon_\tau\ \bar{\epsilon}_T$ and $\epsilon_e\ \bar{\epsilon}_e$. The augmented input vectors for the two NNs are defined as $Z_\tau=[1,\ x_1,\ x_2,$ $\hat{\alpha}_1$, $\hat{\alpha}_2]^T$ and $Z=[1, x_1, x_2, q_s, q'_s, q''_S]^T$. The Gaussian radial basis functions of $\odot(Z_T)$ and $\phi(Z)$ are defined as $$\theta_{n1} = e^{-\frac{\left\|z_\tau - \mu_{n_1}^1\right\|^2}{2\delta_1^2}}, \phi_{n2} = e^{-\frac{\left\|z - \mu_{n_2}^2\right\|^2}{2\delta_2^2}} \tag{28}$$

Where $$\mu_{n1}^1$$

$\in R^5$ ($n_1=1, 2, \ldots, N_1$) and $$\mu_{n2}^2$$

$\in R^6$ ($n_2=1, 2, \ldots, N_2$) are the centers of the $$n_1^{th}$$

or $$n_2^{th}$$

RBF.

With respect to the elements in $Z_\tau$ or Z. $Z_\tau$ and Z are the current state variables in the augmented input vectors, and $\delta_1$ and $\delta_2$ are scalar smoothing constants that determine the width of the basis functions. The number of basis functions and the values of $\delta_1$ and $\delta_2$ will be chosen experimentally to provide the best possible trade-off between the precision of the approximation and the computational complexity of the proposed controller. Therefore, the matrices of all radial basis functions for the two NNs are defined as $$(Z_\tau) = [\theta_1 \theta_2 \ \ldots \ \theta_{N1}]^T, (Z) = [\phi_1 \phi_2 \ \ldots \ \phi_{N2}]^T \tag{29}$$

Based on the GRBFNNs, the unknown volitional net plantarflexion torque prediction error can be approximated as $\hat{W}^T \odot(Z_\tau)$, while the external disturbance and exoskeleton dynamics can be approximated as $\hat{R}^T\phi(Z)$. The vectors $\hat{W}$ and $\hat{R}$ are the estimates of the optimal weights for the NNs in (26) and (27), and their updating laws are designed as $$\dot{\hat{W}} = -\Gamma_1\left(\theta(Z_\tau)s_2 + \gamma_1 \hat{W}\right), \dot{\hat{R}} = -\Gamma_2\left(\phi(Z)s_2 + \gamma_2 \hat{R}\right) \tag{30}$$

where $\gamma_1$ and $\gamma_2$ are small positive gains and $\Gamma_1 \in R^{N_1 \times N_1}$ and $\Gamma_2 \in R^{N_2 \times N_2}$ are symmetric positive definite matrices. The first term on the right-hand side (RHS) of either or $\hat{\dot{R}}$ tends to reduce the tracking error and is a typical adaptive control term in which $\Gamma_1$ or $\Gamma_2$ determines the overall tracking error-based adaption rate. The second term on the RHS of either W' or R tends to reduce the control input and preserve the system information learned from the previous motion cycle, which is essential for repeated movement of the ankle joint during walking. The optimal weights' estimation errors are defined as $\tilde{W}=\hat{W}-W^*$and $\tilde{R}=\hat{R}-R^*$, which need to be bounded during the impedance control implementation. The updating laws proposed in (30) are supposed to achieve a decrease of the torque applied by the ankle exoskeleton when the wearer is able to complete the ankle joint movement during walking, and vice versa. The overall AAN control law (in FIG. 6) for achieving zero error between the ankle exoskeleton dynamics and the human ankle joint desired impedance model is given as $$\tau_m = -s_1 - k_s s_2 + \hat{W}^T \theta(Z_\tau) + \hat{R}^T \phi(Z) - \tau_{net} \tag{31}$$

Experimental Results

The treadmill walking experimental disclosure was approved by the Institutional Review Board (IRB) at North Carolina State University (IRB approval number: 20602). Five young participants (identified as: A01, A02, . . . , A05, 3M/2F, age: 25.4±3.1 years, height: 1.77±0.10 m, mass: 78.0±21.1 kg) with no neurological disabilities were included to conduct walking experiments at 0.60 m/s on an instrumented treadmill when wearing the designed BCD-AnkleExo. Participants signed a written informed consent form prior to the experimental sessions. The entire disclosure included three different scenarios that are detailed below for each participant. During each scenario, the participants were asked to walk for three minutes with the first two minutes as an acclimation procedure, and the last one minute for data collection, which was used for results presentation and analysis in Embodiments of the present disclosure. BCD-AnkleExo with the setting of zero impedance control.

Scenario 1 (S1): Treadmill walking task while wearing the BCD-AnkleExo with the setting of zero impedance control mode. Scenario 2 (S2): Treadmill walking task while wearing the BCD-AnkleExo in the AIC mode with only sEMG-based ankle joint effort prediction. Scenario 3 (S3): The similar procedures as S2 but in the proposed AIC with sEMG-US imaging-based ankle joint effort prediction. During the treadmill walking experiments, in addition to the BCD-AnkleExo (details of the mechatronic design and benchtop testings can be seen in Appendix C), 28 reflective markers (Vicon Motion System Ltd, Los Angeles, CA, USA) were placed on the lower limbs and pelvis for the measurements of 3D coordinates of each segment at 100 Hz that were used for offline ID calculation. The ground reaction force (GRF) signals from two force plates (Bertec, Columbus, OH, USA) mounted beneath the split treadmill belts were also collected at 1000 Hz for offline ID calculation. Furthermore, a threshold (5% of the z-axis GRF signal) was selected to differentiate the stance and swing phases in real-time on both legs during each gait cycle, which was used to switch between two controllers, i.e., the AIC during the stance phase and a traditional proportional-derivative controller for regulating the dorsiflexion motion during the swing phase. In Embodiments of the present disclosure, only results from the stance phase are presented. Two sEMG sensors (Bagnoli™ Desktop, DELSYS, MA, USA) were attached onto both the LGS and SOL muscles to measure the corresponding sEMG signals at 1000 Hz. A linear US transducer (38 mm of length, 6.4 MHz center frequency, L7.5SC Prodigy Probe, S-Sharp, Taiwan) was cross-sectionally attached to the location next to the sEMG sensor for LGS muscle to image both superficial LGS and deep SOL muscles in the same plane. sEMG signals were first band-pass filtered with a bandwidth between 20 Hz and 450 Hz, full-wave rectified and low-pass filtered with a cut-off frequency of 6 Hz, and then normalized to the peak value at the MVIC. After obtaining the normalized linear envelope, denoted as $N_j(t_k)$, a second-order recursive filter was used to calculate the neural activation of each muscle, denoted as $u_j(t_k)$, which is given by $$u_j(t_k) = \alpha_0 N_j(t_k - \tau_j) - \beta_1 u_j(t_k - 1) - \beta_2 u_j(t_k - 2),$$

where $\alpha_0$=0.9486, $\beta_1$=−0.056, and $\beta_2$=0.000627 [50]. $\tau_j$ is the EMD and is usually between 30 ms and 120 ms. Finally, a nonlinear relationship between the neural activation $N_j(t_k)$ and the corresponding muscle activation, denoted as $$Y_j^1$$

($t_k$) above is given as [50]

$$Y_j^1(t_k) = \frac{e^{A_j N_j(t_k)} - 1}{e^{A_j - 1}}$$

where $A_j$ represents the nonlinear shape factor for each muscle, which is allowed to vary between −3 and 0, with $A_j$=0 being a linear relationship. The US echogenicity signals of LGS and SOL muscles at each available time instant $t_k$ are calculated as $$\text{Echo}_j(t_k) = \frac{1}{N_A N_L} \sum_{x=1}^{N_A} \sum_{y=1}^{N_L} I_{j,t_k}(x, y) \tag{32}$$

where $N_A$, $N_L \in R^+$ represent the pixel numbers along axial and lateral directions, respectively. $I_{j,tk}(x,y) \in R$ represents the US intensity information at the pixel location (x,y) in the region of interest from the logarithmically compressed imaging signals after the beamforming procedure. Due to the pixel displacement tracking-free nature of the US echogenicity signal, it is the most feasible US imaging-derived feature for online feedback and implementation in the closed-loop control problem. Visually, the echogenicity signal reflects the overall brightness change of the muscle's region of interest, which linearly correlates with the muscle contraction level [36], [42]. Similarly, the US echogenicity signals from (32) were also normalized to the values between no contraction and MVIC to calculate the US imaging-induced muscle activation, denoted as $$Y_j^2$$

($t_k$) discussed herein. Prior tests showed that the transfer rate of the real-time US echogenicity data from the US machine to the host computer running the control algorithm was around 7.8 frames per second. This implied that the US imaging-derived muscle activation measurement sampling rate was significantly lower than the sampling rates of other sensing channels for a real-time control purpose, which was addressed by using the sequential processing algorithm described herein.

Figure 7:
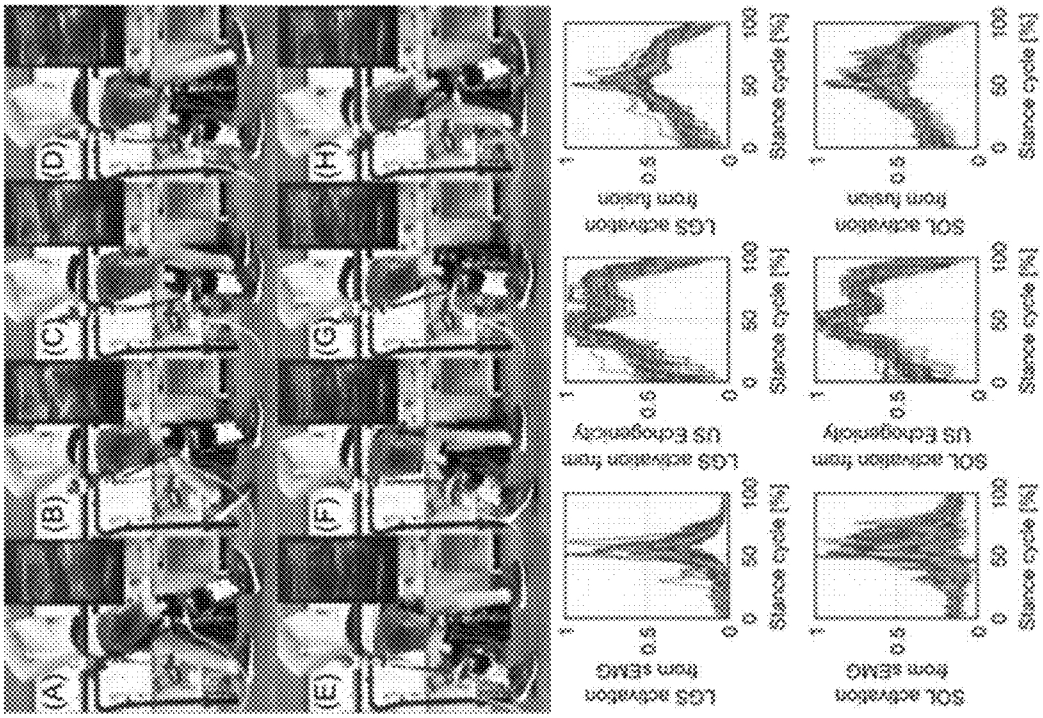
FIG. 7 is a schematic diagram according to implementations described herein.

Treadmill Walking Experimental Results—Validation of the Sensor Fusion on the Ankle Joint Volitional Effort Prediction The snapshots of treadmill walking experiments on one representative participant in S1 are shown on the top of FIG. 7 with a sequence from (A) to (H), where each gait cycle was defined between the current and next heel-strike instants based on the real-time GRF measurements. Readers can find more intuitive demonstrations when referring to the supplementary videos. During the demonstrated gait cycle, the corresponding brightness mode (B-mode) US image sequences of both LGS and SOL muscles are plotted on the right side of each snapshot, and the echogenicity changes of both muscles are visualized during the stance phase. On the bottom of FIG. 7, the left column, middle column, and right column plots show the sEMG-derived muscle activation, US echogenicity-derived muscle activation, and muscle activation fusion from both LGS and SOL muscles during the walking stance phases within the last minute, respectively. The x-axis from each plot is normalized between 0% and 100% to represent the time instants of heel-strike and toe-off, namely stance phase/cycle. Recalling the net plantarflexion torque during the walking stance phase in [61], the change of either sEMG profiles or US echogenicity signals highly correlates to the ankle joint biological torque change during the stance phase, so the normalization of both sEMG profiles and echogenicity signals from both muscles with respect to the values at MVIC were used in the muscle activation fusion.

Figure 8:
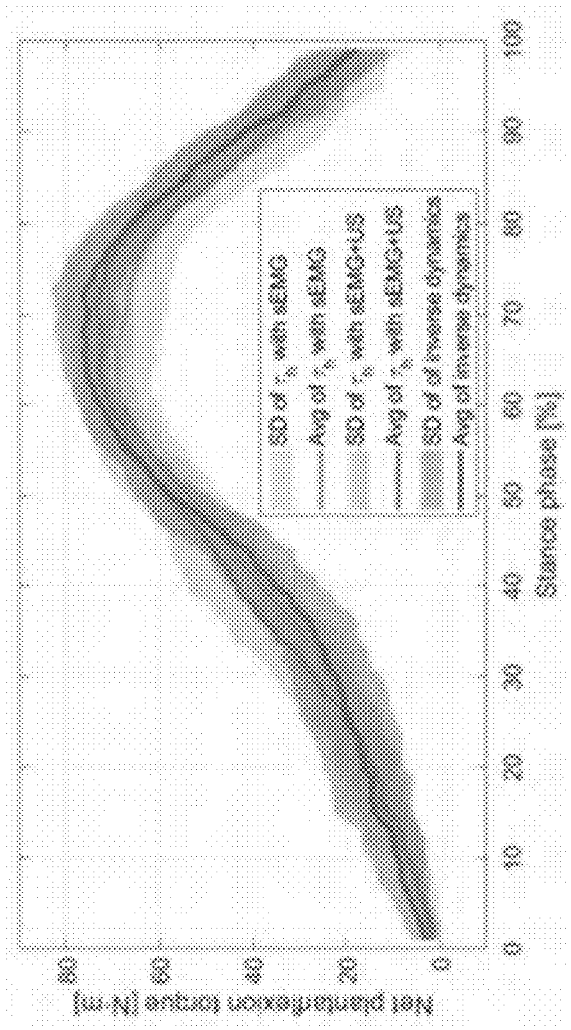
FIG. 8 is a schematic diagram according to implementations described herein.

The direct benefit of fusing both sEMG- and US imaging-derived muscle activation signals is the higher volitional plantarflexion torque prediction accuracy. According to the treadmill walking experimental results, this benefit holds for all three scenarios and was evaluated by comparing the net plantarflexion torque prediction errors by using sEMG- and sEMG-US imaging-driven HNMs. Corresponding to the muscle activation level calculations from the neuromuscular measurements in FIG. 7, the net plantarflexion torque prediction and benchmark results are presented in FIG. 8. The benchmark results were calculated based on the ID algorithm in Visual 3D software (C-Motion, Rockville, MD, USA) given the coordinates of markers on lower extremities and GRF data. More details of the HNMs' calibration can be found in the model calibration and validation section in [46]. Considering the root mean square error (RMSE) between torque prediction and benchmark during each stance cycle as an individual evaluation metric, the RMSE values as shown in FIG. 8 are 14.32±5.99 N·m and 9.74±4.45 N·m across all stance cycles when using the sEMG- and sEMG-US imaging-driven HNMs, respectively. The averaged prediction error of the proposed HNM, when normalized to the peak value of the benchmark torque according to the ID (106.55 N·m), is around 9.2%. Similar results were observed for all three scenarios from five participants, and net plantarflexion torque prediction RMSE values are summarized and compared in FIG. 41. Except for S2 and S3 on A03 and S2 on A04, the torque prediction RMSE was significantly reduced by using the proposed sEMG-US imaging-driven HNM compared to the sEMG-driven HNM.

While the main outcomes in the current disclosure focused on the treadmill walking experiments at a speed of 0.60 m/s, the human volitional effort (net plantarflexion torque during the walking stance phase) prediction performance of the proposed sEMG-US imaging-driven HNM in treadmill walking experiments was examined at multiple higher walking speeds, including 0.75 m/s, 1.00 m/s, and 1.25 m/s. The representative results from participant A03 in S1 are demonstrated in FIG. 7, where blue/red solid curves and shadowed areas represent the mean and standard deviation (SD) values across multiple stance cycles within in one minute from the HNM-based prediction/ID-based calculation. The averaged prediction error normalization values are 9.1%, 8.3%, 10.3%, and 8.9%, respectively, for these four investigated speeds, which indicates that the proposed sEMG-US imaging-driven HNM achieved a good prediction performance that followed the demand for volitional net plantarflexion torque.

Outcomes with and without AIC Frameworks

To facilitate the reproduction of these results, the necessary design parameters and control gains are summarized in FIG. 42.

Figure 9:
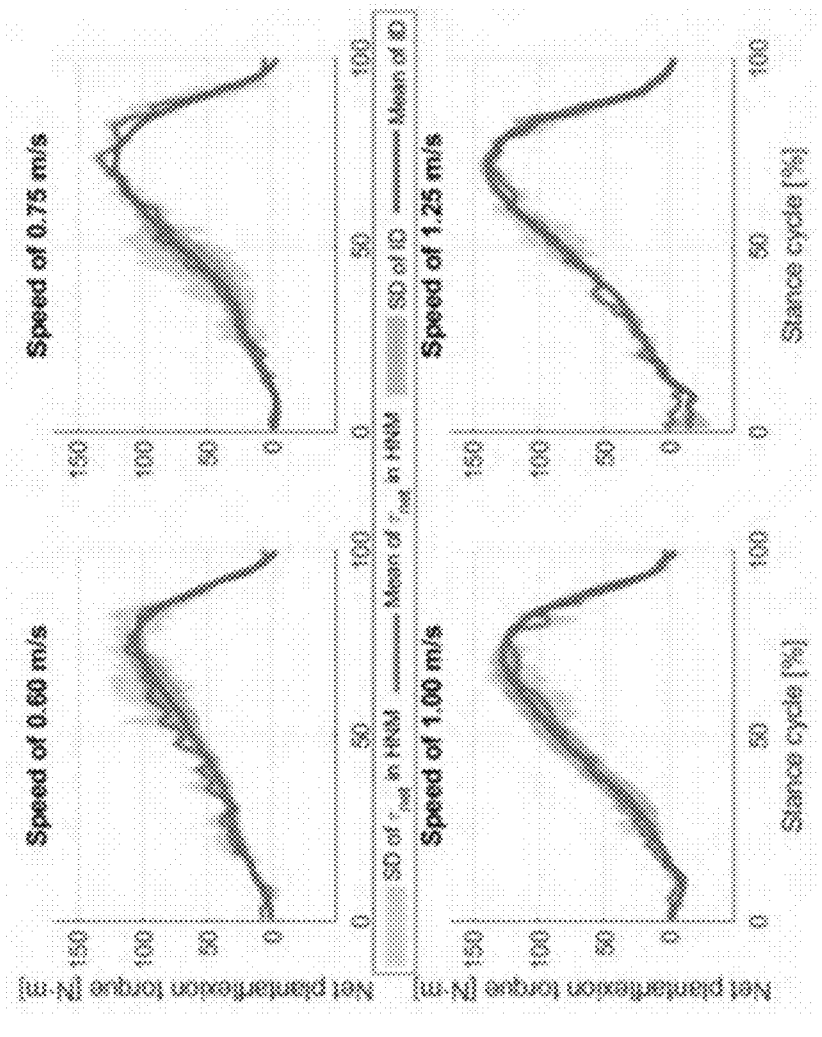
FIG. 9 is a schematic diagram according to implementations described herein.

To guarantee the success and effectiveness of the NN-based AIC design, one necessary assumption is that the estimations of the NN weight vectors will converge within a finite time. Taking the experimental results in S3 as an example, FIG. 10A-E shows the convergence of W and R in (30) during each stance cycle for each participant, which indicates almost all elements in the two weight vectors converge to corresponding stable values within the recorded one minute. In addition, stable values for elements from W^ are relatively close to each other, while the majority of elements from R^ converge to somewhere close to zero. The top plots in FIG. 9 shows the ankle joint trajectory tracking performance during the walking stance phase with the proposed AIC framework in S3 (embedded with the sEMG-US imaging-driven HNM for net plantarflexion torque prediction). The sequential data of both desired (red dashed curves) and actual (blue solid curves) ankle joint trajectories are from ten consecutive stance cycles out of the one-minute data collection on the participant A02. Additionally, corresponding to each stance phase, the net plantarflexion torque prediction via the sEMG-US imaging-driven HNM and the assistance torque from the BCD-AnkleExo are presented on the bottom of FIG. 9. These results indicate that the proposed AAN control framework achieved a good trajectory tracking performance, a stable net plantarflexion torque prediction performance, and an adaptive assistance level from the BCD-AnkleExo (the torque assistance profile changes in response to the torque prediction and joint angle trajectory tracking error). Across all stance cycles in the second minute under S3, the ankle joint trajectory tracking RMSE is 4.76±0.42°, which is acceptable since the eventual control objective of the AIC is to achieve a more natural behavior of the ankle exoskeleton instead of minimizing the trajectory tracking error. Instead of using a pre-defined fixed assistance torque profile like in [44], the assistance torque from the BCD-AnkleExo in this disclosure is generated automatically from the AIC framework within each stance cycle, and it is time-varying during different gait cycles, which is more adaptive to variations in gait pattern and ankle joint volitional effort. The peak assistance torque appeared between 60-70% of the stance cycle, which is nearly consistent with the peak voluntary plantarflexion torque prediction.

Figure 12A:
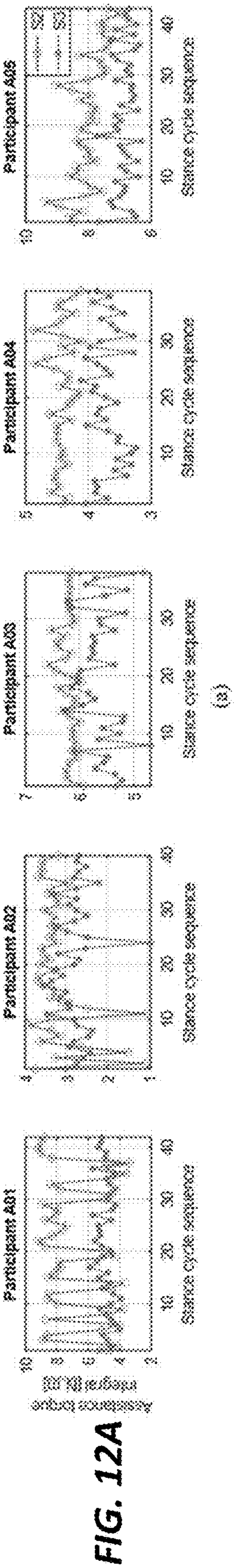
FIGS. 12A and 12B are schematic diagrams according to implementations described herein.
Figure 12B:
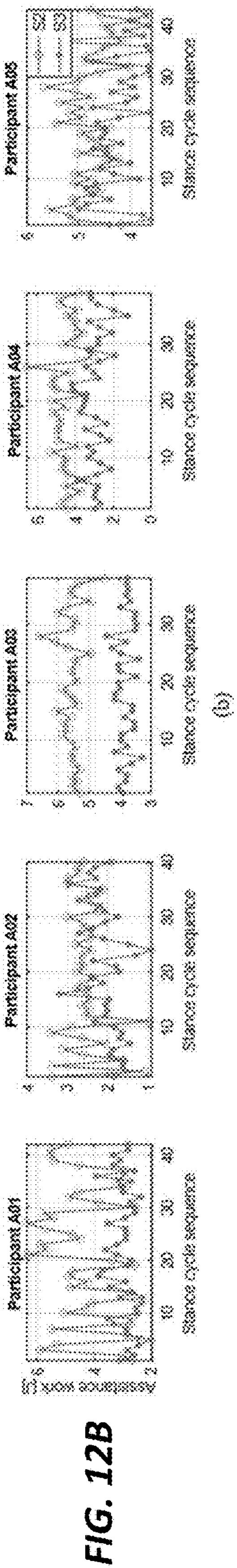
Figure 13A:
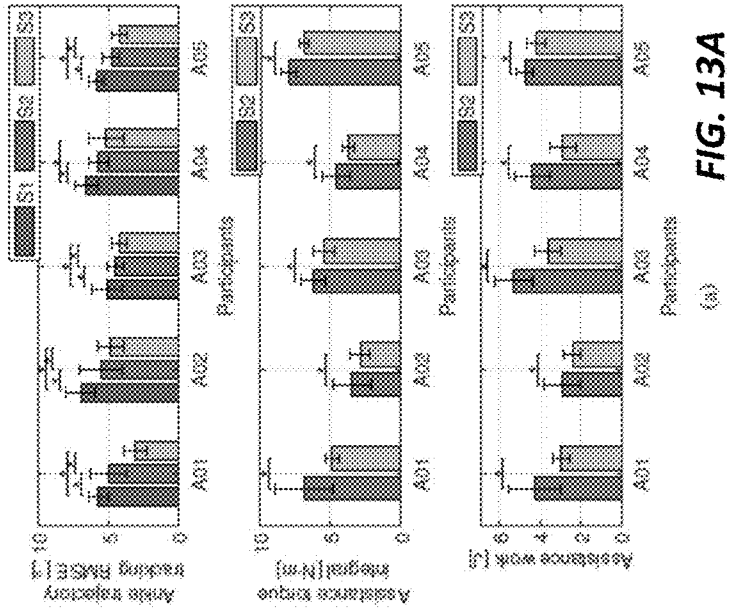
FIGS. 13A and 13B are schematic diagrams according to implementations described herein.
Figure 13B:
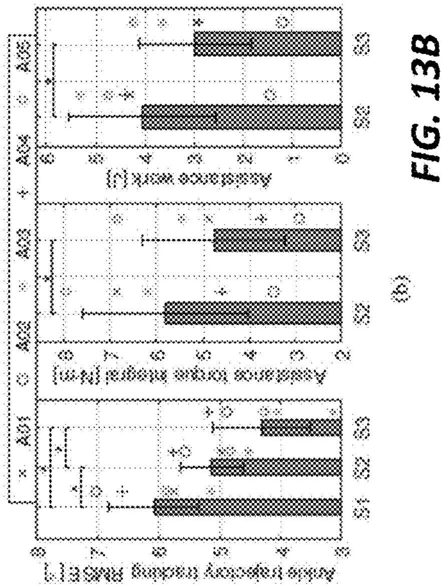

To evaluate the control performance between the proposed and traditional AIC frameworks (an sEMG-driven HNM was adopted to predict the volitional plantarflexion effort in the traditional AIC framework), metrics during each stance cycle including trajectory tracking RMSE value, assistance torque integral, and overall assistance work were calculated and compared based on the results in S2 and S3. FIG. 12A and FIG. 12B show the assistance torque integral and overall assistance work of each stance cycle during the last minute from all participants. The two metrics for evaluating the injected energy from the ankle exoskeleton in FIG. 12A and FIG. 12B indicate that the assistance during the treadmill walking stance phase was reduced for all participants when the AIC framework was incorporated with the sEMG-US imaging-driven HNM. From the individual perspective, the mean and SD values of the assistance torque integral and overall assistance work among all recorded stance cycles are presented in the middle and bottom plots of FIG. 13A, while the mean and SD values of the trajectory tracking RMSE values in all three scenarios are shown in the top plot of FIG. 13A. The blue, orange, and yellow bars represent the corresponding metrics' mean values under S1, S2, and S3, respectively, while the error bars represent the SD values. It should be noted that the injected assistance metrics in S1 are not shown in FIG. 13A due to the fact that zero impedance would provide minimal assistance and so can be neglected in the current work. FIG. 13B summarizes the inter-participant results that correspond to the individual results in FIG. 13A in each scenario, where the scattered points represent the mean values of each metric on individual participants across all stance cycles, and the bar plots represent the mean and SD values of each metric across all five participants. The results of a Shapiro-Wilk parametric hypothesis test showed the normal distribution of each metric group across all stance cycles on each participant and across participants (known as inter-participant) shown in FIG. 13A. A one-way repeated-measure analysis of variance (ANOVA) and a post-hoc Tukey's honestly significant difference test (Tukey's HSD) were used to determine if there was any significant difference among the RMSE values in these three scenarios on each participant and across participants. The results in FIG. 13A show that both AIC frameworks significantly reduced the ankle trajectory tracking RMSE compared with S1 on each participant. Additionally, the AIC framework in S3 significantly outperforms the AIC framework in S2 in terms of the trajectory tracking RMSE on all participants except for A04 (p-value=2.18e−7, 7.21e−3, 2.88e−2, 5.60e−2, and 4.63e−3 for A01, A02, . . . , A05). Across all five participants, FIG. 13B shows the proposed AIC frameworks in S3 and S2 significantly reduced the trajectory tracking RMSE during the stance phase by 28.42% (p-value <0.01) and 15.56% (p-value <0.05), respectively, when compared to results in S1. Additionally, the proposed AIC framework in S3 significantly reduced the ankle joint trajectory tracking RMSE by 15.23% (p-value <0.05) compared to the AIC framework in S2.

Furthermore, the experimental results in FIG. 13A show that the AIC framework in S3 significantly reduced the assistance torque integral (p-value=2.56e−8, 2.87e−4, 4.15e−12, 6.17e−19, and 1.02e−15 for A01, A02, . . . , A05) and overall assistance work (p-value=1.62e−8, 5.00e−3, 2.68e−23, 5.14e−15, and 6.28e−7 for A01, A02, . . . , A05) from the individual perspective compared to results in S2. Across all five participants, FIG. 13B shows the proposed AIC framework in S3 significantly reduced the assistance torque integral and overall assistance work by 18.08% (p-value <0.01) and 25.48% (p-value <0.01), respectively. The asterisk in FIG. 13 represents the statistically significant difference at a 95% conference level.

Rehabilitative or assistive devices can achieve a more intuitive and transparent control when applying an AAN control framework. In addition, AAN control can also encourage the wearers to actively participate in rehabilitation procedures, which is likely to maximize training benefits. The accurate determination of human joint motion intent or residual effort is essential for AAN control development. In embodiments of the present disclosure propose use of an sEMG-US imaging-driven HNM, a biological HMI that fuses neuromuscular signals from both sEMG and US imaging to predict human ankle joint volitional effort. This new HNM is then incorporated into an NN-based AIC framework to achieve the AAN control objective of a BCD-AnkleExo, which automatically adjusted the assistance torque from the ankle exoskeleton. The system's mechatronic performance and the controller's effectiveness were validated through treadmill walking experiments at 0.60 m/s on five participants with no neurological disabilities.

Given the targeted users of the BCD-AnkleExo are individuals with residual voluntary motor control, effective controller development needs to take the human motion intent/volitional effort into consideration. Although simpler controllers that do not consider sEMG, US, HNM, or NN could estimate human motion intent by measuring mechanically intrinsic signals, including the joint angles, impedance, gait events, interaction dynamics, or estimate the joint torque from ID [35], [62]-[64], these mechanically intrinsic measurements are the outcomes of physical motion, which are prone to mechanical delays and may not be appropriate in some cases, as the users must produce a torque on the joints above some threshold to initiate the motion before the de-vices can generate assistance. Compared to the mechanically intrinsic measurements, one of the main advantages of using biological signals to estimate the motion intent/volitional effort is the time lag (between 30 ms to 150 ms in [42], [50], [65]-[67]) between the signal generation and joint motion execution, which enables the human intent-based control of wearable robotic devices. Specifically, the control command generation of the robotic devices advances the generation of the human joint torque or limb motion. Therefore, biological signals, especially sEMG signals, have been successfully applied in robotic devices control in the past, like examples being in [19], [24], [68]-[71]. The crucial perspective of the biological signals-based control approaches is that even if the users are not capable of producing sufficient joint motion or joint torque, the motion intent of the human user can still be detected and consequently the wearable robotic devices can be controlled.

What does the additional complexity of adding US imaging in addition to sEMG add to one or the other one alone? In the current disclosure, the US imaging was not used to track the contractile element length or velocity in real-time due to the computationally-intensive image processing procedures, which would significantly lower the sampling rate of US imaging-derived signal feedback. Instead, the echogenicity signal from US imaging was used to represent and refine the sEMG-derived muscle activation levels. In various examples, both signals provide complementary information, which is beneficial to the joint torque or motion prediction accuracy improvement. Improvement ranges have been demonstrated, e.g., from 14% to 48% and from 28% to 54% when compared to the usage of sole sEMG or sole US imaging signals, respectively. An sEMG signal and a US imaging signal are both indirect measures of descending neural signals from the CNS. Specifically, sEMG signals measure electrical potentials generated by muscle motor units when they are neurally activated, and the amplitude of a filtered and rectified sEMG signal linearly correlates with the number of firing motor units, which offers a physical measurement of the microphysiological response [72]. Meanwhile, US imaging signals show visualized 2D information of the macro-physiological response [73] of a targeted muscle caused by the same group of motor units firing.

Figure 14:
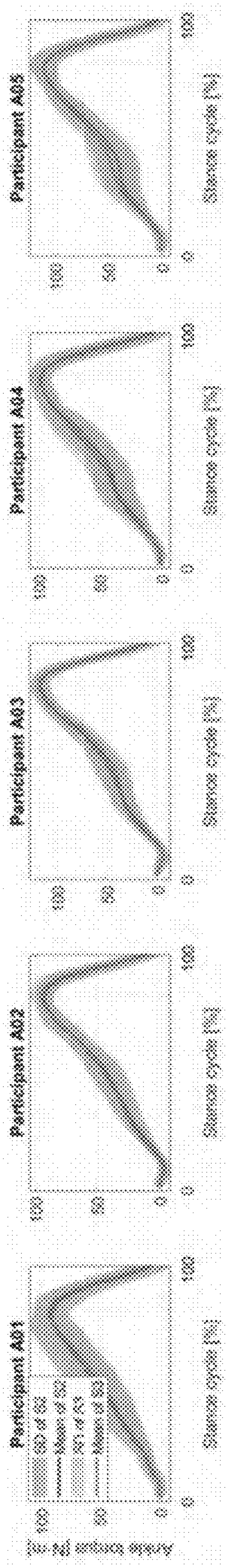
FIG. 14 is a schematic diagram according to implementations described herein.

Therefore, sEMG- and US imaging-derived signals provide the information from an electrical aspect and a mechanical aspect, respectively, with respect to the same physiological stimulus. Furthermore, the US echogenicity signals could provide both superficial (LGS) and deep (SOL) muscles' activation information in the same image plane on the same transducer location with less interference from adjacent muscles, while sEMG sensors would need to be placed on different locations for collecting signals from LGS and SOL muscles. The combination between sEMG and US echogenicity signals could 1) mitigate any cross-talking or interference effect from neighboring sEMG signals and 2) lower the echogenicity signals drift caused by the accumulated pixel motion and muscle tissue deformation. The results from three scenarios demonstrated the superior performance of the proposed AAN control framework with volitional ankle joint effort prediction through the sEMG-US imaging-driven HNM, including ankle joint volitional effort prediction error reduction, trajectory tracking error reduction, and assistance torque integral and overall assistance work reduction. Although the desired ankle joint trajectory during the stance phase was generated online through virtual constraints and varied with gait cycles and across participants due to the variations of the thigh and shank orientations and velocities, the AAN control framework maintained a relatively small trajectory tracking RMSE while providing compliant plantarflexion assistance from the exoskeleton. In addition, the volitional plantarflexion moment prediction via either the sEMG-driven or sEMG-US imaging-driven HNMs varied along with gait cycles and across participants due to the variations of sEMG and US imaging signals, but the AIC effectively regulated the assistance torque without causing discomfort to the wearers. In this disclosure, since participants were asked to walk on the treadmill at 0.60 m/s when wearing the BCD-AnkleExo that provided plantarflexion assistance in S2 and S3, it is hypothesized that there was no obvious ankle joint torque change of the overall system due to the consistent walking speed and rhythm. By comparing the net plantarflexion torque calculated from ID in S2 and S3, a significant difference (the relative change was under 5% of peak torque value) was not observed. The results from FIG. 13A-B indicate the injected torque from the BCD-AnkleExo was reduced by using the proposed AIC framework in S3 compared to the AIC framework in S2. According to the ankle joint overall net plantarflexion torque from ID, as shown in FIG. 14, the Pear-son correlation coefficient (PCC) values between ankle joint trajectories within corresponding stance cycles under both S2 and S3 were calculated with the mean and SD values of 0.967 0.032, 0.985 0.010, 0.987 0.011, 0.977 0.016, and 0.974 0.023 for participants A01, A02, A03, A04, and A05, respectively. From these high PCC values, it was observed that the overall torque remained invariant although the assistance strategies were set different between S2 and S3. Therefore, by subtracting the injected torque from the overall torque, the biological torque on the ankle joint volitionally generated by the participants was increased, which supported the objective of encouraging and boosting the active involvement/muscle contraction from the participants using the exoskeleton. Although these results were observed from participants without neurological disorders, they are promising and potentially translatable to people with weakened plantarflexion functions. Despite promising results, more improvements and investigations will be of interest in future work. For ex-ample, in our current BCD-AnkleExo design, due to the space limitation on the end-effector and the application of a commercial SEA module, the assistance torque measurement was not directly measured on the ankle joint since no force or torque sensors, as mentioned in [9], [10], [74], were installed between the cable output side and the end-effector. Instead, a transmission model was developed to calculate the output torque on the distal cable end, as mentioned in Appendix C. However, the transmission modeling accuracy may be compromised by many unexpected factors like the cable bending angle, the sliding of the exoskeleton attachment position, and nonlinear friction. Additionally, the time-invariant reference impedance parameters referred from [60] were selected during the stance phase to simplify the AIC development and facilitate the walking task application. However, a more accurate physiologically inspired ankle exoskeleton impedance control approach should consider the time-varying properties of reference impedance parameters to accomplish a more natural walking gait pattern. Furthermore, as shown in FIG. 13A-B, the reduction of the assistance torque integral along with individual stance phase duration by using the proposed AAN control framework may indicate that the undesired human-machine-interaction was mitigated and thus the volitional effort from the ankle joint was boosted, which needs more investigation. There are still some limitations in the current disclosure. First of all, from the hardware design perspective, the BCD-AnkleExo was designed to be an portable assistive device (with lower assistance torque magnitude due to the selection of a low-power actuation module) to provide a supplementary torque upon the existing residual volitional ankle joint torque, so the BCD-AnkleExo was not able to reproduce the same torque command as the biological torque on the ankle joint during walking, like these designs in [74], [75]. As introduced in the BCD-AnkleExo hardware design and benchtop testing section, the peak output torque from the actuator module is 38 N m. With the consideration of the energy ratio through the Bowden cable transmission over a certain distance, the real assistance torque applied on the ankle joint is saturated at 25 N m. Secondly, given the compliance of the SEA within the actuator module and the serial transmission chain design, results from benthtop testings demonstrated limited bandwidth (4.1 Hz to 2.7 Hz for torque >12 N·m) when compared to the design in [74], [75]. However, since the goal of the assistance level was not to reproduce the full torque command as the ankle, 2.7 Hz was sufficient for the treadmill walking task at 0.60 m/s.

Furthermore, although results in FIG. 10A-E showed the con vergence time of NN weights was around 40 to 60 seconds under the treadmill walking task at 0.60 m/s, it is not assumed that the convergence time will be finite or the same if the walking speed or task is changed. Please note that finite-time convergence of NN weights in an adaptive control design is a challenging and an active research problem. In the provided stability analysis, the proposed AIC framework may guarantee the uniformly ultimately bounded stability of the overall closed-loop dynamic system, which means that the system error state exponentially converges to a bounded region. This proof does not claim that the estimated NN weights converge to their ideal weights but the error between the ideal weight and estimated weight remains bounded. As seen in the experiments NN weight converge to a steady state value, which may or may not be ideal NN weights. In short, if the desired speed is modified, only the NN weights may remain bounded but do not claim convergence in finite time. At last, one limitation of the current experimental disclosure design is that no experimental comparison results were included between sEMG or sEMG+US imaging and US imaging alone in the real-time control outcomes. Although the comparison of human volitional effort (joint motion or joint net torque) prediction among sEMG only, US imaging only, and sEMG+US imaging would be easier if performed offline with synchronously collected data, such as in previous studies [35], [36], [42], [46], [47], the online implementation for the real-time control has two main technical challenges. First of all, the online implementation will be quite different from the offline processing given that the data acquisition sampling rate of sEMG signals is much higher than that of US imaging signals, which significantly affects the data synchronization between these two sensing modalities. The computationally-intensive US imaging beamforming and feature extraction causes the much lower data acquisition sampling rate for the online implementation of US imaging-based feedback. Secondly, the working mechanism of the applied sequential processing algorithm that tackles the data fusion between high-sampled sEMG signals (1000 Hz) and low-sampled US echogenicity signals (~7.8 Hz) needs a carrier sampling rate the same as the high-sampled sEMG signals to guarantee the output of the sensor fusion with a high sampling rate (1000 Hz), which satisfies the real-time closed-loop control frequency (200 Hz). This implies that the sequential processing algorithm could still work with only sEMG signals at a high sampling rate but could not work with only US imaging signals at a low sampling rate. An easy approach, like zero-order-hold, to process sole US imaging signals in the real-time implementation may significantly reduce the temporal resolution of the human effort prediction as a feedback signal for the closed-loop control problem and deteriorate the control performance.

In the current disclosure, only participants without neurological disorders were included, so no results are available related to the proposed AAN control performance on individuals with weakened ankle joint function. The next step of this disclosure will be dedicated to the validation of the AAN control framework on participants with incomplete spinal cord injury or hemiplegia after stroke. Although the current treadmill walking experimental disclosure focused on the stance phase, the bidirectional actuation of the ankle exoskeleton can also potentially dorsiflex the ankle joint with adequate assistance torque and bandwidth. Future work will expand the proposed AAN control to both plantarflexion and dorsiflexion assistance during the stance phase and swing phase, respectively. In embodiments of the present disclosure, for the first time, the online combination of sEMG and US imaging signals into a neuromuscular model for a continuous joint volitional effort prediction were investigated and incorporated with an AIC approach to achieve AAN control of a powered ankle exoskeleton. From a real-time perspective, the online muscle activation fusion between high-sampled sEMG signals and lower-sampled US imaging signals was achieved by applying a sequential processing algorithm-based multi-rate observer. The human volitional net plantarflexion effort was predicted via an sEMG-US imaging-driven HNM. A bio-inspired AIC method that incorporated the volitional effort from the sEMG-US imaging-driven HNM was proposed and implemented on the BCD-AnkleExo for ankle joint plantarflexion assistance. The effectiveness of the hardware design and the newly proposed AAN control framework was verified on five participants with no neurological disorders walking on a treadmill. The results from three scenarios demonstrated the superior performance of the proposed AAN control framework with volitional ankle joint effort prediction through the sEMG-US imaging-driven HNM, including ankle joint volitional effort prediction error reduction, trajectory tracking error reduction, and assistance torque integral and overall injected work reduction.

Open-loop or closed-loop functional electrical stimulation (FES) has been widely investigated to treat drop foot syndrome, which is typically caused by weakness or paralysis of ankle dorsiflexors. However, conventional closed-loop FES control mainly uses kinematic feedback, which does not directly capture time-varying changes in muscle activation. In this disclosure, the use of ultrasound (US) echogenicity as an indicator of FES-evoked muscle activation was explored. Additionally, in some embodiments, including US-derived muscle activation, in addition to kinematic feedback, improves the closed-loop FES control performance compared to the closed-loop control that relies only on the kinematic feedback. A sampled-data observer (SDO) was derived to continuously estimate FES-evoked muscle activations from low-sampled US echogenicity signals. Additionally, a dynamic surface controller (DSC) and a delay compensation (DC) term were incorporated with the SDO, noted as the US-based DSC-DC, to drive the actual ankle dorsiflexion trajectory to a desired profile. The trajectory tracking error convergence of the closed-loop system was proven to be uniformly ultimately bounded based on the Lyapunov-Krasovskii stability analysis. The US-based DSC-DC controller was validated on five participants with no disabilities to control their ankle dorsiflexion during walking on a treadmill. The US-based DSC-DC controller significantly reduced the root mean square error of the ankle joint trajectory tracking by 46.52% 7.99% ($p<0.001$) compared to the traditional DSC-DC controller with only kinematic feedback but no US measurements. The results also verified the disturbance rejection performance of the US-based DSC-DC controller when a plantarflexion disturbance was added. Our control design, for the first time, provides a methodology to integrate US in an FES control framework, which will likely benefit persons with drop foot and those with other mobility disorders.

Drop foot is a typical symptom of weakened ankle dorsi-flexion after stroke [1], and other neurological disorders such as multiple sclerosis [3], incomplete spinal cord lesions [4], etc. Affected persons are unable to exhibit normal foot ground clearance during the swing phase, resulting in unnatural steppage gait to avoid tripping/falls [5]. To correct drop foot, functional electrical stimulation (FES), which is an artificial technique to apply electrical potentials across skeletal muscles, can be placed over the peroneal nerve and the tibialis anterior (TA) muscle to induce orthotic effects at the ankle joint. Since the earlier demonstrations of FES to correct drop foot by Kantrowitz [6] and Liberson [7], recent studies [8]-[10] have concurred with its effective orthotic effects on a larger clinical population.

Traditionally, the TA muscle is activated during the swing phase using discrete sensors that detect either heel contact or leg inclination [9]. Here, FES is applied through an open-loop or a trigger-based control method. The stimulation amplitude is fixed or uses a pre-determined trapezoidal shape [7]. Thus, given the nonlinear and time-varying nature of the FES-activated neuromuscular system, current commercial drop foot stimulators' inability to automatically modulate the stimulation intensity is a major drawback. Furthermore, with the open-loop FES control mode, the users may be tempted to choose a higher intensity than necessary to reach enough dorsiflexion for the ground clearance, which would likely aggravate FES-induced muscle fatigue, and thus reduce the effectiveness of open-loop FES control [11], [12].

Time-varying physiological changes in affected muscles and the requirement to track a desired limb angle trajectory necessitate closed-loop FES control. Feedback can provide robust performance and recreate precise and accurate functional joint movements. The major challenges that implement closed-loop FES include highly nonlinear, time-varying properties of electrically stimulated muscle, electromechanical delay (EMD), muscle fatigue, spasticity, and day-to-day variations. To address these challenges, a range of advanced control strategies have been developed to achieve a satisfactory trajectory tracking performance for either knee joint or ankle joint. For example, the high-gain robust nonlinear control [13], input delay compensation (DC) [14]-[16], adaptive control [17], [18], and model predictive control [19], [20] designs for the FES-elicited knee extension tracking or cycling tasks have been thoroughly investigated. For FES-elicited ankle joint motion control, especially for drop foot correction, the adaptive control [21], [22], iterative learning control [11], [12] and repetitive control [23] designs have been proposed in recently years. However, as yet, FES control designs mostly use joint kinematic data as feedback to address the regulation or tracking problem. Apart from the kinematic data, other solutions have also been applied to the closed-loop FES control on different joints, which could be explored for drop foot correction. These solutions include the force prediction modeling of the elbow joint with the consideration of co-activation [24], the pedal force prediction modeling of FES-elicited cycling [25], and the ankle joint torque estimation based on the FES-evoked EMG [26]. Motivation exists to use measurements of FES-evoked muscle activation and thus enable FES control based on more accurate (third-order) musculoskeletal dynamics. Alibeji et al. [15] developed a proportional-integral-derivative (PID) type controller that used a dynamic surface control (DSC) error structure along with a DC term to account for the muscle activation dynamics and EMD. The FES-evoked muscle activation was estimated based on an identified first-order activation dynamic model, which was parameterized by using off-line system identification [27]. Reasonably, real-time physiological muscle state measurements, if available, would be more favorable than an offline identified muscle activation estimator to capture the time-varying muscle's physiological changes. Surface electromyography (sEMG) is indeed one traditional tool that is employed to measure FES-induced or volitional muscle activation levels. However, sEMG is extremely sensitive to electrical interference [28] because sEMG records electrical activity during muscle contraction via electrodes placed on the skin, which are by necessity near the electrodes used in FES. During the stimulation, FES impulses can severely corrupt the sEMG signals with artifacts [29]. For example, FES can deliver impulses on the order of 100 V while sEMG attempts to record muscle electrical signals that are on the order of <100 mV with an inherently low signal-to-noise ratio (SNR). Therefore, the advanced electrical filter circuits or filtering algorithms are necessary to incorporate sEMG into FES control [30]-[36]. Recently, ultrasound (US) imaging has been proposed as an alternative non-invasive technology to directly visualize skeletal muscle contractility and assess muscle activation levels under both voluntary and FES-elicited joint movement [37]-[41]. Compared to sEMG, US imaging is unaffected by stimulation artifacts during FES.

Further, due to its ability to directly visualize the muscle, the derived signals are devoid of interference from the adjacent muscles. However, US imaging is yet to be shown as a feasible real-time sensing modality that can be integrated into closed-loop FES control. In this disclosure, for the first time, feasibility of deploying US imaging to detect FES-elicited muscle activation levels and incorporate the US imaging-derived signal in an FES control design is demonstrated. The US imaging-based control framework is validated to track an ankle dorsiflexion trajectory during a treadmill walking task. The main challenge to incorporate US imaging-derived signals in the closed-loop FES control is the low sampling rate of the US imaging-derived feedback signal. The low sampling rate mainly stems from computationally intensive US image generation and its processing. So far, previous US imaging studies processed and derived volitional [38], [39], [41] or FES-evoked [40], [42] muscle activation data in an offline manner. Thus, the real-time use of US imaging data to monitor FES-evoked muscle activation and aid its control performance remains unexplored. Specifically, the US imaging-derived echogenicity signal is used for measuring muscle activation, although at a much lower sampling frequency compared to kinematic measurements from inertial measurement units (IMU) or angular encoders, and integrate it with a continuous FES closed-loop control approach. Unlike architectural features that are extracted from US imaging, like pennation angle, fascicle length, muscle thickness, and tissue displacement, US echogenicity refers to the ability to reflect US waves in the context of surrounding tissues [43], which can be visualized as the brightness and darkness of the region of interest (ROI) and calculated as the average brightness of the ROI in each image frame. US echogenicity calculation does not rely on complex and time-consuming dynamic pixel displacement tracking algorithms, which brings potential computational benefits to save processing time in the real-time application. Previous offline studies have demonstrated a good correlation between echogenicity and muscle contractility/activation [41], [42], [44], [45].

To address the challenge of assimilating the lower-sampled US imaging-derived signals, a sampled-measurement data-based observer (SDO) is derived to estimate muscle activation levels in a continuous manner. Due to gait-to-gait and person-to-person variations, a pre-defined time-dependent desired trajectory needs to be compressed or stretched online to adapt to the walking conditions, which can easily cause a mismatch between gait phases and affect control performance. Therefore, this disclosure, inspired by virtual constraints in [46], proposes to generate a time-independent desired ankle joint trajectory in joint space based on the portraits of thigh and shank segments from normal gait data obtained from walking on a treadmill. Compared to the preliminary simulation disclosure in [47], walking experiments were conducted with the US-based DSC-DC control method on a treadmill. Embodiments of the present disclosure include: 1) derivation of an US-based DSC-DC control framework to handle low-sampled US signals and EMD in FES, 2) trajectory tracking error convergence analysis of the combined observer and controller based on a Lyapunov-Krasovskii functional, 3) time-independent ankle joint desired trajectory generation based on virtual constraints given the portraits of thigh and shank segments, 4) experiments comparing the US-based DSC-DC control method and traditional DSC-DC control method, as well as ankle trajectories comparison between FES-on and FES-off conditions during the swing phase, and 5) evaluation of the disturbance rejection performance during the swing by adding plantarflexion disturbance.

Ankle Joint Musculoskeletal Model and Ankle Joint Dorsiflexion Motion Dynamics

Figure 15:
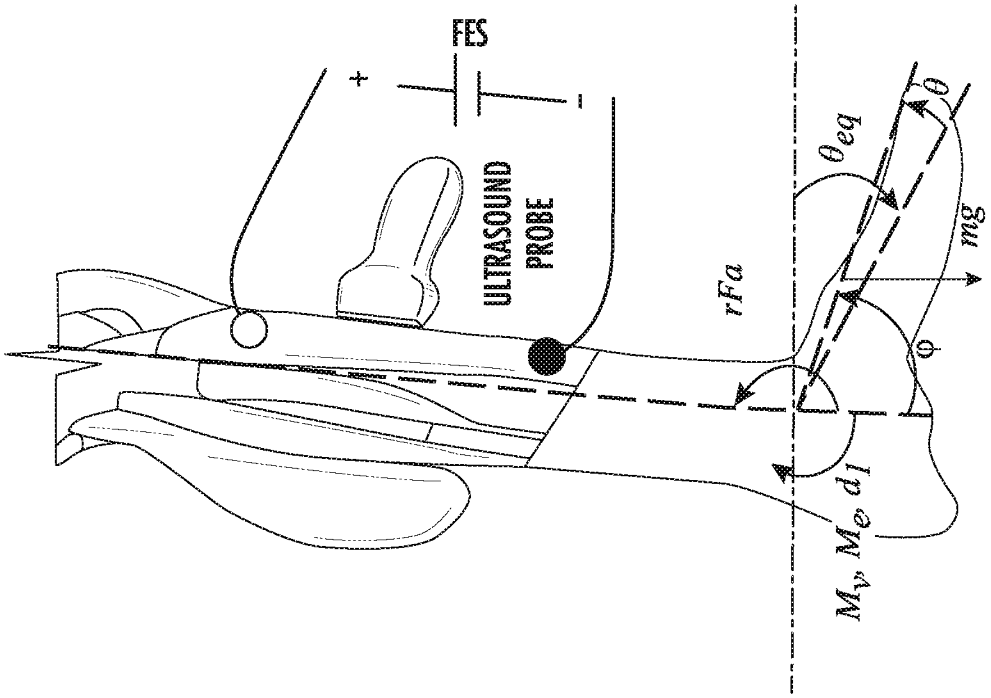
FIG. 15 is a schematic diagram according to implementations described herein.

The dynamic model of the FES-actuated limb movement as shown in FIG. 15, is given as $$J\ddot{\theta}(t) + M_v + M_e + M_g + D_{ext} = \tau(t), \tag{33}$$

where J∈R+ is the unknown inertia term of the foot along the dorsiflexion axis of rotation, and θ(t), θ'(t), and θ"(t)∈R denote the angular position, angular velocity, and angular acceleration, respectively. The constant limb equilibrium point is represented as θeq R−, which represents the joint's posture when the limb is completely relaxed. The passive moment Mv(θ') R is a term to represent musculoskeletal viscosity, Me(θ) R is a term to represent musculoskeletal elasticity, and Mg(θ) =mgl sin(π+θ+θeq) R is the gravitational term acting on the ankle. The mass of the limb and the length from the limb's center of mass to its rotation center in the sagittal plane are denoted as m R+ and l∈R+, respectively. The explicit definitions of the functions Mv(θ') and Me(θ) can be obtained from [13], [17]. The term related to external disturbance and unmodeled effects in the neuromusculoskeletal system is denoted as $D_{ext}(t)$ ∈R. The limb torque elicited by FES is given as $$\tau(t) \triangleq r(\theta)F_m\eta_1(\theta)\eta_2(\dot{\theta})\cos(\alpha)a, \tag{34}$$

where each term on the right-hand side is defined in the following properties:

Property 1: The variable r(θ) R+ represents the moment arm for the muscle tendon force, which is a function of the joint position, and is given as r(θ)=0.013(θeq θ)+0.035 [48]. So the moment arm is a continuously differentiable, positive, and bounded function with a bounded first-order time derivative.

Property 2: The variable Fm R+ represents the constant maximum isometric muscle contraction force at the equilibrium position.

Property 3: Variables η1(θ) and η2(θ') denote the nonlinear relationships of force-fascicle length and force-fascicle velocity [49], and both of them are continuously differentiable, non-zero, positive, and bounded functions.

Property 4: The pennation angle between the muscle fascicle and deep aponeurosis, denoted by α(θ) R+, increases monotonically within the approximate range 0-30° as the muscle contracts [50].

Property 5: The variable a(t) [0, 1] denotes the muscle activation level whose ideal dynamics is represented by the following continuous first-order differential equation [51]:

$$a(t) = \frac{-a(t) + u(t - \tau_M)}{T_a} \tag{35}$$

In (3), the EMD caused by FES is denoted as τM∈R+ and assumed to be known, and Ta R+ is the muscle activation decay constant. The normalized non-delayed FES input u(t) [0, 1] is due to the boundedness of the muscle stimulation. From [51], the input u(t) is modeled by a piecewise linear function $$u(t) = \begin{cases} 0, & \bar{u} < u_{min} \\ \frac{\bar{u}(t) - u_{min}}{u_{max} - u_{min}}, & u_{min} \le \bar{u} \le u_{min} \\ 1, & \bar{u} > u_{max} \end{cases} \quad (36)$$

where $u_{min}$ and $u_{max} \in$ R≥0 are the stimulation threshold and stimulation saturation, respectively, and $\bar{u}(t)$ R≥0 is the modulated parameter (current, pulse width, or frequency) applied on the TA muscle.

To facilitate the controller development and stability analysis, the following assumptions are made herein:

Assumption 1: The angular position and velocity signals θ, θ' are continuously measurable.

Assumption 2: The muscle activation signal a is measured by normalizing the US imaging-derived echogenicity signal [41] in a real-time manner, but with a much lower sampling frequency compared to the sampling frequency of the angular position and velocity. The normalized US echogenicity signal is used as muscle activation feedback only at discrete time instant $t_k$ (k=0, 1, 2, . . . , ∞), and $\{t_k\}$ is a monotonically increasing sequence and satisfies $\lim_{k\to\infty} t_k=\infty$. The sampling interval is set as a constant value T, namely $T=t_{k+1}\ t_k$. Due to the data transmission delay, the sampled activation signal is available at instants $t_k+\tau_k$, where $\tau_k>0$ denotes the unknown and time-varying transmission delay with an upper bound $\tau^-$. Thus, the maximum time duration between two successively available muscle activation measurements is $T+\tau^-$, denoted as T.

Assumption 3: The desired ankle trajectory $\theta_d \in$ R and its time derivatives, $\theta'_d \in$ R and $\theta''_d \in$ R, are bounded.

Sampled-Data Observer Design

Define a state variable x=hθ(t), θ'(t), a(t)iT. The over-all continuous neuromusculoskeletal system can be expressed in state-space form as $$\begin{bmatrix} \dot{x}_1 \\ \dot{x}_2 \\ \dot{x}_3 \end{bmatrix} = \begin{bmatrix} x_2 \\ \frac{1}{J_\Gamma}\left(-f_\Gamma(x_1, x_2) - D_{ext\Gamma} + x_3\right) \\ \frac{-x_3 + u(t-\tau_M)}{T_a} \end{bmatrix}, \text{ where} \quad (37)$$

$$f_\Gamma(x) = \frac{M_v(x_2) + Me(x1) + Mg(x1)}{\Gamma(x)},$$

$$\Gamma(x) = r(x1)Fm\eta 1(x1)\eta 2(x2)\cos(\alpha),\ J\Gamma = \frac{J}{\Gamma(x)},\ \text{and } D_{ext\Gamma} = \frac{D_{ext\Gamma}}{\Gamma(x)}.$$

Hereafter, the following assumptions are also made herein:

Assumption 4: Based on the properties in (2), the function Γ(x) is continuously differentiable, positive, and bounded. Also, the first-order derivatives of Γ(x) and 1/r(x) exist and are bounded.

Assumption 5: Based on Assumption 4, the term JΓ is bounded, and its first-order time derivative exists and is bounded. In addition, JΓ satisfies the inequality $$a_1\|\Theta\|^2\Theta^T J_\Gamma \Theta a_2 \Theta^2,\ \Theta R''$$

for some known positive constants a1, a2 ∈ R+.

Assumption 6: The external disturbance in the system Dext in (1) is bounded. Therefore, based on Assumption 4, DextΓ is also bounded. According to (5), the state element $x_3$ is independent from $x_1$ and $x_2$, so the overall system could be considered as a cascade system, and the SDO will be designed for the subsystem related to x3. Based on the sampled and delayed muscle activation from US imaging, the continuous-time observer for muscle activation is given as [52]-[54]

$$\dot{\hat{x}}_3(t) = -\frac{\hat{x}_3(t)}{T_a} + \frac{u(t-\tau_M)}{T_a} + \gamma\varepsilon_3(t_k) \quad (38)$$

$$t \in [t_k + \tau_k, t_{k+1} + \tau_{k+1}),\ k = 0, 1, 2, \ldots, \infty$$

where γ R+ is the observation gain used for updating the observer which will be subsequently constrained in stability analysis section. The variable $\varepsilon_3(t_k)=\hat{x}_3(t_k)\ x_3(t_k)$ represents a constant value (a zero-order hold) during the time interval $t\in[t_k+\tau_k,\ t_k+1+\tau_k+1)$, is updated at the time point when the US echogenicity is available, and is assumed to be upper bounded by $$\bar{\varepsilon}_3^{k}$$

$\in R^+$. Therefore, the observer model is of a hybrid nature with continuous and discrete variables. The continuous observation error is defined as $\varepsilon_3(t)=\hat{x}_3(t)\ x_3(t)$, and by taking its time derivative and substituting (5) and (6), the observation error dynamics is given as $$\dot{\varepsilon}_3(t) = -\frac{\varepsilon_3(t)}{T_a} + \gamma\varepsilon_3(t_k) \quad (39)$$

$$t \in [t_k + \tau_k, t_{k+1} + \tau_{k+1}),\ k = 0, 1, 2, \ldots, \infty$$

Desired Joint Trajectory Planning—High-Level Control

During human locomotion, overground or on the treadmill, a time-dependent pre-defined desired ankle dorsiflexion trajectory needs to be compressed or stretched to adapt to gait-to-gait and person-to-person variations, which is a cumber-some design process. Therefore, a time-independent trajectory generation profile is utilized based on virtual constraints [46]. The desired ankle dorsiflexion trajectory was generated on-line given the orientations and angular velocities of the thigh and shank segments during the locomotion. Consider the term:

$$h_d(v(q))\in\mathbb{R}\left(q = \left[\theta_{shank}, \dot{\theta}_{shank}, \theta_{thigh}, \dot{\theta}_{thigh}\right]^T\right)$$

a desired virtual constraint function that is represented with the Bezier polynomial as $$h_d(v(q)) = \sum_{\bar{k}=0}^{M} \varrho_{\bar{k}} \frac{M!}{\bar{k}!(M-\bar{k})!} v^{k}(1-v)^{M-\bar{k}} \quad (40)$$

where M R+ is an integer equal to the number of Bezier polynomial terms, ϱ k¯ R represents the parameters that are determined through the optimization mentioned in [55], [56], and v∈R≥0 is calculated as $$v(q) = \frac{\theta(q) - \theta^+}{\theta^- - \theta^+} \quad (41)$$

where θ+ and θ− are the maximum and minimum values of the function θ(q), respectively, and θ(q)=ξ¯0+ξ¯1θshank+ξ¯2θ'shank+ξ¯3θthigh+ζ¯4θ'thigh represents the applied phase variable.

$\xi_i$∈R (i=1, 2, 3, 4) is selected such that θ(q) is monotonically increasing or decreasing. Finally, the desired ankle trajectory θd during the swing phase is set as hd(v(q)). To obtain the optimal solution of ∂k¯ in the Bezier polynomial (8), a genetic algorithm-based particle swarm optimization (GAPSO) [57] was used to minimize the cost function:

$$\min_{\varrho\kappa} R = \sum_{i=1}^{N} \left(h_d^i(v(q)) - h_m^i\right)^2 \quad (42)$$

where N represents the number of data samples used in the optimization, and $$h_d^i$$

and $$h_m^i$$

represent the Bezier polynomial-computed and measured ankle dorsiflexion motion values at the $i^{th}$ time instant, respectively. The GAPSO utilizes kinematics data that were collected from participants with no disabilities at the walking speed of 0.6 m/s. Target ankle trajectories are designed based on Bezier polynomials, compared to other splines, due to their useful properties that are amenable [55] for numerical stability during the optimization.

Low-Level Control

The control objective is to develop a trajectory tracking controller for an FES-evoked limb motion that takes both kinematic and muscle activation feedback during the controlled motion. Here, US imaging-derived muscle activation is used as feedback in the control design. Due to the computationally intensive US signal beamforming and imaging process, the real-time feedback of a US imaging-derived signal may be sampled at a low rate, compared to a higher sampled kinematic signal. Therefore, an SDO that combines muscle activation dynamics and sparse US imaging measurements is proposed to continuously estimate FES-evoked muscle activation. With the feedback from the SDO and joint kinematics, a PID-type DSC controller plus a DC term is proposed to achieve the trajectory tracking task. The diagram of the proposed framework is shown in FIG. 16A.

Figure 16A:
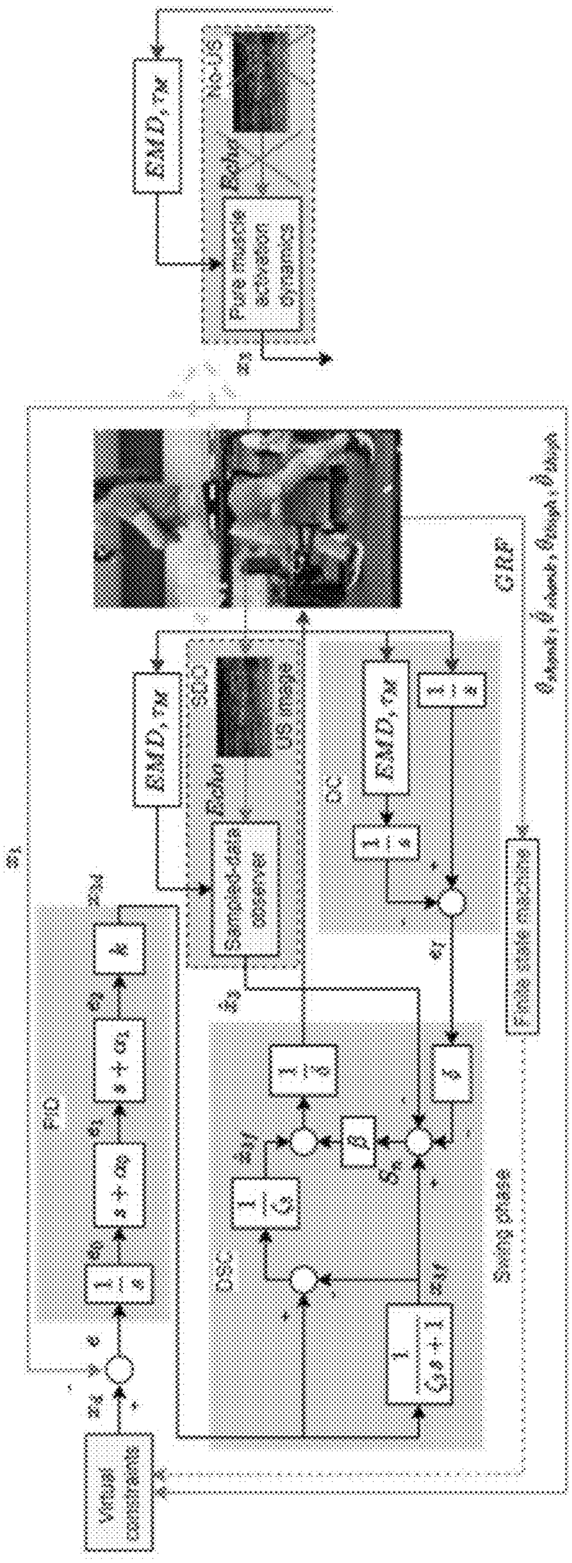
FIGS. 16A and 16B are schematic diagrams according to implementations described herein.
Figure 16B:
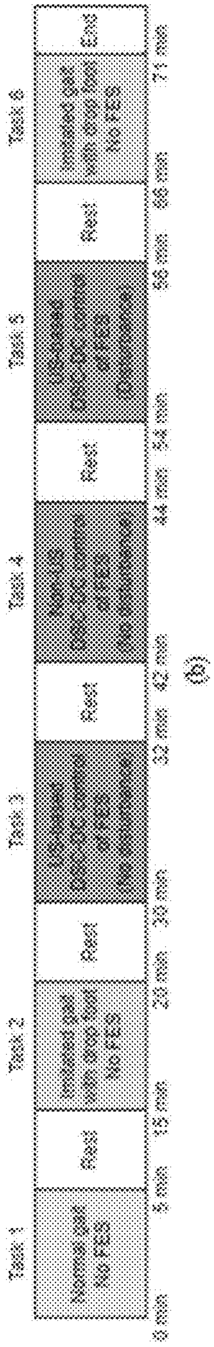

Referring now to FIG. 16A, a block diagram of a proposed US-based DSC-DC control framework for the ankle neuromusculoskeletal system during walking on an instrumented treadmill. Virtual constraints were used to generate the desired ankle joint trajectory online during the walking swing phase. The finite state machine was used to differentiate the swing phase and stance phase during walking based on the ground reaction force. Black lines and arrows represent the flows after the intermediate data processing, red solid lines and arrows represent the direct measurements from the treadmill walking experiments, the red dashed line represents the binary state of the swing or stance phase, and blue lines and arrows represent the non-delayed control signals (FES pulse width modulation) to the ankle neuromusculoskeletal system, respectively. The diagram could be shifted to the DSC-DC control framework by changing the "SDO" part to the "No-US" part (shown to the right of the green arrow). Referring now to FIG. 16B, a schematic diagram depicting treadmill walking tasks sequence on each participant is provided.

Remark 1. Compared to the traditional integrator back-step-ping method, the benefit of the DSC method is to approximate the derivative of the control input with the dynamics of a low-pass filter. Consequently, this approach avoids taking another time derivative, which otherwise would result in an acceleration signal-based control law [15].

The details of the low-level control design are given below.

Open-loop error development: The trajectory tracking error for the ankle neuromusculoskeletal system is given as $$e(t) = x_d(t) - x_1(t) \quad (43)$$

where $x_d(t)$∈R is the desired differentiable ankle dorsi flexion trajectory, which is generated online based on the aforementioned virtual constraints. For facilitating control design and stability analysis, the following auxiliary error signal $e_1(t)$∈R is defined as $$e_1(t) = \dot{e}_0(t) + a_0 e_0(t) \quad (44)$$

Where $\alpha_0$∈R+ is a control gain and e0(t) is a designed term to incorporate integral control, which is defined as $$e_0(t) = \int_0^t e(s)ds \quad (45)$$

Another auxiliary error signal $e_2(t)$∈R is defined as $$e_2(t) = \dot{e}_1(t) + \alpha_1 e_1(t) \quad (46)$$

where $\alpha_1$∈R+ is a control gain. After taking the time derivative of $e_2(t)$, multiplying with $J_\Gamma$, and using (5), (11)-(13), the open-loop error dynamics are obtained.

$$J_\Gamma \dot{e}_2 = J_\Gamma \ddot{x}_d + f_\Gamma + D_{ext\Gamma} - x_3 + J_\Gamma(\alpha_0 + \alpha_1)\dot{e} + J_\Gamma \alpha_0 \alpha_1 e \quad (47)$$

Backstepping design and dynamic surface control: By introducing a desired virtual control input signal as $x_{3d}$ ∈ R≥0, the filtered desired signal, denoted as $x_{3f}$, is obtained by passing $x_{3d}$ through a low-pass filter such that $$x_{3d} = \zeta_3 \dot{x}_{3f} + x_{3f},\ x_{3d}(0) = x_{3f}(0) \quad (48)$$

where $\zeta 3 \in R+$ is the low-pass filter time constant. By defining the filtering error as $\gamma_f = x_{3d} - x_{3f}$, the time derivative of the filtered intermediate signal is a continuously differentiable function and expressed as $$\dot{x}_{3f} = \frac{y_f}{\zeta_3}.$$

By defining the surface error as $S = x_{3f} - x_3\hat{}$, and adding and subtracting $x_{3d}$ and $x_3\hat{}$, the open-loop error dynamics (15) can also be written as $$J_\Gamma \dot{e}_2 = J_\Gamma \ddot{x}_d + \varepsilon_3 + S + y_f - x_{3d} + D_{ext\Gamma} + f_\Gamma + J_\Gamma(\alpha_0 + \alpha_1)\dot{e} + J_\Gamma \alpha_0 \alpha_1 e \quad (49)$$

By adding and subtracting ½ J'Γ$e_2$ and a DC term, $e_l \in R$, multiplied by a constant gain $\delta \in R^+$, where $e_l(t)=$ $$\int_{t-\tau M}^{t}$$

u(s)ds, the rearranged format of (17) can be given as $$J_\Gamma \dot{e}_2 = -\frac{1}{2} J_\Gamma e_2 + S + y_f - \delta_{el} + \varepsilon_3 + \tilde{H} + O - x_{3d} - e_1 \quad (50)$$

where the auxiliary signals H˜ (e, e1, e2, el, xd, x'd, x"d, t)∈R and O (xd, x'd, x"d, Γ, t)∈R are defined as $$\tilde{H} = H - H_d,\ O = D_{ext\Gamma} + H_d \quad (51)$$

$$H = \frac{1}{2}\dot{J}_\Gamma e_2 + J_\Gamma \ddot{x}_d + f_\Gamma + \delta e_l + e_1 + J_\Gamma(\alpha_0 + \alpha_1)\dot{e} + J_\Gamma \alpha_0 \alpha_1 e$$

$$H_d = J_{\Gamma d}\ddot{x}_d + f_\Gamma(x_d, \dot{x}_d)$$

$$\text{where } J_{rd} = \frac{J}{\Gamma(x_d)} \text{ and } f\Gamma(xxd, x^\bullet d) = \frac{Mv(x^\bullet d) + Me(xd) + Mg(xd)}{\Gamma(x_d)}.$$

Furthermore, according to Assumptions 1, 2, 4 and 5, the two auxiliary signals H˜ and O can be bounded as $$|\tilde{H}| \le \rho(\|z\|)\|z\|,\ |O| \le \zeta \quad (52)$$

where $\xi \in R^+$ is a known constant ρ (||z||)∈$R^+$ is a positive globally invertible non-decreasing bounded function, and z is defined as $$z = [e_0, e_1, e_2, e_l]^T \quad (53)$$

In the expression (18), the desired intermediate signal is defined as [15]

$$x_{3d} = Ke_2 = K\dot{e} + (\alpha_0 + \alpha_1)Ke + K\alpha_0\alpha_1 e_0 \quad (54)$$

where $K = K_1 + K_2 + K_3 \in R^+$, which implies a PID type signal with three different control gains, and the corresponding coefficients are defined as $K_p = (\alpha_0 - \alpha_1)K$, $K_d = K$, and $K_i = K\alpha_0\alpha_1$. By using the definition in (22), (18) can be rewritten as $$J_\Gamma \dot{e}_2 = -\frac{1}{2} J_\Gamma e_2 + S_n + y_f + \varepsilon_3 + \tilde{H} + O - Ke_2 - e_1 \quad (55)$$

where $S_n = S - \delta_{el}$, which is the augmented surface error that contains the DC term $\delta_{el}$. By substituting the surface error and (6), the time derivative of $S_n$ is given as $$\dot{s}_n = \frac{y_f}{\zeta_3} + \frac{\hat{x}_3}{T_a} - \delta u(t) - \gamma\varepsilon_3(t_k) + \left(\delta - \frac{1}{T_a}\right)u(t - \tau_M) \quad (56)$$

The DC term $e_l$ is proposed to replace the delayed input in the muscle activation dynamics with a non-delayed input. By manipulating the non-delayed input, which is defined as the control law u(t) as $$u(t) = \frac{1}{\delta}\left[\beta S_n + \frac{y_f}{\zeta_3}\right] \quad (57)$$

Where $\beta \in R^+$ is a control gain, we can get the closed-loop surface error dynamics as below $$\dot{S}_n = -\beta S_n + \frac{\hat{x}_3}{T_a} + \left(\delta - \frac{1}{T_a}\right)u(t - \tau_M) - \gamma\varepsilon_3(t_k) \quad (58)$$

Stability Analysis

Lemma 1. For any given positive definite matrix $M \in R^{n \times n}$, a positive scalar α, and a vector function ν, the following Cauchy Schwarz inequality always holds as $$\left[\int_0^\alpha v(s)ds\right]^T M\left[\int_0^\alpha v(s)ds\right] \le \alpha\left[\int_0^\alpha v^T(s)Mv(s)ds\right]$$

The proof for this Lemma can be found in [58].

Theorem 1. Consider the neuromusculoskeletal system in (5) with a known EMD $\tau_M$, by using the TA muscle activation estimation from the SDO with sparse US imaging-derived muscle activation update in (6) and control law in (25), the FES-elicited ankle dorsiflexion trajectory tracking error is ensured to be semi-globally uniformly ultimately bounded (SGUUB) in a sense that $$|e| \le \sigma_0 \exp(-\sigma_1 t) + \sigma_2 \quad (59)$$

where $\sigma_1$, $\sigma_2$, $\sigma_3$ ∈R+ are subsequently defined in the stability analysis, provided that the observation gain γ and control gains α0, α1, K1, K2, β, δ, and ζ3 satisfy the following sufficient conditions:

$$\alpha_0 \ge \frac{1}{2},\ \alpha_1 \ge \frac{1}{2},\ K_1 \ge \frac{3}{2},\ \frac{1}{\zeta_3} \ge \frac{1}{2} + \frac{\overline{\eta}^2}{2\epsilon},\ K_2 \ge \frac{\rho^2(\|z\|}{4\xi}$$

-continued $$0 < \gamma \le (2 - T_a)T_a^{-1}\left(2\overline{T} + 1\right)^{-1}$$

$$\beta \ge \max\left\{\frac{1}{2}\left(-\nu + \sqrt{\nu^2 + 4\tau M\delta^{-2}}\right\}\right.$$

$$\frac{1}{2}\left(k^{-1}\tau M\delta^{-2} + \sqrt{k^{-2}\tau_M^2\delta^{-4} + 4k^{-1}\tau_M\delta^{-2}\zeta_3^{-1}}\right)$$

where $\in$ is a arbitrary positive constant, and $\bar{\eta}$, $\xi$, $\partial$, and $\kappa$ are positive constant values.

Experimental Implementation

As discussed herein, it is hypothesized that the consideration of US imaging-derived muscle activation updates would result in a more accurate muscle activation estimation when FES is applied, when compared with the muscle activation that is calculated based on the pure dynamic model in (3). Subsequently, the use of accurate muscle activation in the closed-loop FES control and the DSC+DC would improve the control performance. To validate this hypothesis and demonstrate the efficacy of the newly developed US-based DSC-DC controller, it was tested for an ankle dorsiflexion trajectory tracking task during the walking swing phase to deal with the drop foot problem. Furthermore, it was compared with a traditional DSC-DC controller with the pure offline identified muscle activation dynamics. In addition, given that the ultimate goal of the controller is to improve ground clearance due to drop foot, the ankle joint trajectories during the walking swing phase with controlled FES and without FES were also compared and analyzed.

Experimental Apparatus and Protocol

The disclosure was approved by the Institutional Review Board (IRB) at North Carolina State University (IRB number: 20602). Five young participants (identified as A01, A02, . . . , A05, 3M/2F, age: 25.4±3.1 years, height: 1.77±0.10 m, mass: 78.0±21.1 kg) without any neuromuscular or orthopedic disorders were recruited in this disclosure. Every participant was familiarized with the experimental procedures and signed an informed consent form before participation. To identify the individual muscle activation decay constant Ta and EMD τM, each participant was configured with an isometric condition, as shown in previous studies [39], [41], and a step FES input was applied to the TA muscle. Three steps were conducted to extract parameters of Ta and τM from the input FES signal and the dorsiflexion torque measurements. Firstly, the EMD τM was determined by measuring the time difference from the instant when the FES was applied to the instance when the measured torque began to increase. Secondly, the normalization of the measured dorsiflexion torque was shifted to the left by the EMD value to account for the input delay period. FIG. 43 shows the results of muscle activation decay constant $T_a$ and EMD $\tau_M$ from the system identification testing under isometric configuration on individual participants.

Thirdly, under the assumption that the muscle activation dynamic model is a first-order system, the activation decay constant was identified by solving the time constant that produced the minimal error between the normalized shifted torque measurement and the normalized response of the first-order system with a normalized step input signal. Results of individual Ta and τM values from the above identification steps are summarized in FIG. 43.

The main experimental procedures are walking tasks at 0.6 m/s under different conditions on an instrumented treadmill (Bertec Corp., Columbus, OH, USA) with two split belts. Two in-ground force plates (AMTI, Watertown, MA, USA) mounted under two split belts were used to measure ground reaction force (GRF), which was used to differentiate stance phase and swing phase within a gait cycle. The swing phase was triggered when the GRF's z-axis value was less than 5% of each participant's body mass with a unit of kg. Two low-cost 6-axis IMUs (MPU 9250, TDK InvenSense Headquarters, CA, USA) were attached to the right shank and right thigh to measure the 2-D motion in the sagittal plane. The pitch orientations of the shank and thigh segments were determined by using a complementary filtering method, as detailed in [59]. An ankle brace with an incremental encoder (1024 pulses per revolution, TRD-MX1024BD, AutomationDirect, GA, USA) was attached to the right ankle joint to measure the angular position and velocity of dorsiflexion and plantarflexion. A pair of electrodes (size: 2" 2") were placed on the fibular head and the distal belly of the TA muscle, respectively, to pass the biphasic stimulation pulse trains generated by a commercial stimulator (Rehastim 2, HASOMED GmbH, Germany). A clinical linear US transducer (L7.5SC Prodigy Probe, S-Sharp, Taiwan) with 128 channels was attached to the TA muscle belly perpendicularly by a customized 3D printed holder [39] to image the targeted region in a longitudinal direction. The depth of US imaging was set as 40 mm to include the entire TA muscle area. Six walking tasks were performed on each participant at a speed of 0.6 m/s. The details are given below and also shown in FIG. 16B, discussed in more detail below.

Task 1: This task was used for determining the parameters of the Bezier polynomial, via the GAPSO method, to generate the desired ankle joint trajectory online in Tasks (3-5). Here, each participant was asked to walk normally (with preferred ankle dorsiflexion and plantarflexion during the swing and stance phases) on the treadmill for five minutes.

Task 2: Here the task was to imitate the drop foot pat-tern during the walking swing phase on unimpaired participants. Each participant was asked to walk with an imitated drop foot (without voluntary TA muscle contraction during the swing phase) on the treadmill for five minutes. This task might be repeated if there was no significant difference in the ankle joint trajectories during the swing phase in Task 1.

Task 3: In this task, the drop foot correction performance was verified by using the proposed US-based DSC-DC control framework. Each participant was asked to keep the same walking pattern as in Task 2 while the proposed US-based DSC-DC control framework was applied during the swing phase to assist ankle dorsiflexion by stimulating only the TA muscle and tracking the online generated desired trajectory (the virtual constraint model was optimized by using data collected from Task 1).

Task 4: In Task 4, the drop foot correction performance of Task 3 was compared with that of the DSC-DC control framework without US feedback. Similar experimental procedures as in Task 3 were used, but a traditional DSC-DC controller without US echogenicity-derived muscle activation update was used.

Task 5: This task evaluated the disturbance rejection performance by using the proposed US-based DSC-DC control framework. Similar experimental procedures as in Task 3, but the lateral and medial gastrocnemius muscles were also stimulated with a relatively low constant stimulation intensity during the swing phase.

Task 6: Here the imitated drop foot pattern was re-evaluated during the walking swing phase after removing all FES intervention. The experimental procedures in Task 2 were repeated.

During the experiments, Task 1, Task 2, and Task 6 were always performed in the same order, whereas the order of control Tasks (3-5) was randomly selected. During the experimental procedures from Task 2 to Task 6, the participants were not allowed to view the online generated desired trajectory or the ankle joint performance in real-time. A minimum 10-minute rest period was provided for participants between two successive tasks to avoid muscle fatigue. For Task 1, Task 2, and Task 6, only the measurements data within the middle two minutes were collected for analysis, while for Task 3, Task 4, and Task 5, to avoid FES-induced muscle fatigue, each walking trial lasted two minutes, and data throughout the trial were collected for analysis. A real-time target machine (Speedgoat Inc., Liebefeld, Switzerland) and analog and digital data acquisition boards IO 101 and IO 306 were used to record GRF, IMUs, and encoder signals at 1000 Hz. The controllers in Tasks 3-5 were programmed in Simulink (R2019b, MathWorks Inc., MA, USA) and implemented on the target machine with a frequency of 1000 Hz. The control Tasks required the EMD value and the activation decay constant for the activation state estimators with and without the US imaging-derived update. These values were determined using a system identification experiment conducted on a different day before the treadmill walking experiments under the isometric dorsiflexion condition, which is detailed in [20]. The biphasic stimulation pulse trains had a frequency of 33 Hz, and the current amplitude was set as 20 mA for all participants, while the pulse width was modulated between the subjective threshold and saturation automatically by the controllers. Also, the threshold and saturation of the stimulation pulse width were determined using the same isometric dorsiflexion experiment [20].

US Echogenicity-Derived Muscle Activation Calculation

Figure 17:
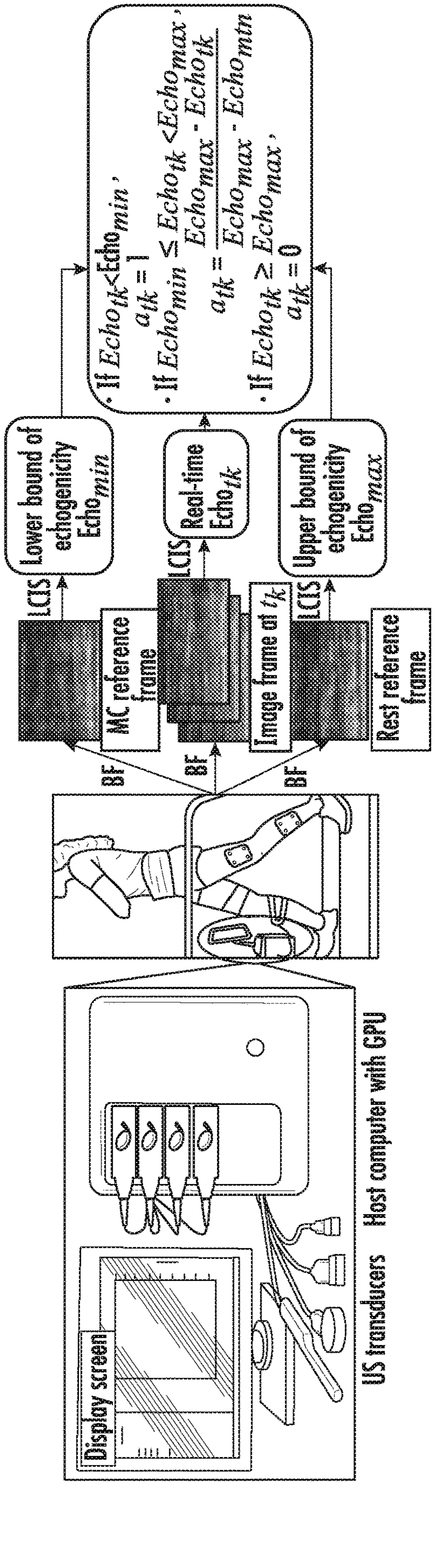
FIG. 17 is a schematic diagram according to implementations described herein.

FIG. 17 presents the illustrative diagram for the US imaging-derived low-sampled muscle activation measurements. Offline studies [41], [42] have shown that US echogenicity has a promising performance regarding volitional and FES-evoked ankle dorsiflexion effort prediction, indicating a good correlation between the US echogenicity and the muscle activation. Therefore, in this disclosure, US echogenicity is used as a measurement of FES-induced muscle activation. The radio frequency data from the US machine were online beamformed based on a line-by-line beamforming method [60]. The echogenicity value from the US image at time instant tk is calculated as $$\mathrm{Echo}_{t_k} = \frac{1}{N_A N_L}\sum_{x=1}^{N_A}\sum_{y=1}^{N_L} I_{t_k}(x, y) \tag{60}$$

where $N_A$, $N_L \in R+$ represent the pixel numbers along axial and lateral directions, respectively. The term $I_{tk}$ $(x,y) \in R$ represents the US intensity information at the pixel location (x,y) on the image at $t_k$ instant from the logarithmically compressed imaging signals after the beamforming procedure. Therefore, the 2D map time sequence is transferred to a 1D signal time sequence. Visually, if the individual pixel intensity information is normalized to the gray-scale value (between 0 and 255), it will present the brightness of each pixel on the 2D map. Thus, the calculated echogenicity signal represents the overall brightness within the region of interest. Our previous studies showed that there is a strong negative correlation between the echogenicity change and the muscle contraction level (known as muscle activation here) [41]. Therefore, here, the US echogenicity-derived muscle activation is calculated as the following piecewise function $$a_{t_k} = \begin{cases} 1 & \mathrm{Echo}_{t_k} < \mathrm{Echo}_{min} \\ \dfrac{\mathrm{Echo}_{max} - \mathrm{Echo}_{t_k}}{\mathrm{Echo}_{max} - \mathrm{Echo}_{min}} & \mathrm{Echo}_{min} \le \mathrm{Echo}_{t_k} < \mathrm{Echo}_{max} \\ 0, & \mathrm{Echo}_{t_k} \ge \mathrm{Echo}_{max} \end{cases} \tag{61}$$

where $\mathrm{Echo}_{max}$ and $\mathrm{Echo}_{min}$ are the individual upper and lower bounds of echogenicity signals that are determined under the muscle rest condition and the maximum stimulation condition (with individual FES saturation). The prior testings showed the real-time US echogenicity data was transferred from the US machine to the FES control system at a rate of 7.8 frames per second, which indicates the US imaging-derived muscle activation measurement is sampled at 7.8 Hz.

Results of Online Desired Trajectory Generation

The ankle joint's angular position measurements and the shank's and thigh's orientations and angular velocities during the swing phases of 30 stabilized walking gait cycles were collected in Task 1 across five participants. The data were used to optimize the parameters ∂k in the Bezier polynomial (8), which generated the desired ankle joint trajectory for each participant in control Tasks 3-5. The joint kinematic patterns (shank's and thigh's orientations and angular velocities) during the swing phase across gait cycles facilitated the generation of the desired ankle joint trajectory via GAPSO.

Figure 18:
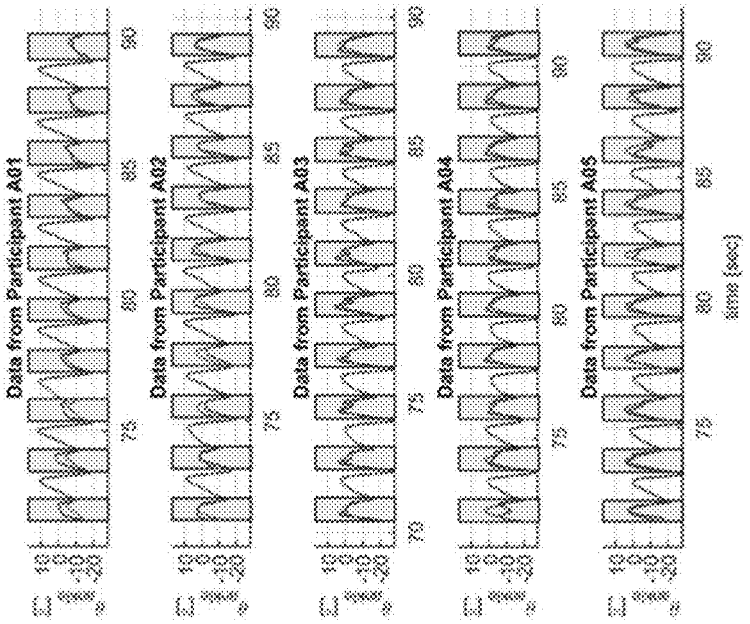
FIG. 18 is a schematic diagram according to implementations described herein.
Figure 19A:
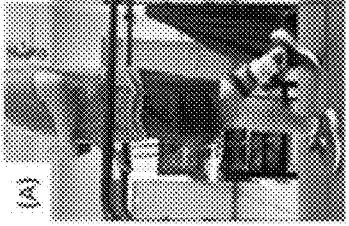
FIG. 19A-H are schematic diagrams according to implementations described herein.
Figure 19B:
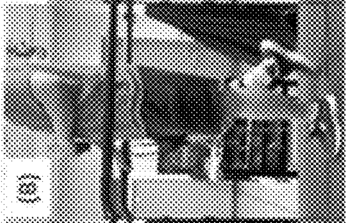
Figure 19C:
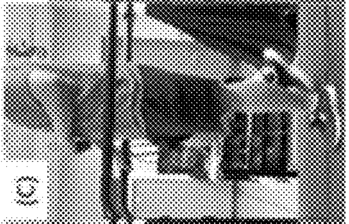
Figure 19D:
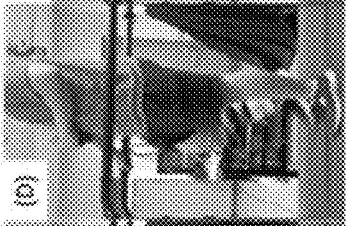
Figure 19E:
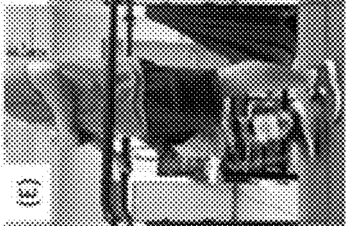
Figure 19F:
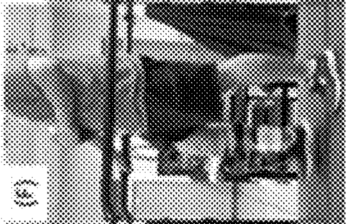
Figure 19G:
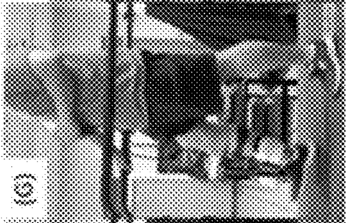
Figure 19H:
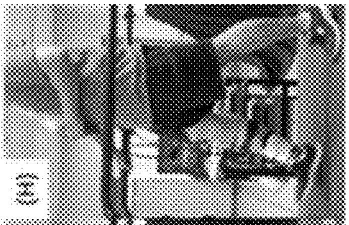
Figures 20A, 20B, 20C, 20D, 20E:
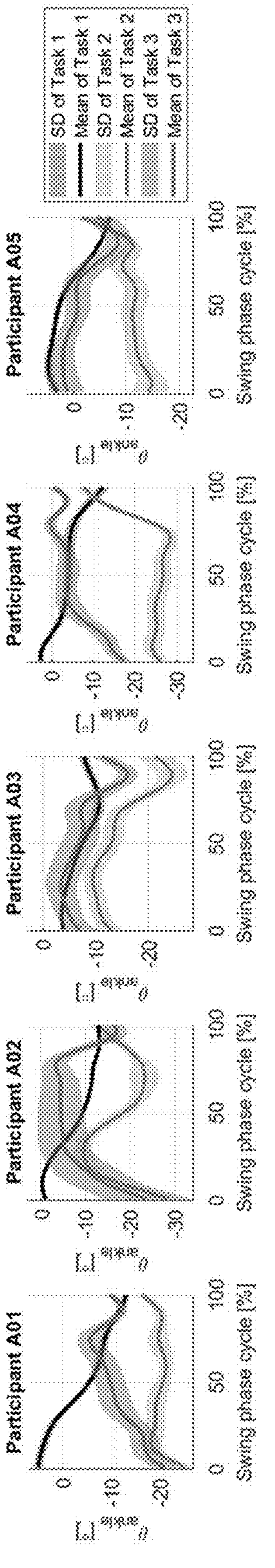
FIG. 20A-E are schematic diagrams according to implementations described herein.

Referring now to FIG. 18, graphs depicting ankle joint trajectory measurements and results from the GAPSO during the walking swing phase for each participant in Task 1 are provided. The gray and non-gray areas represent the swing phase and stance phase, respectively. The red and blue curves represent the online generated desired trajectories based on the virtual constraint and the measured trajectories by using the incremental encoder, respectively. In FIG. 18, the time-independent desired trajectories generated based on the virtual constraints and the measured trajectories during 10 exampled gait cycles in Task 1 are depicted for each participant. Given the current disclosure only focused on the swing phase, the desired ankle joint trajectories only exist in the gray areas and are represented by the red curves in FIG. 18 while the measured trajectories are represented by the blue curves. The accuracy of the online trajectory generation based on the virtual constraints was evaluated by calculating the averaged root mean square error (RMSE) values between the virtual constraint-calculated trajectories and measured trajectories during the 30 gait cycles in Task 1 for each participant. These averaged RMSE values are 1.49°, 1.26°, 2.12°, 1.83°, and 1.78° of participant A01, A02, . . . , A05, respectively. The mean and standard deviation (SD) of averaged RMSE values across participants are 1.70±0.33°. The small averaged RMSE value across gait cycles and participants indicates the high robustness of the designed virtual constraints.

Results of Control Performance

FIG. 19A-H demonstrates the snapshots of one swing phase during Task 3 on Participant A03, where (A)-(H) represent every 12.5% of the swing phase in the current gait cycle. Visually, the ankle joint's angular position is improved in the clockwise direction, especially from (E) to (H), when compared to results from Task 2. In FIG. 20A-E, the quantitative results of ankle joint real trajectories from 30 swing phases in Task 1, Task 2, and Task 3 on each participant are presented, where the black, blue, and red solid curves represent the mean value from 30 selected swing phases, while the black, blue, and red shadowed areas represent the SD in Task 1, Task 2, and Task 3, respectively. The individual TA muscle had different responses and the individual ankle joint had different trajectories due to three main reasons. First, the treadmill walking swing phase was the focus, where the ankle joint was in the air. According to the subjective walking habit, it is reasonable that each participant has a preferred and comfortable ankle joint trajectory during his or her walking swing phase even though the participant was asked to avoid volitional TA muscle contraction (make the ankle joint at rest) during each walking swing phase. Second, to get the measurements of angular position and velocity on the ankle joint, an ankle-foot brace with an incremental encoder was attached (same for all participants) in the experimental setup. The stabilization of the ankle-foot brace during the walking swing phase depended on many factors, including the size of individual shoes, the tightness of individual shoes, the stiffness and damping parameters of individual ankle joint with the ankle-foot brace, and so on. Third, due to the person-to-person variations, the threshold and saturation of FES pulse width were different between participants, and the control output FES pulse width were time-varying and different between participants. For each swing phase in FIG. 20A-E, the averaged $\theta_{ankle}$ is calculated, denoted as $\theta^{-}$ ankle, then the mean and SD values of 30 $\theta^{-}_{ankles}$ on each participant is calculated and shown in FIG. 44. The results show that the right ankle joint real dorsiflexion motion is significantly improved by using the proposed US-based DSC-DC control framework in Task 3 compared to the dorsiflexion motion with imitated drop foot in Task 2. However, compared to the normal gait in Task 1, some inconsistencies still existed even the proposed control framework was applied in Task 3, especially during the first half of the swing phase on Participant A01, A02, and A04.

Referring now to FIG. 21A-D, results of the sparse US echogenicity measurements (FIG. 21A) and the US echogenicity-derived muscle activation levels (FIG. 21B) in Tasks 1, 2, and 3, the non-delayed FES normalization from the US-based DSC-DC controller, (FIG. 21C) the continuous estimation of TA muscle activation from the proposed SDO (FIG. 21D) on Participant A03 are depicted. Each solid curve and shadowed area represent the mean and SD of the corresponding data from 30 swing phases and are normalized proportionally to the swing phase cycle (0-100%).

Figures 21A, 21B, 21C, 21D:
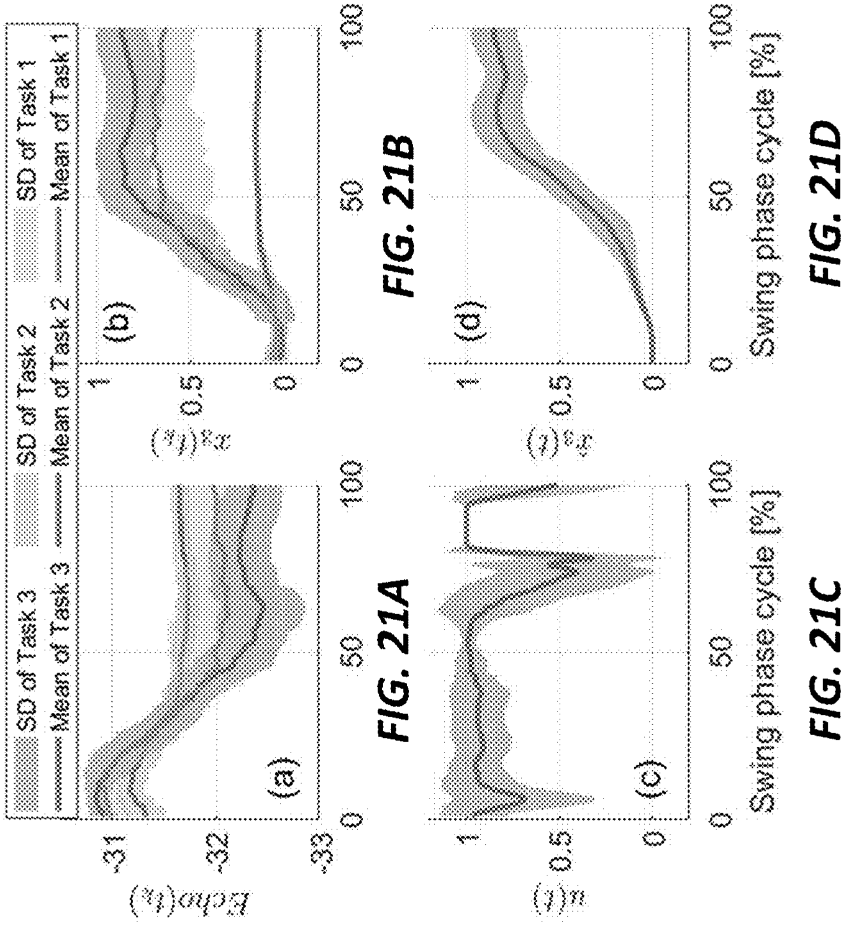
FIG. 21A-D are a schematic diagrams according to implementations described herein.

By taking Participant A03 as an example, the results of the sparse US echogenicity measurements and the US echogenicity-derived muscle activation levels in tasks 1, 2, and 3 are presented in FIG. 21A and FIG. 21B, respectively. Among these three tasks, FES was applied only in Task 3, so the input (normalized FES pulse width from the US-based DSC-DC control framework) and output signals (continuous muscle activation estimation given $T_{o}$=0.33 s for this participant and $\gamma$=20) of the SDO are presented in FIG. 21C and FIG. 21D, respectively. In each subplot, the mean and SD of each signal from 30 swing phases are normalized proportionally to the swing phase cycle (0-100%). Results in FIG. 21A and FIG. 21B indicate that muscle activation levels in Task 2 are much lower when compared to those in Task 1 and Task 3.

Figure 22A:
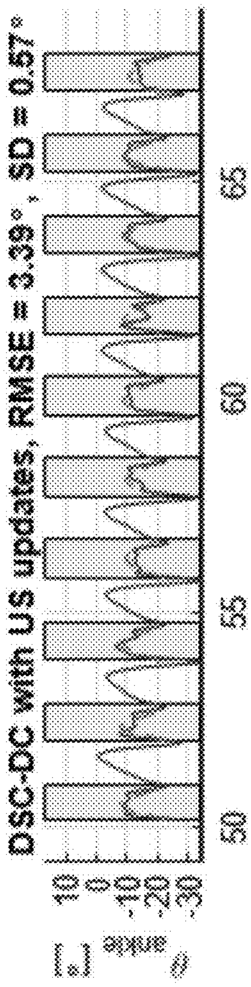
FIGS. 22A and 22B are schematic diagrams according to implementations described herein.
Figure 22B:
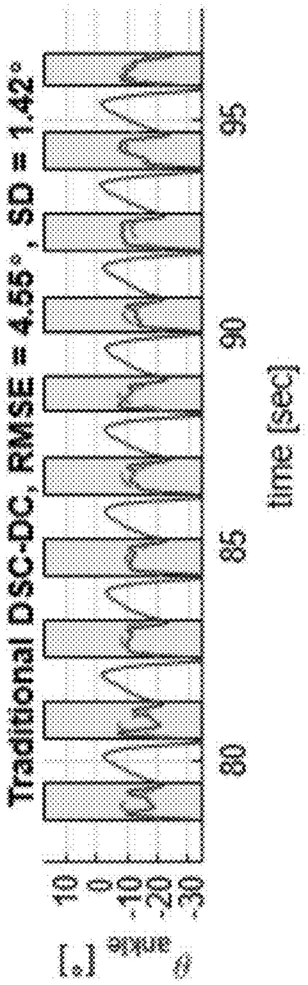

The experimental results for the trajectory tracking performance from a representative participant are presented in FIG. 22A-B, where data were obtained from 10 gait cycles in both Task 3 and Task 4. The dashed red and solid blue curves respectively represent the desired (generated online based on the virtual constraints) and actual (measured by the encoder) trajectories. When the US-based DSC-DC controller was applied, the best 10 successive gait cycles from this participant result in the RMSE of 3.39 0.57°, while when the traditional DSC-DC controller was applied, the best 10 successive gait cycles from this participant result in the RMSE of 4.55 1.42°. For the RMSE values from the corresponding 10 gait cycles shown in FIG. 22A-B, a two-sample paired t-test was performed to determine if the differences in the criteria were statistically significant at a 95% confidence level. The statistical analysis determined that the US-based DSC-DC controller statistically outperformed the traditional DSC-DC controller in the RMSE values ($p<0.001$). To further evaluate the controller performance throughout the 2-minute walking experiments in both Task 3 and Task 4, results of swing phases in the first and last 20 gait cycles within each 2-minute trial were compared and analyzed, denoted as single-task evaluation.

Referring now to FIG. 22A-B, experimental results of the trajectory tracking performance from 10 gait cycles by using both the US-based DSC-DC and traditional DSC-DC controllers on Participant A03. Results show the desired (dashed red curves) and actual (solid blue curves) trajectories during the swing phases.

Figure 23A:
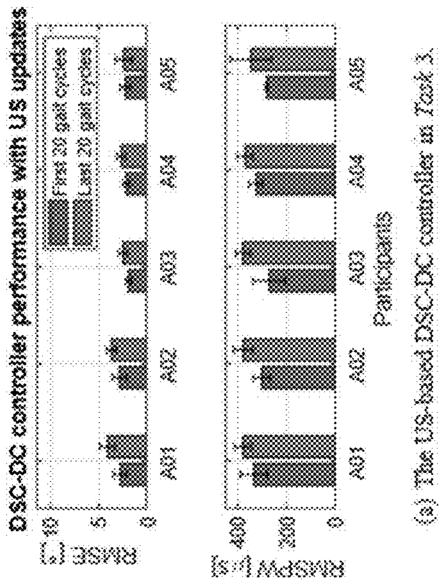
FIGS. 23A and 23B are schematic diagrams according to implementations described herein.
Figure 23B:
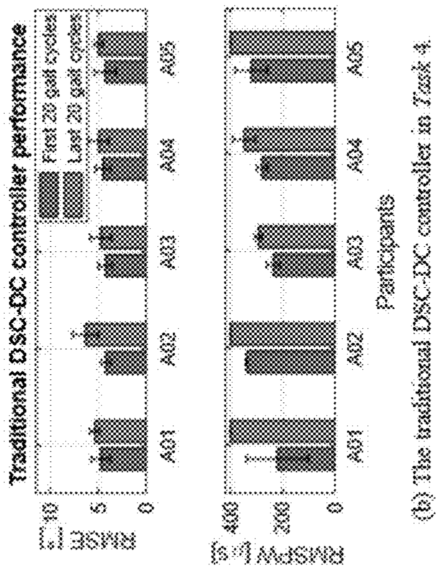

As shown in FIG. 23A-B, the mean and SD values of the ankle joint trajectory tracking RMSE and the mean and SD values of the root mean square pulse width (RMSPW) across the first and last 20 swing phases in Task 3 and Task 4 on each participant are depicted, respectively. When either the US-based DSC-DC or the traditional DSC-DC control framework was used, the trajectory tracking RMSE's mean value across the first 20 swing phases was lower than that across the last 20 swing phases for each participant, indicating the average ankle joint trajectory tracking performance in the first 20 gait cycles was better than the average of the last 20 gait cycles. Meanwhile, the RMSPW's mean value across the last 20 swing phases was higher than that across the first 20 swing phases for each participant, which implies that at the end of the 2-minute walking period, the FES-elicited muscle fatigue resulted in higher stimulation intensity but deteriorated the joint trajectory tracking performance. To demonstrate the advantages of the proposed US-based DSC-DC control framework over the traditional DSC-DC control framework, results of the ankle joint trajectory tracking RMSE and TA muscle stimulation RMSPW on the same participant with different controllers were compared. Given that the FES-evoked muscle fatigue is not the focus of the current disclosure, only results from the first 20 gait cycles in FIGS. 23 (*a*) and (*b*) were compared.

Figure 10A:
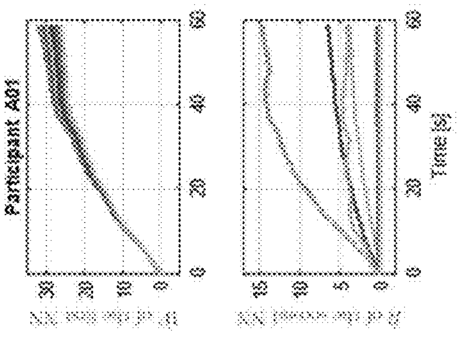
FIG. 10A-E is a schematic diagram according to implementations described herein.
Figure 10B:
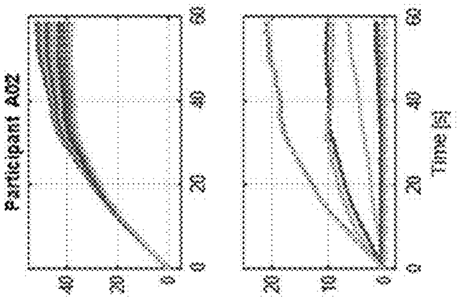
Figure 10C:
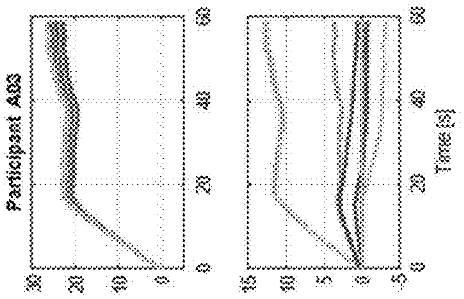
Figure 10D:
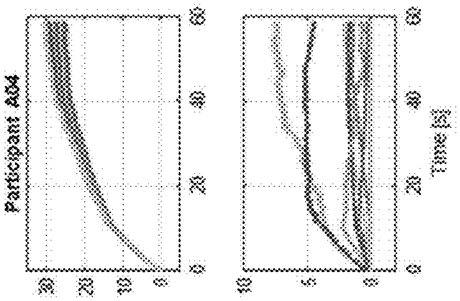
Figure 10E:
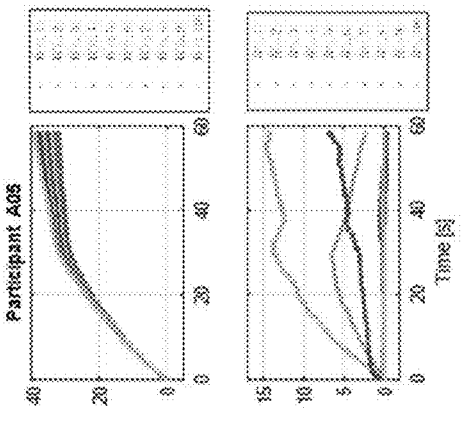
Figure 11:
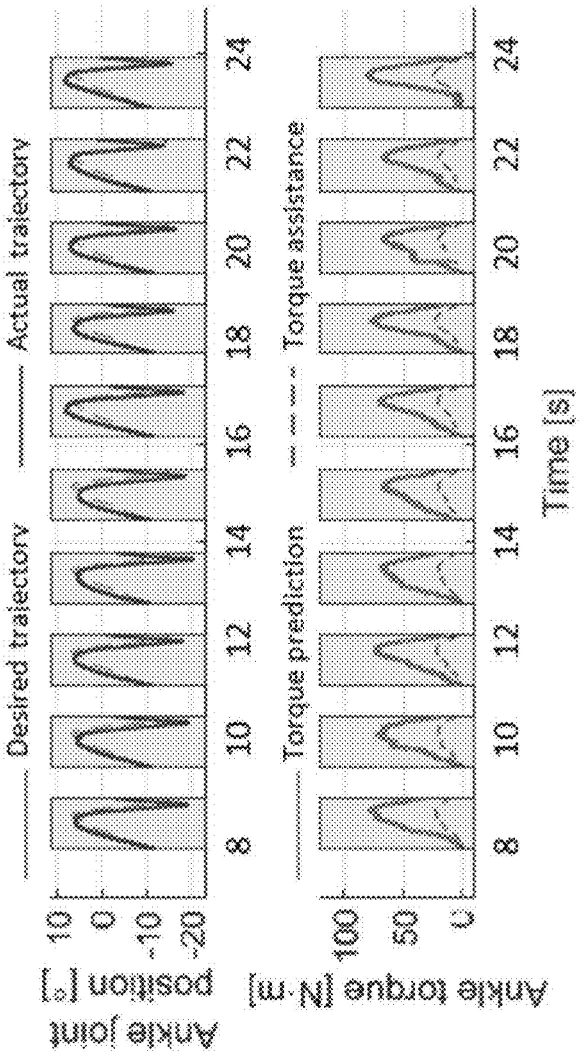
FIG. 11 is a schematic diagram according to implementations described herein.
Figure 24A:
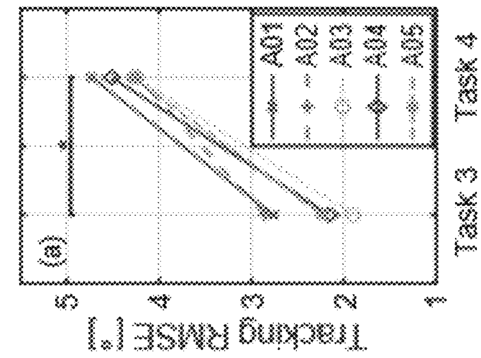
FIGS. 24A and 24B are schematic diagrams according to implementations described herein.
Figure 24B:
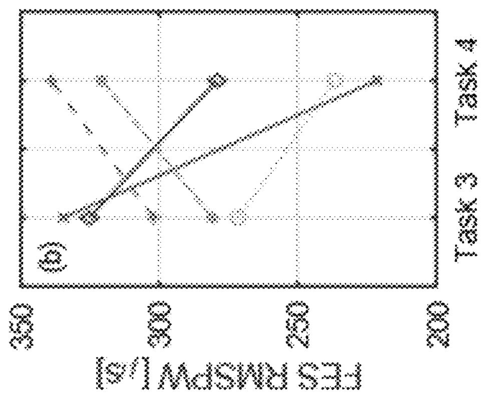

FIG. 24A-B show the mean trajectory tracking RMSE and mean FES RMSPW across those 20 swing cycles in Task 3 and Task 4 for each participant. A paired t-test was used to determine if the differences between Task 3 and Task 4 were statistically significant at a 95% confidence level across the five participants. The results in FIG. 10A show that the trajectory tracking RMSE values were significantly reduced by 46.52% 7.99% ($p<0.001$) when the US-based DSC-DC controller was applied, compared to those when the traditional DSC-DC controller was applied. Similarly, comparison results of the TA muscle stimulation RMSPW are also presented in FIG. 24B. However, no statistically significant difference was observed for the RMSPW values between Task 3 and Task 4 across the five participants. The US-based DSC-DC controller thus improves tracking performance without the need for increased FES intensity. Lastly, the robustness of the proposed US-based DSC-DC controller was evaluated by comparing the control performance in Task 3 and Task 5. To avoid the effect of FES-elicited muscle fatigue, data from the first 20 gait cycles of both tasks was used. FIG. 25 shows the results of plantarflexion stimulation disturbance rejection using the proposed US-based DSC-DC controller in the first 10 swing phases out of 20. During the treadmill walking in Task 5, with the motivation of the co-contraction characteristic in the drop foot syndrome, the ankle joint plantarflexion disturbance was simulated by applying a step FES input (frequency of 33 Hz, current amplitude of 25 mA, and pulse width of 100 pts) of 500 ms on the medial and lateral gastrocnemius muscles every time when the gait cycle entered the swing phase.

Figure 25A:
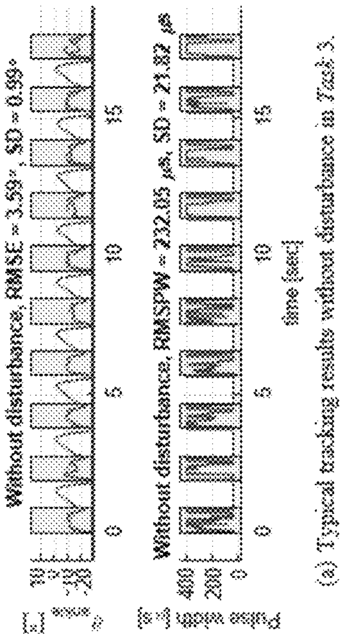
FIGS. 25A and 25B are schematic diagrams according to implementations described herein.
Figure 25B:
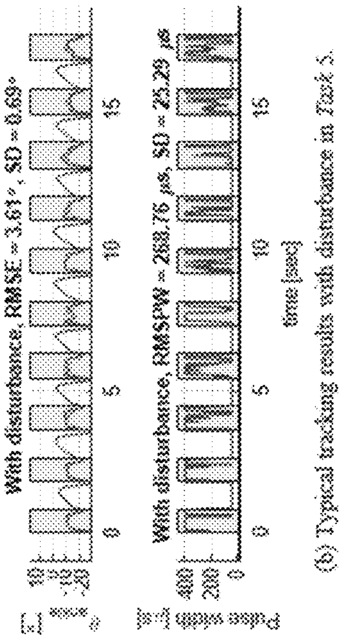

Referring now to FIG. 25A and FIG. 25B, comparison results of the ankle dorsiflexion trajectory tracking RMSE and FES RMSPW between Task 3 and Task 4 are provided. Each data point represents the mean value of the tracking RMSE or FES RMSPW across the first 20 swing cycles in each task on each individual participant. Asterisk * represents the significant difference level at $p<0.001$. It is observed that an effective disturbance rejection is obtained through the proposed controller in FIG. 25 (*b*), where the trajectory tracking RMSE values (3.61±0.69°) are comparable to the situation without any disturbance (3.59±0.99°) in FIG. 25 (*a*). However, the RMSPW values (268.76±25.29 μs) when applying the disturbance are significantly higher than the situation (232.05±21.82 μs) without any disturbance ($p<0.001$). Similarly, the mean and SD values of RMSE and RMSPW across the first 20 gait cycles with and without the plantarflexion disturbance on each participant are summarized in FIG. 45. Overall, the proposed US-based DSC-DC controller still achieved a comparative ankle joint trajectory tracking performance even though a plantarflexion disturbance was added, which implied an effective disturbance rejection of the proposed control framework across these five participants.

The purpose of using US imaging in the current disclosure was to measure the TA muscle activation level during FES, and this measurement was used as a feedback signal for the closed-loop control of the FES-elicited ankle joint neuromuscular system. US imaging directly visualizes the muscle contraction during FES and thus can monitor the muscle activation levels. It would thus act as a robust alternative to sEMG, which is often poorly suited due to interference from stimulation artifacts and cross-talk from adjacent muscles. However, US imaging for FES control is yet to be clinically translated and its advantages over sEMG must be validated in the future. That said, the real focus of the disclosure was not really to show an improvement of US over sEMG but to show given the potential advantages of US, how can one integrate US in closed-loop FES system control. It is true that the current US systems are more expensive and bulky than an sEMG system, and the portability of the US transducer will be critical for clinical translation of US-based drop foot technology. During the walking experiments on the treadmill, the experimental results showed that the US transducer was stabilized onto the targeted muscle steadily throughout the walking tasks (as can be seen in the newly added video demonstrations). In recently years, efforts are being made to make US imaging devices wearable [45], [61], [62], which may allow their viable integration in FES systems. Nevertheless, the comparison between the use of US imaging and sEMG signals in the closed-loop FES control problem is fairly important to further evaluate the contributions of using our proposed control framework, which will be an interesting research direction in future work. Indeed, EMG offers muscle activation at a higher frequency and our recent research [39], [41], [59] has even shown a benefit of combining US imaging, which provides mechanical information (muscle contractility) with sEMG during ankle dorsiflexion, where its electrical information can be complementary to US signals. Similar opportunity exists to combine sEMG and US for FES control and will be pursued in our future work.

The treadmill walking speed in the current disclosure was selected as 0.6 m/s, and minimal testing for walking with faster speeds due to the targeted clinical population being those with drop foot syndrome who usually have slower walking speeds. The following implications can be inferred. Firstly, the faster speeds will change the normal gait patterns, including the shank and thigh orientations and angular velocities, as well as the ankle joint trajectory during the swing phases, so the parameters need to be re-determined by using GAPSO in the virtual constraints. Secondly, given that the current US echogenicity measurement is sampled at 7.8 Hz, the faster walking speeds will shorten the time duration of the swing phase, thus reducing the available US echogenicity samples during the swing phase. These issues need to be addressed in the future US-based FES control design for faster walking speeds. Although the two-dimensional US imaging applied in this disclosure could visualize the skeletal muscle's architectural features from the superficial to the deep layers, it only provides information from a single plane, which might be prone to visualization errors for the targeted region of interest due to the lack of muscle depth information in the third dimension [63]. In particular, dynamic muscle contraction, including concentric and eccentric contraction, could easily cause squeeze, stretch, or overlap of muscle fascicles, and the capture of these deformations are very challenging by using two-dimensional US imaging. To address this challenge, three-dimensional US imaging has been investigated in recent years [64]. However, few studies have assessed the efficacy of real-time two-dimensional US imaging in the closed-loop control of FES systems, not to mention the real-time three-dimensional US imaging. Actually, this sort of problem is very common even for recently developed high-density sEMG (HD-sEMG) technology, where a plane of electrical information (a plane of length and width) at each time instant is provided, but HD-sEMG cannot be used to measure deeply located muscles.

There are still some limitations in the current disclosure. The first one is that only participants without any neurological disorders were included in this disclosure. Although they were asked to simulate the drop foot syndrome during the treadmill walking, they cannot completely avoid the volitional dorsiflexion motion during the swing phase and fully relax their foot, which was noticeable from the blue curves in FIG. 20A-E. Therefore, further evaluations of the proposed control framework on individuals with drop foot impairments are necessary in the next step. The second limitation of the applying US imaging was the low sample rate of 7.8 Hz, which was determined by the US machine in this disclosure. Different sampling frequency rates for US data and sEMG data are due to different data acquisition mechanisms. The US data contains high dimensional signals (128 channels for the US transducer used in this disclosure), compared to a one-dimensional EMG signal (one channel per sensor). Instead, the raw radio frequency data (usually binary-type data) may be transferred to 2D images, known as beamforming approach [60]. This beamforming procedure needs a large amount of computation and is time-consuming, which is the main reason that the US echogenicity signals can only be provided at a low-frequency rate. Transmission delays due to the use of the User Datagram Protocol (UDP) between two computer systems, e.g., the US machine with graphics processing unit (GPU) for online beamforming and US echogenicity calculation and the host computer running Simulink for the closed-loop control, is another reason for low computation rates for US imaging. As for the US echogenicity computation on the US machine with GPU as mentioned in (28) and the muscle activation measurement calculation in (29), they are almost instantaneous with computation time less than 1 ms. Nevertheless, multiple options could be used to possibly increase the US sample rate. Firstly, 128 channels were used to image the TA muscle and obtain US echogenicity from beamformed data that were collected from all 128 channels. The reduction of the channel number would be helpful to increase the US sample rate, but could result in lower SNR. Secondly, the depth of US imaging is set as 40 mm to capture the entire region of the TA muscle. The reduction of the depth could be another option, but could result in cropped region of the TA muscle. Thirdly, applying more advanced and time-efficient beamforming algorithms or more powerful graphics processing unit could also be helpful.

A US imaging-derived signal (echogenicity) is used as an indicator of the FES-induced muscle activation and designed an FES controller that includes both the continuous kinematic and the lower-sampled US imaging-derived activation measurements. An SDO was proposed to continuously estimate the US imaging-derived muscle activation levels during the stimulation, while a DC term was used to deal with the input delay in the muscle activation dynamics. The Lyapunov-Krasovskii stability analysis was performed to prove the convergence of the trajectory tracking error was SGUUB. This is the first disclosure that integrates the real-time US imaging in the closed-loop FES control. The proposed US-based DSC-DC controller was experimentally validated during the walking swing phase on a treadmill. Experimental results showed that the dorsiflexion trajectory tracking performance was significantly improved by incorporating the US-imaging signals. Future work will focus on investigation and evaluation of the proposed controller on persons with drop foot disorders, as well as the comparison between the use of US imaging and sEMG signals in the closed-loop FES control problem.

Functional electrical stimulation (FES) is a potential neurorehabilitative intervention to enable functional movements in persons with neurological conditions that cause mobility impairments. However, the quick onset of muscle fatigue during FES is a significant challenge for sustaining the desired functional movements for more extended periods. Therefore, a considerable interest still exists in the development of sensing techniques that reliably measure FES-induced muscle fatigue. In accordance with some embodiments of the present disclosure, an ultrasound (US) imaging-derived echogenicity signal is used as an indicator of FES-induced muscle fatigue. The inventors hypothesized that the US-derived echogenicity signal is sensitive to FES-induced muscle fatigue under isometric and dynamic muscle contraction conditions. Eight non-disabled participants participated in the experiments, where FES electrodes were applied on their tibialis anterior (TA) muscles. During a fatigue protocol under either isometric and dynamic ankle dorsiflexion conditions, the isometric dorsiflexion torque or dynamic dorsiflexion angle on the ankle joint, US echogenicity signals from TA muscle, and the applied stimulation intensity were synchronously collected. The experimental results showed an exponential reduction in the US echogenicity relative change (ERC) as the fatigue progressed under the isometric ($R2=0.891\pm0.081$) and dynamic ($R2=0.858\pm0.065$) conditions. The experimental results also implied a strong linear relationship between US ERC and TA muscle fatigue benchmark (dorsiflexion torque or angle amplitude), with R2 values of $0.840\pm0.054$ and $0.794\pm0.065$ under isometric and dynamic conditions, respectively. The findings indicate that the US echogenicity signal is a computationally efficient signal that strongly represents FES-induced muscle fatigue. Its real-time implementation to detect fatigue can facilitate an FES closed-loop controller design that considers the FES-induced muscle fatigue.

Neurological injuries, like a spinal cord injury (SCI) [2] and stroke [3], usually result in paraplegia or hemiplegia, disrupting both physical and emotional well-beings Without physical assistance from mobility aids or a neuroprosthetic intervention, the mobility impairment increases social isolation, anxiety, and depression. Functional electrical stimulation (FES), an artificial technique that applies low-amplitude electrical potentials across the paralyzed skeletal muscle belly or peripheral nerve, can reanimate the walking function and help restore mobility. Since the earlier demonstrations of FES to correct drop foot [5] and [6], recent studies [7-12] investigated its orthotic effects on a larger clinical population. Additionally, FES can provide supplementary benefits, including the improvement in muscle tone and size, muscle strength, blood flow, and a reduction in muscle spasticity and disuse osteoporosis. Despite the efficacy and benefits of FES, the rapid onset of muscle fatigue is a major limitation. Due to the non-selective stimulation nature of FES, peripheral motor units are synchronously activated and discharged, causing the stimulated muscle to fatigue easily. The induced fatigue results in the deterioration of the muscle contraction force generation, causing a rapid loss of FES control effectiveness [13]. To reduce the FES-induced muscle fatigue, multiple studies have investigated the spatially distributed sequential stimulation pattern [14-16], where a single stimulation site distributes the center of the electrical field over a wide area by using an array of surface electrodes. In addition, Downey et al. [17] showed that the use of multi-channel asynchronous stimulation reduced muscle fatigue compared to conventional single-channel stimulation. Later in [18], a closed-loop controller for asynchronous FES was shown to extend the duration of functional movements. Despite the advances in stimulation protocols and new closed-loop FES controllers, non-invasive evaluation and characterization of the FES-induced muscle fatigue are lacking. Fatigue measurement methods are important for quantifying the fatigue effects on the neuromusculoskeletal dynamics and for an effective FES control design. Efforts in indirectly measuring fatigue include, but are not limited to, tetanic contraction force measurement [19], electromyography (EMG)/surface electromyography (sEMG) [20-22], mechanomyography [23], near-infrared spectroscopy [24-26], and phosphorus nuclear magnetic resonance [27]. Among these technologies, sEMG is the most well-developed and convenient non-invasive methodology to assess peripheral muscle fatigue. Although [28-30] report successful extraction of volitional or evoked sEMG during FES, the analysis and evaluation of the EMG signals during FES is still challenging. The challenges are mainly due to the FES-induced contractions cluttering and masking the pure sEMG signals [31,32], interference and cross talk from adjacent muscles [21], and the inability to measure the sEMG signals from deeply seated muscles [33]. Recently, ultrasound (US) imaging technique, known as sonomyography, has been investigated to qualitative or quantitatively assess muscle fatigue for volitional and FES-induced muscle contraction as an alternative methodology to sEMG. Due to a relatively high spatial and temporal resolution, the US images provide direct visualization of the muscle deformations during the implementation of FES. These muscle deformations can be quantified to obtain a comprehensive measure that reflects the fatigue effect. Shi et al.[34] used muscle thickness, extracted from cross-sectional US images, to characterize the volitionally induced fatigue in the biceps brachii muscles. Similarly, Witte et al. [35] applied US strain imaging to capture the elastic and viscoelastic-like modifications in the 3rd flexor digitorum superficialis muscle after a voluntary fatiguing exercise. Sheng et al. [36,37] investigated an adaptive speckle tracking algorithm for determining strain changes in the quadriceps muscle during the FES-induced muscle fatigue protocol under isometric knee extensions. The aforementioned US imaging-related studies for assessing muscle fatigue primarily investigated isometric muscle contractions. Few studies have investigated FES-induced muscle fatigue characteristics under dynamic joint movement conditions. Additionally, the aforementioned studies reported their results based on offline processed US imaging data, since deriving fatigue-relevant features from US imaging is generally computationally intensive. The high computation cost significantly limits the use of US imaging to evaluate muscle fatigue in real-time.

Inspired by recent studies in US imaging-derived echogenicity signals to predict motion intent or voluntary effort in the forearm and ankle muscles [38,39], preliminary results of using post-processed US echogenicity signal to assess the FES-induced muscle fatigue have been reported in [1]. The preliminary results were extended in [1] to a larger participant group and investigated the feasibility of using the online-processed US echogenicity to quantitatively assess FES-induced muscle fatigue. Specifically, the tibialis anterior (TA) muscle was selected to reveal the fatigue-indicating performance of US echogenicity under both isometric and dynamic ankle dorsiflexion movements, where dorsiflexion force/angular position (iso-metric/dynamic conditions), TA muscle's US echogenicity, and FES intensity were synchronously collected during the muscle fatigue progression. A comprehensive correlation analysis between the temporal US echogenicity relative change (ERC) and TA muscle fatigue progression (decay of dorsiflexion force or angle during isometric or dynamic conditions) was performed to assess the muscle contractility during fatigue progression. It was hypothesized that there exists a nonlinear relationship between the US ERC and the FES duration (contraction cycles), as well as a linear relationship between the US ERC and the decay of dorsiflexion force or angle. Furthermore, the performance of US ERC as a surrogate metric of muscle fatigue was compared to the US tissue strain as reported in [36,37].

The online US image beam-forming and echogenicity calculations were implemented on the US machine according to the series steps of "line-by-line beamforming—image cropping—US echogenicity calculation—data transfer to Simulink", which required a lot of computational capability and time to make this online US echogenicity stream available. During the muscle fatigue progression, while the US echogenicity transmission was running online, raw RF data were also saved for US imaging visualization in a post-hoc way. To reduce the computation and data storage burden of the US machine, during both isometric and dynamic fatigue progressions, US echogenicity signals and raw RF data were collected synchronously with signals from the load cell or the encoder during the first second of every 4 stimulation cycles, as illustrated in FIG. 26.

Figure 26A:
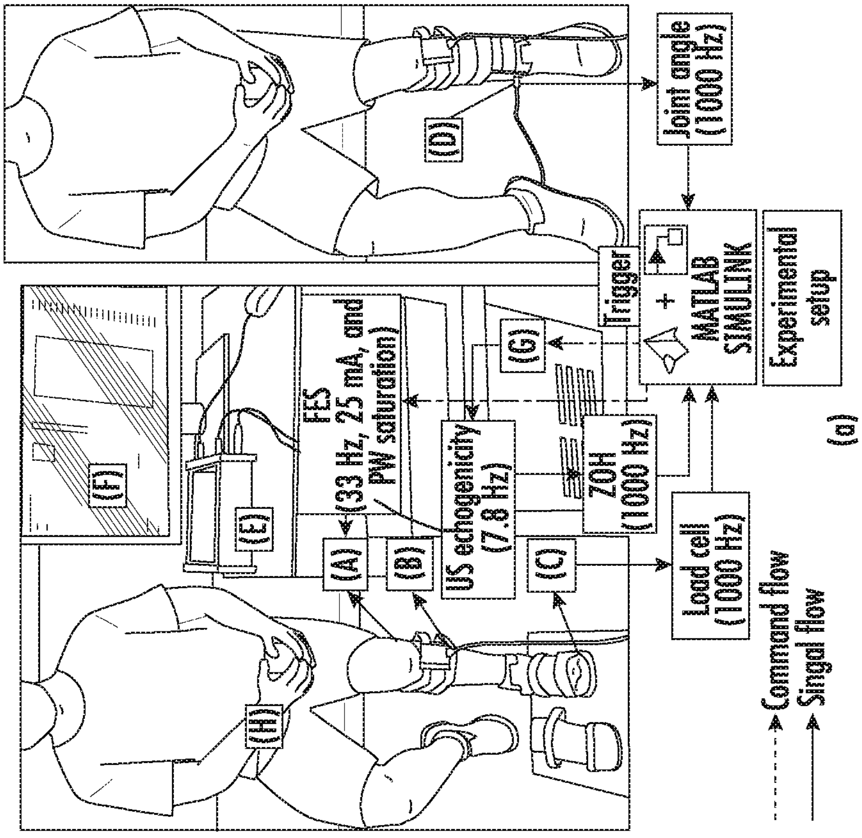
FIGS. 26A and 26B are schematic diagrams according to implementations described herein.
Figure 26B:
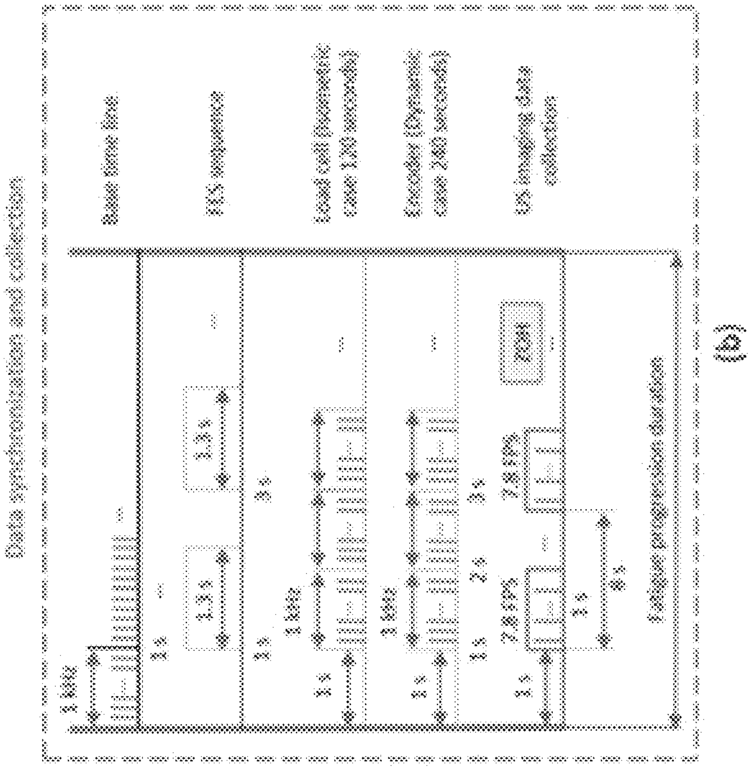

In particular, FIG. 26A depicts: (a) experimental setup of the isometric (left) and dynamic (dynamic) ankle joint dorsi-flexion by using FES. A—FES electrode pads, B—Prodigy US transducer, C—Load cell platform, D—Incremental encoder, E—FES stimulator, F—Monitor showing B-mode US imaging, G—Prodigy US machine, H—Safety stop button. FIG. 26B depicts data synchronization and collection among multiple channels. Preliminary results showed the above online steps could run around 7.8 times per second, so the online US echogenicity was sent out from the US machine at a frequency of 7.8 Hz. Due to the use of a zero-order-hold function in Simulink, the US echogenicity data collection was still sampled and collected at 1000 Hz, but without changes during two successively generated values from the US machine. The aforementioned experimental and data collection procedures were applied on the left ankle joint of each participant.

Data Processing and Analysis

Figure 27:
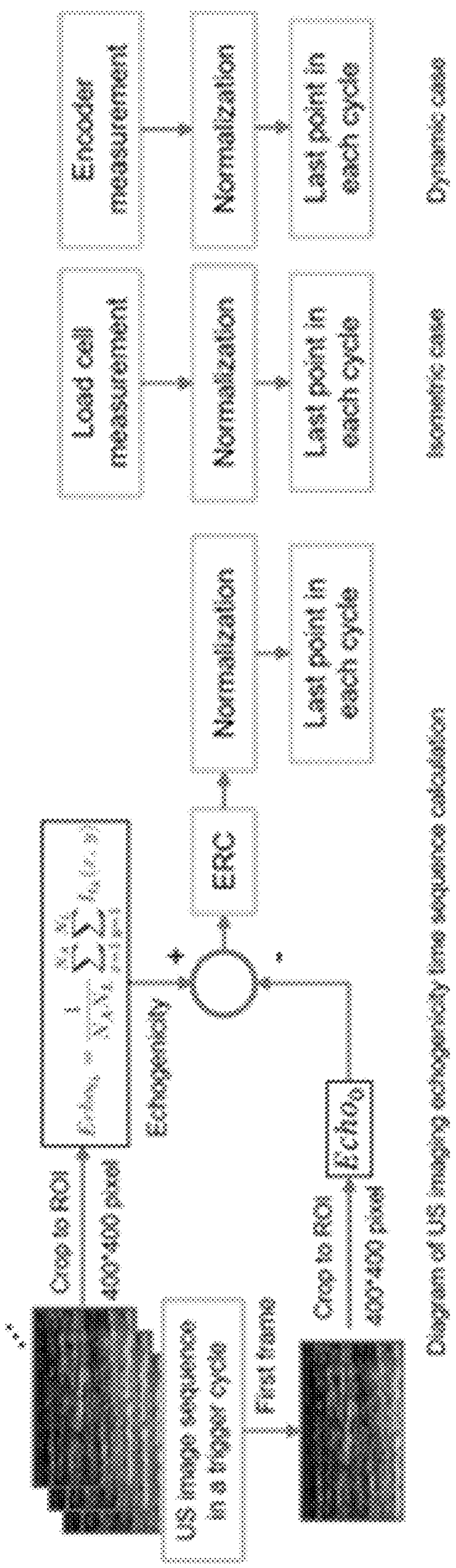
FIG. 27 is a schematic diagram according to implementations described herein.

The ankle dorsiflexion torque and angle measurements were low-pass filtered by a 4th-order Butterworth filter with a cutoff frequency of 6 Hz. According to the data synchronization in FIG. 1*b*, the dorsiflexion torque signal during the isometric condition and dorsiflexion angle during the dynamic condition were aligned with the period when FES was on, and the last data point from each stimulation cycle was selected and normalized to the peak value across all stimulation cycles for further analysis. Similarly, the dorsiflexion torque or dorsiflexion angle signals were aligned with the period when the US imaging trigger was on, and the last data point from each trigger cycle was selected and normalized to the peak value across all US imaging trigger cycles for further analysis. The detailed data processing diagram is presented in FIG. 27.

The procedures for US imaging data processing are as follows. First, the raw RF data were beamformed online through the line-and-line beamforming algorithm. Then the logarithmic imaging intensity compression was performed to get the envelope of the demodulated RF data. By normalizing the envelope of each pixel between 0 to 255, the B-mode US image at the current frame was generated. A median filter and non-local means denoising [42] were applied to spatially filter each B-mode image. At last, the averaged gray-scaled echo intensity within the region of interest (ROI) of 400 pixel×400

$$\text{Echo}_{t_k} = \frac{1}{N_A N_L}\sum_{x=1}^{N_A}\sum_{y=1}^{N_L} I_{t_k}(x, y) \tag{62}$$

where $N_A$, $N_L$ represent the pixel numbers along with axial and lateral directions, respectively. $I_{t_k}(x,y)$ represents the US intensity information at the pixel location (x,y) on the image at $t_k$ instant from the normalized logarithmic imaging intensity compression signals. As a consequence, the 2D image time sequence was transferred to a 1D signal time sequence. Visually, each $I_{t_k}(x,y)$ presents the brightness of that pixel at the location of (x,y) on the 2D map. Thus, the calculated echogenicity signal presents an overall brightness within the ROI. Note that although the US imaging beamforming and echogenicity calculation were based on the online manner, the updating frequency was fairly low (7.8 Hz from preliminary results) due to the computation time and communication delay between the US machine and Simulink real-time program. Therefore, a zero-order-hold function was used in the real-time program to collect the online calculated US echogenicity at 1000 Hz. The echogenicity time sequence within the same stimulation cycle was subtracted by the echogenicity of the first image from the same cycle, which was defined as the ERC within the same cycle. Similarly, the last data point of ERC in each trigger cycle was selected and normalized to the peak ERC throughout all trigger cycles. Given the FES-induced fatigue progression protocol, the last point of ERC corresponded to a sub-maximal dorsiflexion force or dorsiflexion angle; therefore, the aligned last data point of dorsiflexion force or angle during each FES cycle and the aligned last data point of ERC during each US imaging trigger cycle were selected to characterize the muscle contractility during fatigue progressions. As a consequence, during the isometric fatigue progression, 60 samples from dorsiflexion forces and 15 samples from ERC were obtained, while during the dynamic fatigue progression, 120 samples from the dorsiflexion angles and 30 samples from ERC were obtained. According to the muscle fatigue dynamics and its solution mentioned in [13], an exponential regression model was used to fit the curve between the normalized sub-maximal dorsiflexion force or angle and the index number of contractions (i=1, 2, . . . , 60/i=1, 2, . . . , 120), as well as the curve between the normalized sub-maximal ERC and the index number of contractions (i=4, 8, . . . , 60/i=4, 8, . . . , 120). The coefficients of the exponential regression models were determined by using the Levenberg-Marquardt nonlinear least squares algorithm [43]. A linear regression model was used to fit the line between the normalized sub-maximal dorsiflexion torque/angle and the normalized sub-maximal US ERC. To evaluate the goodness of curve fittings, the coefficient of determination ($R^2$) of each regression model was also calculated as $$R^2 = \frac{\left(\sum_{i=1}^{N}(T_i - \overline{T})\left(\hat{T}_i - \overline{\hat{T}}\right)\right)^2}{\sum_{i=1}^{N}(T_i - \overline{T})^2 \sum_{i=1}^{N}\left(\hat{T}_i - \overline{\hat{T}}\right)^{2'}} \tag{63}$$

The coefficients of exponential regression models and corresponding R2 values are listed in FIG. 47, where the upper (lower) half represents the regression model between dorsiflexion torque/angle normalization (ERC normalization) and contraction cycles.

Statistical Analysis

The normality of the targeted data sets was tested based on the Shapiro-Wilk parametric hypothesis test (SW test). Those data sets include coefficients and $R^2$ values of each exponential regression model and linear regression model under either isometric or dynamic conditions across all eight participants, as well as the computation times of the US echogenicity and axial strain per image frame. According to the results from SW test, a paired t-test (normal distribution) or a Wilcoxon signed rank test (not normal distribution) was applied to analyze if there was significant difference between two independent groups. To be more specific, for the exponential and linear regression models, the optimal coefficient values were compared to zero, and $R^2$ values were compared under isometric and dynamic conditions. As a comparative disclosure, the $R^2$ values between the normalized ERC and normalized sub-maximal torque under the isometric condition were compared to the results reported in [36] between the normalized maximal axial strain and normalized sub-maximal torque. In addition, the computation times of the US echogenicity and axial strain per image frame were also compared to determine if there was a significant difference between these two muscle fatigue indicators. For all statistical analysis, the significant difference level was set as $p<0.05$.

Individual Fes Pulse Width Threshold and Saturation Determination

Figure 28:
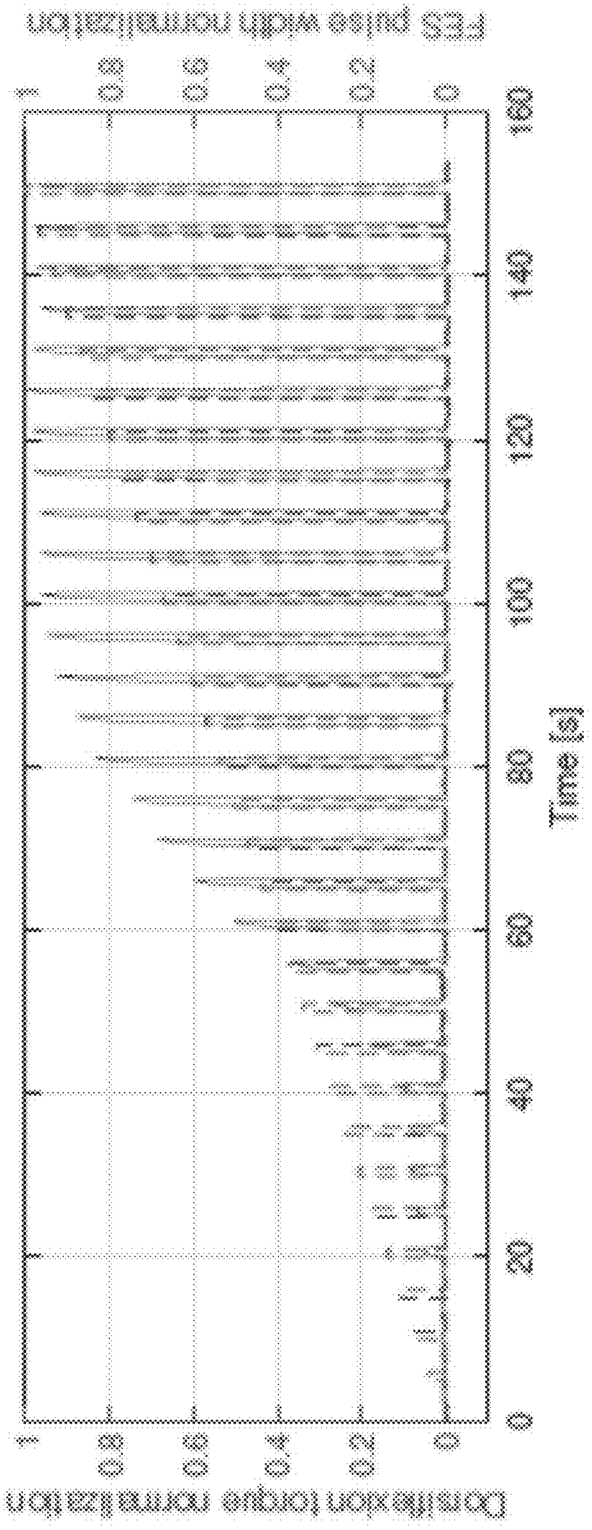
FIG. 28 is a schematic diagram according to implementations described herein.

The experimental results from the first task on Sub01 are presented in FIG. 28, where the monotonically increasing FES pulse width and ankle dorsiflexion torque are normalized to their corresponding peak values during the entire task. The threshold pulse width amplitude of each individual was taken as the amplitude that produced the first significant increase of the dorsiflexion torque, while the pulse width saturation was taken as the amplitude that no longer generated a significant increase of dorsiflexion torque. According to the dorsiflexion torque increase in FIG. 28, the pulse width threshold and saturation for Sub01 are around 100 μs and 420 μs, respectively. Similarly, the same determination approach was applied to all other participants, and the pulse width threshold and saturation values are summarized in FIG. 46.

TA Muscle Fatigue Effects on Isometric and Dynamic Ankle Dorsiflexion

Figure 29:
FIG. 29 is a schematic diagram according to implementations described herein.

Taking the FES-induced TA muscle fatigue under the dynamic condition on Participant Sub03 as an example, the qualitative evaluation of muscle contractility characteristics during the fatigue progression can be visualized in FIG. 29. The first and last frames of US imaging from every 4 stimulation cycles were selected and compared in each subplot of FIG. 29. According to the negative correlation between the echogenicity signals and muscle contraction levels in [39], the hyperechogenic (with higher gray-scaled values) and hypoechogenic (with lower gray-scaled values) US images represent less and more muscle contraction force, respectively. It is observed that with the increase of stimulation cycles, the last frame of US imaging becomes more hyperechogenic, which indicates the TA muscle force generation ability decreases. The 2D correlation coefficient between the presented two frames in each stimulation cycle was also calculated and shown in each subplot. A higher correlation coefficient represents smaller deformation of the targeted muscle, indicating less muscle contraction force generation. It is observed that the correlation coefficient increases along with the stimulation cycles, representing the reduced muscle force generation due to FES-induced muscle fatigue. A similar changing pattern of US imaging was also observed under the isometric and dynamic conditions of other participants. To evaluate the FES-induced fatigue, the reduction of dorsiflexion torque or angle was considered as the benchmark. Corresponding to the benchmark, the reduction of ERC during the muscle fatigue progression was observed. Remarkably, all signals show a monotonic decay trend with the muscle fatigue progression. The sub-maximal dorsiflexion torque reduces to 50% of the pre-fatigue capability after about 35 contraction cycles, while the sub-maximal dorsiflexion angle reduces to 50% of the pre-fatigue capability after about 30 contraction cycles. Additionally, after 60 stimulation cycles, the dorsiflexion torque and angle decayed to 39.2% and 31.2% of the pre-fatigue capacity under isometric and dynamic conditions, respectively. The results indicate that, with the same FES intensity and same muscle stimulation cycles, the fatigue levels of the TA muscle are similar under isometric and dynamic conditions. However, the participants reported that they feel more comfortable during the fatigue progression under the dynamic condition. Under both conditions, as the increase of muscle contraction cycles, the isometric dorsiflexion torque and dynamic dorsiflexion angle present a strong exponential decay. A strong exponential relationship is observed between the ERC normalization and the stimulation cycles for both isometric and dynamic conditions.

Implication of Us Echogenicity as a Fatigue Indicator

Figure 30:
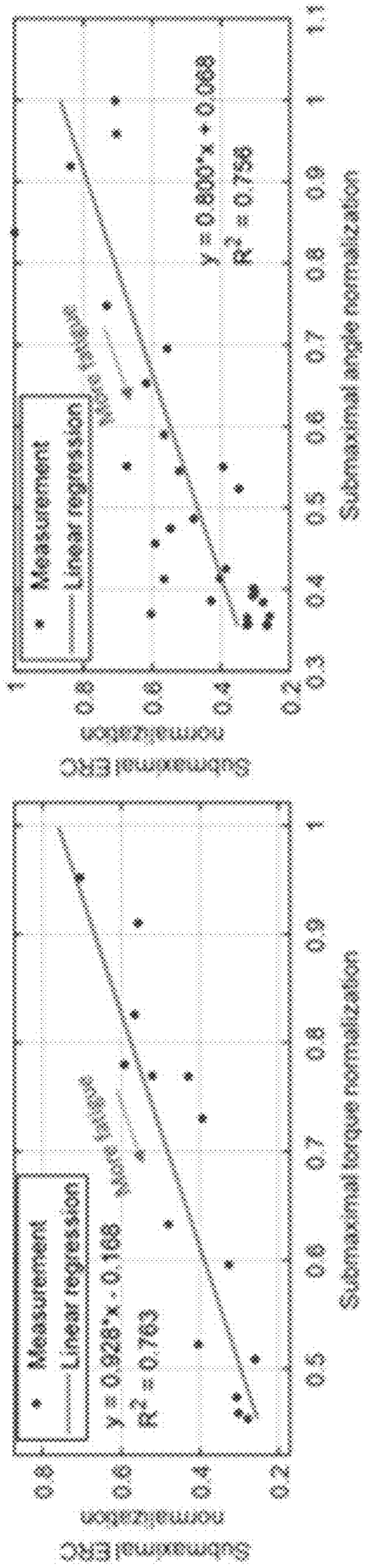
FIG. 30 is a schematic diagram according to implementations described herein.

FIG. 30 presents the representative scatter plots between the TA muscle's sub-maximal US ERC normalization and the sub-maximal dorsiflexion torque normalization/angle normalization under isometric/dynamic fatigue progression conditions, where the data were collected from Participant Sub05. The direction of decreasing dorsiflexion torque or angle corresponds to the fatigue progression direction, as labeled in FIG. 30. Through the linear regression model (the equations and $R^2$ values as shown in FIG. 30), strong linear relationships between the sub-maximal US ERC and the sub-maximal dorsiflexion torque/angle were observed with the p-value of each slope from the F-statistic less than $10^{-4}$, which indicates that US ERC is a reliable alternative fatigue indicator for each participant. A summary of $R^2$, slope with p-value, and y-intercept with p-value from the linear regression analysis under isometric and dynamic fatigue progression conditions on all eight participants is given in FIG. 48. The results show that the mean slope values under isometric and dynamic conditions are both close to 1, while the mean y-intercept values are close to 0. Overall, the $R^2$ values are 0.840±0.054 and 0.794±0.065 under the isometric and dynamic conditions. The statistical analysis shows that the $R^2$ values under the isometric condition are significantly higher than those under the dynamic condition (p-value=0.024). Therefore, the results imply that when using US ERC as the secondary fatigue indicator, the isometric scenario is likely to show significantly better fatigue-indicating performance than the dynamic scenario.

The US echogenicity signal as an online FES-induced muscle fatigue indicator was investigated for the first time under the isometric and dynamic ankle dorsiflexion movements in this disclosure. The experimental results on eight participants without any neurological disorders showed that the US ERC normalization was exponentially decreasing along with the muscle contraction cycles for both isometric (R2=0.891±0.081) and dynamic ($R^2$=0.858±0.065) conditions. Additionally, the results also showed strong linear relationships between the US ERC normalization and dorsiflexion torque normalization ($R^2$=0.840±0.054) or dorsiflexion angle normalization ($R^2$=0.794±0.065) during the muscle fatigue progression. Interpretation of results, potential improvements, and applications will be discussed in the following parts. In the experimental protocol, a zero-order-hold function was used to enable the data collection of the real-time US echogenicity signal at 1000 Hz. However, the US echogenicity update frequency was determined by the online imaging beamforming, processing, and gray-scaled analysis. In the current experimental setup and US imaging machine configurations, the online US echogenicity generation time was 127.9±7.8 ms for a single image frame, which resulted in a US echogenicity updating frequency of 7.8 Hz. Compared to the US strain imaging computation time per image frame, 368.7±7.2 ms [37], the computational load is significantly reduced by 65.3% ($p<0.001$) by using the US echogenicity as the FES-induced muscle fatigue indicator. Regarding the FES-induced muscle fatigue-indicating performance, the findings in [37] showed that under the isometric condition, the $R^2$ value of the linear regression model between sub-maximal mean (maximal) axial tissue strain normalization and sub-maximal joint torque normalization was 0.823±0.151 (0.850±0.165). A two-tail paired t-test did not show any significant difference between the $R^2$ values of the linear model by using US echogenicity and the $R^2$ values of the linear model by using US strain imaging. The advantages of using US echogenicity as a muscle fatigue indicator include (1) the relatively robust selection of the ROI due to the static nature, (2) no requirement of US image with higher resolution and clearly visualized architectural features, and (3) the significant reduction of calculation time for easier real-time implementation. Therefore, enough evidence implies that the US echogenicity has a comparable fatigue-indicating performance of FES-induced muscle fatigue as US strain imaging, but with a much lower computational intensity and a promising potential for online implementation for functional tasks, like drop-foot correction by using FES during walking.

The muscle force's, joint torque's or joint motion's decay during the FES-elicited muscle contraction has always been taken as a gold standard indicator for peripheral muscle fatigue, but measures of muscle force, joint torque, or joint motion usually require sophisticated hardware setup and only provide mechanical-type signals without showing any neuromuscular changes during the muscle fatigue progression. In addition, switching between indicator platforms is required to evaluate muscle fatigue for both isometric and dynamic conditions. Therefore, introducing an alternative non-invasive FES-induced muscle fatigue indicator that can be easily implemented for both isometric and dynamic tasks, with a simpler setup and in a real-time manner, is necessary. The real-time US echogenicity measurement facilitates a simplistic evaluation of the current muscle fatigue levels so that users can adjust the corresponding stimulation intensity to increase the FES-related rehabilitative training period or terminate the rehabilitative training if the muscle is too fatigued. Furthermore, the US echogenicity-indicated muscle fatigue will also be beneficial to advanced closed-loop FES controller design with the consideration of muscle fatigue. The US echogenicity signal is potentially sensitive to several factors, including the elevation angle between the transducer arm and the skin surface, the orientation angle between the transducer array and the skin surface, the relative sliding between the transducer array and the skin surface, and the pressure on the skin. To mitigate these factors, a customized 3D-printed US transducer holder, detailed in [39,40], and elaborate experimental operations were utilized. First of all, the US transducer beam was tightly bonded onto the arm of the rotation component of the holder, which guaranteed the elevation angle to be approximately 900, so the transducer was always perpendicular to the skin surface. Secondly, the US transducer was rotated to the cross-sectional direction to get a good view of the target TA muscle and then rotated to the longitudinal direction for real-time echogenicity data collection. Once the longitudinal direction was determined, no further rotation was conducted, so the orientation angle was set as the location where the transducer was at the longitudinal direction. Thirdly, Velcro straps were used to bond the base frame of the holder onto the skin tightly to avoid significant sliding of the US transducer, although there might be some squeezing of the TA muscle. Due to the compliant shape of the Velcro straps, when the TA muscle was bulging due to the stimulation, minimal transducer-to-skin pressure change was expected throughout each fatigue progression trial.

Figure 31:
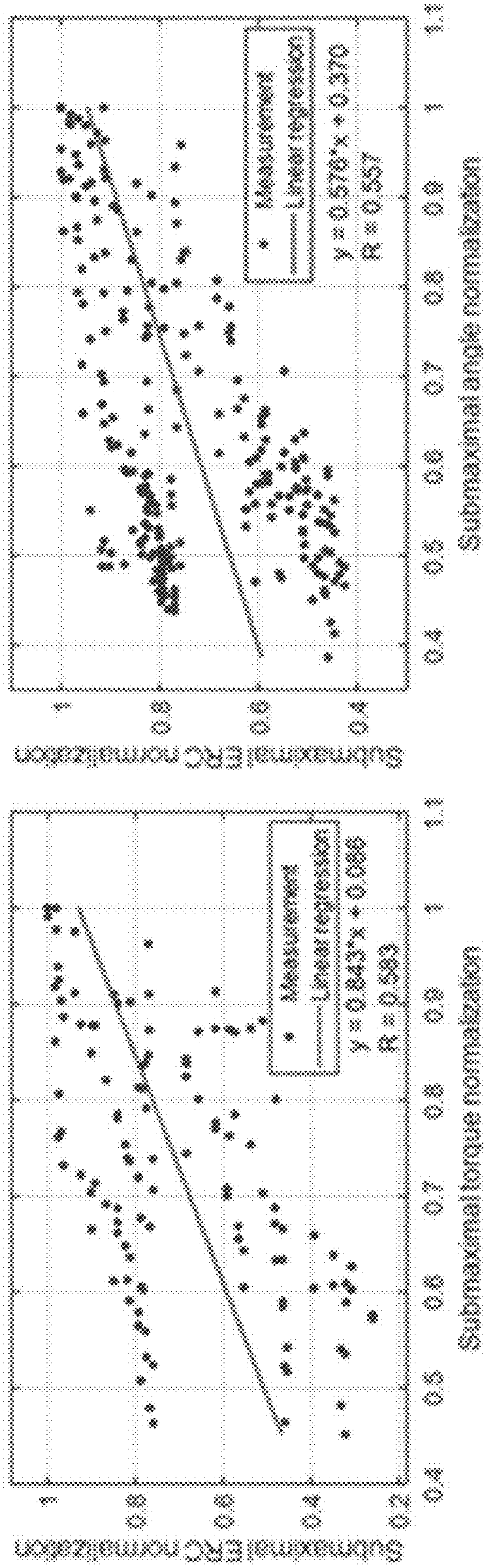
FIG. 31 is a schematic diagram according to implementations described herein.

To evaluate the generalization of using US echogenicity as an FES-induced muscle fatigue indicator, results from the individual participant as shown in FIG. 30 are summarized in FIG. 31. There are 120 data points (15 points from each of eight participants) and 240 data points (30 points from each of eight participants) for isometric and dynamic conditions, respectively. The linear regression equations and correlation coefficients are also labeled on the corresponding plots. From the F-statistic, the slope values for isometric and dynamic conditions are 0.843 and 0.576 with the p values of $5.52^{-13}$ and $9.19^{-22}$, respectively, while the y-intercept values are 0.086 and 0.370 with the p values of 0.38 and $1.76^{-19}$, respectively. It is observed that the correlation coefficient under the isometric condition is higher than that under the dynamic condition, which indicates the US echogenicity has a stronger correlation with the fatigue benchmark and potentially is a more accurate fatigue indicator when FES is applied under the isometric condition than the dynamic condition. The results in FIG. 31 showed a relatively high inter-subject variation of using US echogenicity as a muscle fatigue indicator under the application of FES in the present disclosure.

In the current disclosure, the use of temporal US echogenicity to quantitatively assess the muscle fatigue elicited by FES under both isometric and dynamic ankle dorsiflexion functionalities is investigated. The results showed that the US ERC expressed an exponential reduction along with the muscle contraction cycles both in isometric and dynamic conditions. Also, the results of linear regression analysis showed strong linear relationships between the US ERC normalization and the gold standard fatigue indicators, namely, isometric dorsiflexion torque normalization or dynamic dorsiflexion angle normalization. The comparison between the current work and existing studies verified that the US ERC is a comparable fatigue indicator to axial tissue strain imaging during the isometric fatigue progression, but with a realistic computation time for real-time implementation. The findings in the current disclosure indicate that the US echogenicity is a promising non-invasive and computationally efficient measure for assessing FES-469 induced muscle fatigue, and potentially, it can be integrated into an advanced FES controller design that considers muscle fatigue in real-time.

Ultrasound-based state assessment of the human muscle during rehabilitation and its integration into a hybrid exoskeleton comprising an functional electrical stimulation (FES) system and a powered orthosis are emerging research areas. This disclosure presents results from the first experimental demonstration of a hybrid knee exoskeleton that uses ultrasound-derived muscle state feedback to coordinate electrical motors and FES. A significant contribution of this disclosure is to integrate a real-time ultrasound image acquisition and processing framework into a recently derived switching-based feedback control of the hybrid knee exoskeleton. As a result, the contractility response of the quadriceps muscle to the FES input can be monitored in vivo in real-time and estimate FES-induced muscle fatigue changes in the muscle. The switched controller's decision-making process can then use the estimated muscle fatigue to compensate or replace the FES-stimulated muscle power with an electrical motor, thus avoiding extensive stimulation of the fatigued muscle. The experimental results suggest a potential application in the rehabilitation of neurological disorders like spinal cord injuries and stroke. Therefore, a combined FES system and a powered exoskeleton is a promising rehabilitation system for individuals with mobility disorders. However, the design and control of a hybrid exoskeleton being a new and emerging research area, numerous challenges in their design and control hinder their clinical implementation.

First, the hybrid exoskeleton must compensate for the declining muscle force due to that rapid onset of FES induced muscle fatigue. The muscle fatigue results from nonphysiological recruitment of muscle motor units, i.e., recruitment is asynchronous and spatially fixed [24]. The fatigued muscle cannot maintain the same muscle power output to actuate the limb joints. Thus, the muscle output cannot maintain desired limb tracking, constraining functional tasks to short periods. Therefore, a specifically designed control strategy must maintain a long operation given the decreasing contribution of FES-recruited muscle power. The hybrid exoskeleton control scheme may use cooperation or a switched strategy to allocate control inputs among external actuators and FES. Further, it should be capable of completely replacing the FES-elicited muscle power with the powered orthosis when the muscle potentially experiences an acute fatigue condition while guaranteeing the system stability. Recent control algorithms for a hybrid exoskeleton facilitate cooperative use of FES and the exoskeleton [11]-[14]. However, a control approach that automates exoskeleton assistance during acute FES-caused muscle failure due to the fatigue and turns-on the FES use when the muscle recovers from the fatigue is lacking. Our recent work proposed a generic theoretical framework [25] for FES-elicited muscles in closed-loop with a wearable robotic system that considers the FES-evoked muscle's fatigue and recovery cycle. The designed switch criteria coordinate FES-elicited muscle power and external actuators while ensuring the hybrid exoskeleton's stability despite nonlinearity, uncertainty, and electromechanical delay (EMD) in the musculoskeletal system. Another challenge is that the lack of sensors to measure muscle fatigue during FES limits effective control of the hybrid exoskeleton. Advanced switched control techniques for hybrid exoskeleton monitor different switch criteria [25] among multiple actuators to ensure system stability and control performance. The switching criteria need measures or estimates of the system state that include the joint angle, joint velocity, and FES-induced changes in muscle condition. Predictive mathematical models [26]-[30] have been used to estimate changes in muscle condition. Compared to those model-only approaches, introducing real-time direct measurements can better assist controller's decision making because the direct measurements provide feedback of the most updated muscle condition, which can then mitigate the estimate errors (due to signal processing noise and modeling uncertainties) accumulated over time. However, the direct and real-time measurement of the muscle condition due to the induced fatigue is infeasible with the typically used sensors in robotic devices (e.g., encoder, strain gauge, inertia measurement units, etc.). Embodiments of the present disclosure address this challenge and provide a new sensing modality to characterize and monitor FES induced muscle contractility changes in vivo.

Ultrasound has been an essential and valuable tool in clinical diagnosis, rehabilitation, and research investigation of human skeletal muscle [31]-[39]. Researchers have recently started developing ultrasound image processing algorithms that enable real-time ultrasound imaging into robotics and prosthetic devices for human augmentation and rehabilitation. Castellini et al. [40] and Gonzalez et al. [41]proposed an ultrasound-based human-machine interface that predicts finger positions and forces from processed ultrasound images. Sikdar et al. [42] developed a wearable ultrasonic system that can classify and predict dexterous individual finger movements.

In some examples [43], [44], ultrasound speckle tracking algorithm [45] is used for tissue motion estimation. The estimated muscle displacement was then used to compute the strain tensor to capture the quadriceps muscle contractility change that was hypothesized as an effect of FES-induced fatigue. The approach was validated on several human participants and demonstrated that the ultrasound-based technique can estimate FES-induced muscle fatigue. Compared to other sensor modalities such as dynamometers, surface electromyography (sEMG), and mechanomyogram (MMG), ultrasound imaging provides both anatomical and functional information, and thus a potential sensing solution for effective hybrid exoskeleton control. Ultrasound imaging is relatively low cost and facilitates a real-time setup, compared to other clinical imaging modalities like magnetic resonance imaging (MRI). In addition, recent advancements in portable ultrasound devices [46]-[48] promise its integration in a compact wearable robotic system. However, to enable ultrasound-based feedback control, the capability of real-time data acquisition is critical because the controller relies on the acquired and most updated information to make control decisions. The real-time characteristic of ultrasound imaging noted in the literature mainly refers to the image acquisition and reconstruction without further image processing for tissue motion estimation. However, the tissue motion estimation is vital to derive muscle contractility-related changes for fatigue estimation. Implementation of this process is a non-trivial problem. It entails accelerating the computation of a tremendous amount of image data to perform the ultrasound speckle tracking algorithm, the primary computation-consuming part. Nevertheless, a graphic processor unit (GPU) offers a potential resource to accelerate the computation. Primarily, the core structure of the speckle tracking algorithm is a kernel based similarity matching, which allows simultaneous parallel computation at different independent local image coordinates. As a result, conceptually, the processing time is unlikely to increase when the data size grows apparently. Several works in the literature [49], [50] have implemented this idea in different GPU-based platforms. In our current disclosure, considering the requirement of up-sampling the images to capture small local displacements, the available memory size of the current generation of GPUs is another limitation. Therefore, a trade-off between the total computation time and the image quality is used to overcome this challenge. The algorithm was implemented in a semi-parallel structure, dividing every single image into several pieces of sub-image and loading them on the GPU consecutively. The parallel computation was then performed on each loaded sub-images, and the processed results were assembled at the end.

After achieving the real-time ultrasound speckle tracking algorithm, the imaging processing procedure can be deployed in feedback control of a hybrid exoskeleton to estimate muscle's fatigue state and assist the controller's decision making. As a result, a 1-degree-of-freedom (1-DOF) hybrid knee exoskeleton is modeled and designed that collaboratively uses an electrical motor at the knee joint and applies FES to the quadriceps-hamstring muscle group. A newly derived switched control method is then implemented. The control objective uses different control modes to track desired knee joint movements. The first mode collaboratively uses FES-activated muscle power and an electrical motor, while the second mode only uses all electrical motor power. The two modes are switched and are active in turns, subject to switch criteria determined by the stability constraints and the muscle fatigue state. The control design is robust to modeling uncertainties and compensates for the EMD. The hybrid knee exoskeleton is finally integrated with the developed real-time ultrasound image acquisition and processing platform. The presented results for the first time experimentally demonstrate real-time measurement of the muscle state due to the induced muscle fatigue via ultrasound derived strain measures and its integration into feedback for the hybrid exoskeleton controller's decision-making.

Diagnostic Imaging Procedure

To imitate the methodology of ultrasound imaging-based muscle fatigue assessment (as in [43], [44]) in the real-time control system, a "diagnosis imaging" procedure is designed. Specifically, as illustrated by the sketch at the top of FIG. 2, when the desired motion trajectory, qd(t) (chosen as a sinusoidal curve in the current experiment), periodically reaches its minimum, two consecutive short pulses as trigger signals are generated accurately at that time instance. The first pulse is used to interrupt the controller-calculated error-modulated FES input and replace it with a constant 1-second "diagnostic" FES input. The second pulse is delayed for 100_300 ms after the first pulse. It is used to trigger a short time window when the ultrasound image acquisition and processing are active to assess the muscle's response to the "diagnostic" FES input. The reason for locating the trigger signals at the valley of a sinusoidal is that, around that time, the actual knee movement under the feedback control also reaches the valley, i.e., velocity is zero and the quadriceps muscle is at a relaxed status. Then the applied "diagnosis-imaging" procedure is similar to the isometric knee extension experiment, as reported in [43], [44]. A triggering delay in the second pulse for ultrasound imaging considers the EMD in muscle's response after the diagnostic FES. The hardware and computation resources can be efficiently located and focus in a time window when a dominant muscle contraction occurs. Due to the current limitation of computation speed in ultrasound image processing, the designed "diagnosis-imaging" procedure is repeated, and ultrasound image measurements are available every 20 seconds. When ultrasound image measurements are obtained, the raw radio frequency (RF) data is passed to the GPU-based image processing platform. The images are reconstructed by a delay-and-sum (DAS) beamformer and the ultrasound speckle tracking is performed to calculate muscle's displacement field. Strain images are then calculated based on the gradient of the displacement field. Due to the force-strain correlation discussed in [43], [44], the average of the strain image is calculated and normalized to approximate the fatigue state, μ^, at the current time instant. This value is then passed to the predictive fatigue model, (7), and used as the new initial condition of the fatigue model during the time period when ultrasound image measurements are not available. Then the estimate of the fatigue state during this period (between two consecutive available ultrasound image measurements) is calculated by the re-initialized fatigue model. Finally, the fatigue estimate is passed to the feedback controller to determine the switches between control mode uml and umll.

Gpu-Based Ultrasound Imaging Processing

The original speckle tracking algorithm used for tissue motion estimation in [43], [44] is based on exhaustively searching the displacement vector candidate (from the reference frame to the moving frame) that makes the normalized cross-correlation coefficient the maximum. It has a good performance to estimate tissue motion to the level of about 0:01 mm. However, it is difficult to satisfy real-time capabilities required for closed loop control. This is due to that the computation cost increases quadratically with the size of the kernel and search window in the following 2D normalized cross-correlation computation, $$\gamma(x, y) = \frac{\sum K_{x,y}\left(f_m(a, b) - \overline{f}_m\right)\left(f_n(a+u, b+v) - \overline{f}_{n,u,v}\right)}{\sqrt{\sum K_{x,y}\left(f_m(a, b) - \overline{f}_m\right)^2\left(f_n(a+u, b+v) - \overline{f}_{n,u,v}\right)^2}} \quad (64)$$

where γ is the normalized correlation coefficient at location, (x,y), $f_m$ and $f_n$ refer to magnitude of the ultrasound image signal from frame number m and n, respectively. (a,b) ∈ $K_{x,y}$. $K_{x,y}$ is the rectangular kernel centered at position (x,y). Inside the kernel, signal magnitude at all the locations are used to compute the similarity measure that is the normalized cross-correlation, γ. For computing γ, f¯ m, f¯ n, u, v are mean values of $f_m$(a,b) and $f_n$(a+u,b+v), respectively. u(x,y) and v(x,y) are the offsets that form the displacement vector, (u,v) at location (x,y).

Figure 32:
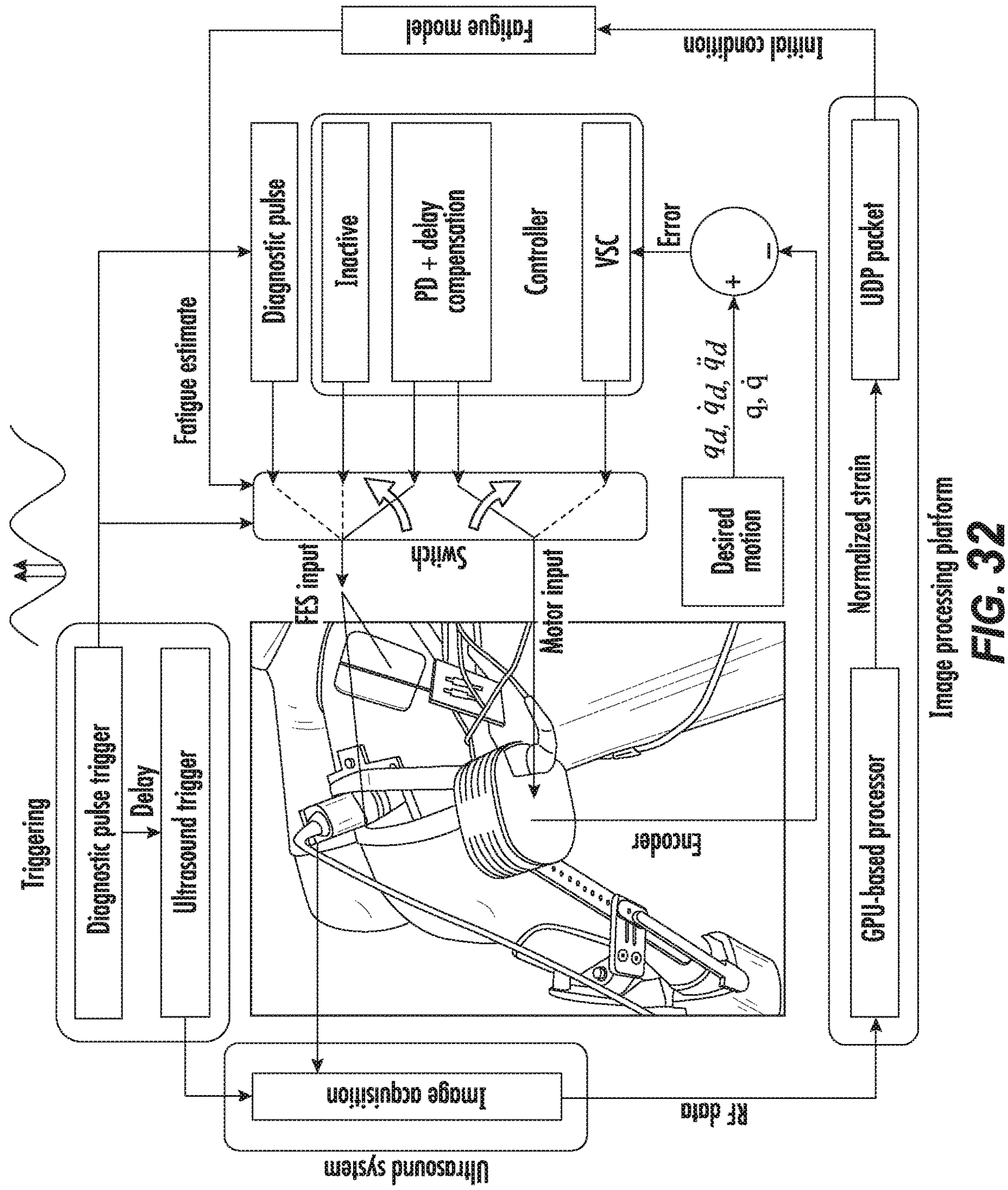
FIG. 32 is a schematic diagram according to implementations described herein.
Figure 33:
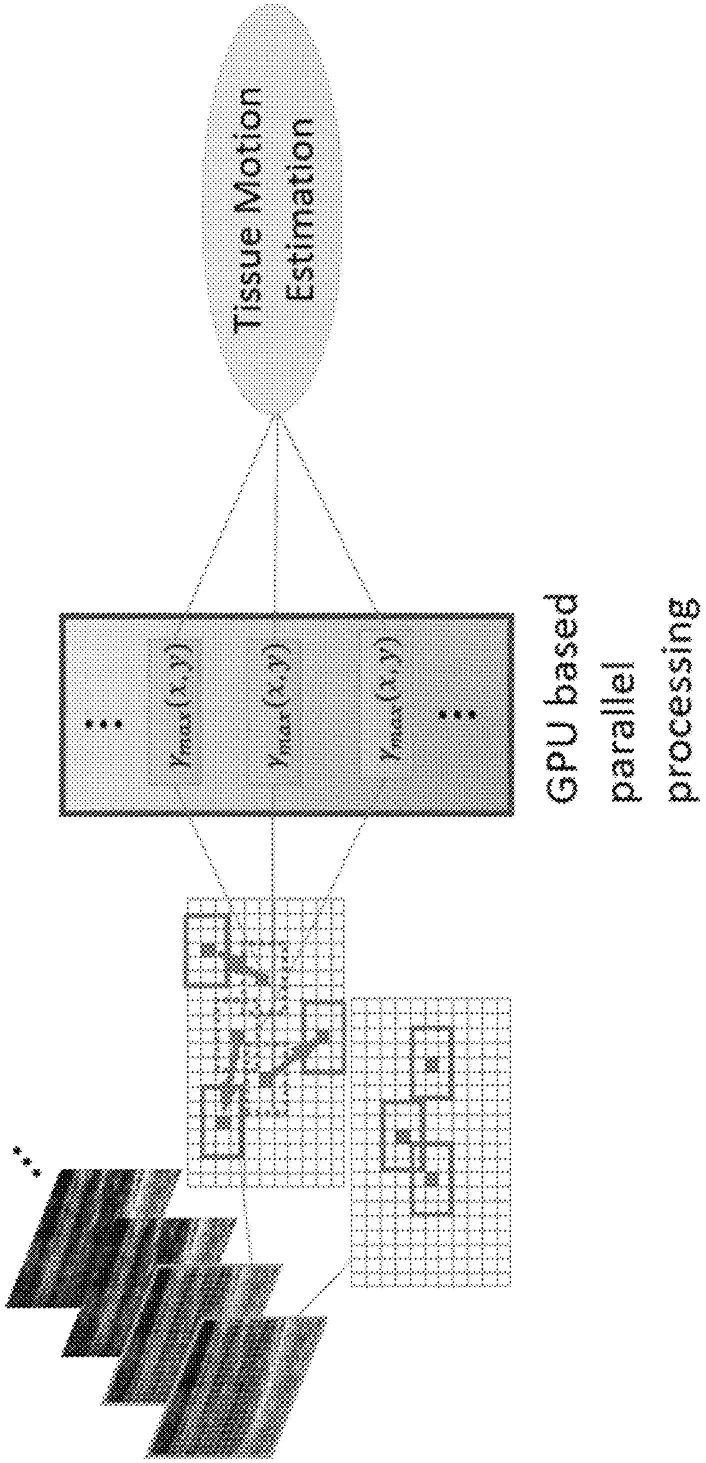
FIG. 33 is a schematic diagram according to implementations described herein.

According to the form of γ(x,y) that can be computed independently at different locations, (x,y), the speckle tracking algorithm can be implemented using a GPU architecture that enables parallel computing to accelerate the overall computation to achieve real-time strain measurements. By further tuning the speckle tracking parameters, such as the size of the region of interest and kernel, to balance the image processing quality and the real-time requirement, the processing time to compute the strain between two consecutive images was eventually reduced to <1 second when implemented on the GPU. The workflow for the parallel computing implementation is shown in FIG. 32. Referring now to FIG. 32, a schematic diagram depicting an example Workflow for parallel computation of the 2-D cross-correlation used for real-time implementation. It is noted that the cross-correlation computation at each point in the region of interest in (8) is independent. The ultrasound images are loaded onto the GPU and the cross-correlation, (x,y), is computed simultaneously at every point in the region of interest.

Seven trials were performed to test the integration of real-time ultrasound imaging into the closed-loop control system of the 1-DOF hybrid knee exoskeleton. FIG. 49 summarizes the experiment results while FIG. 34 is the graphic presentation of trial 4.

Figure 34:
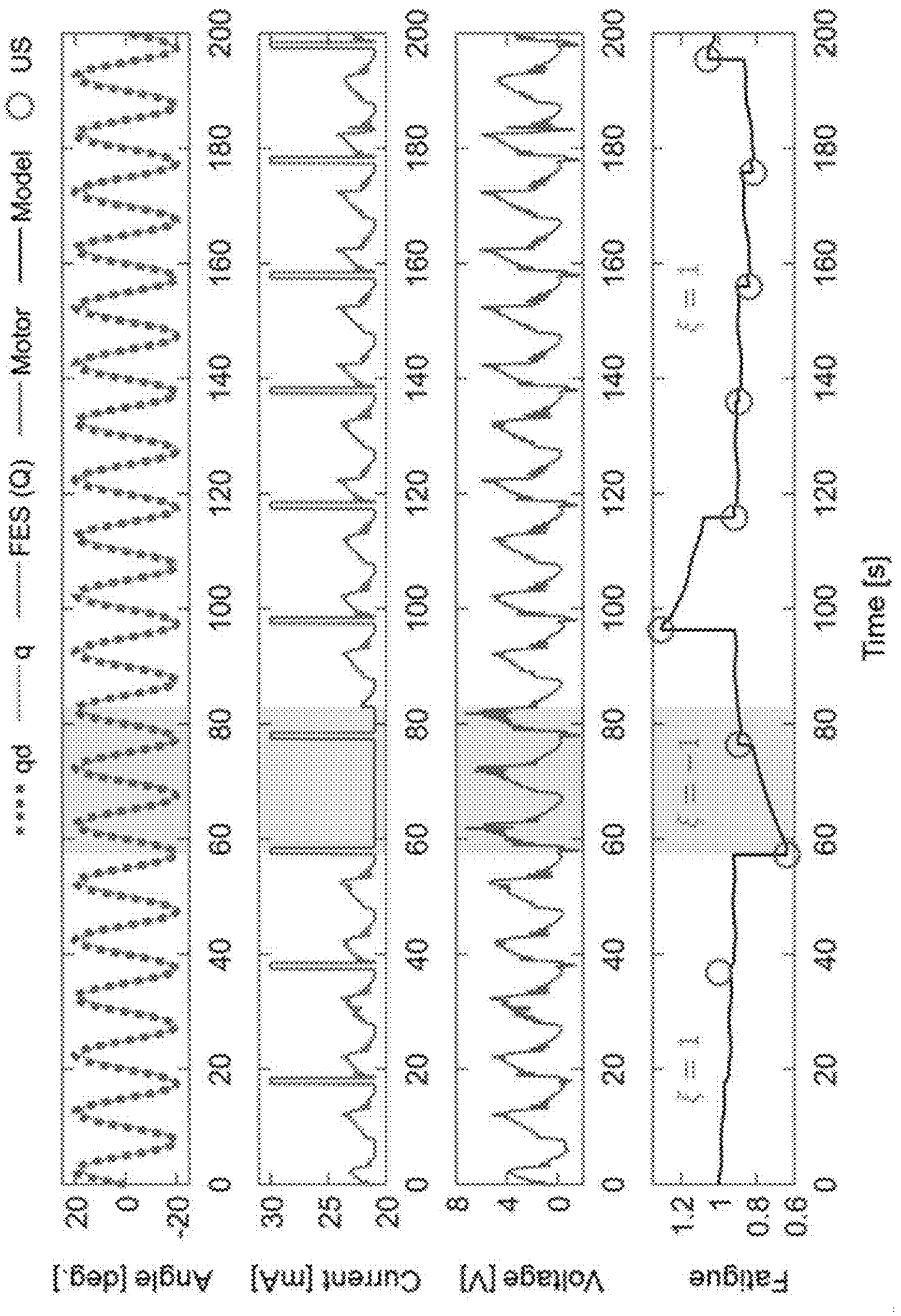
FIG. 34 is a schematic diagram according to implementations described herein.

The RMSE is calculated between the encoder registered knee joint angle (q, solid orange curve in the first row of FIG. 34) and the desired knee joint angle (qd, dotted blue curve in the first row of FIG. 34). The results show a good control performance (error less than 2°) under the designed closed loop control system despite the occurrence of the fatigue-based switches between different control modes, as well as the "diagnostic" FES input (that acts as a disturbance from the controller's point of view). The switching behavior is also successfully achieved according to the designed fatigue-based switch criteria when the assessing FES-induced muscle fatigue is based on real-time ultrasound imaging. The shadowed region in FIG. 34 denotes the switch to the VSC controller (motor only) when the estimated fatigue state is below the chosen lower threshold (0:8). The second row of FIG. 34 plots the time-variant value of the FES input to the quadriceps muscle by the solid red curve. The baseline of this curve (21 mA) reflects the threshold level of the participant's muscle, above which the FES input can generate a noticeable muscle response (i.e., a noticeable force generation during preliminary isometric muscle contraction experiments). The periodically occurring squared pulses with a high peak (30 mA) reflect the "diagnostic" FES input. In contrast, the flat part (approximately between 60 s and 80 s) reflects the deactivation of FES when the muscle is considered as "fatigued" (below the lower threshold, 0:8) and the alternative control mode (VSC, motor only) is used. The FES input to the hamstring muscle is omitted because its value is minimal (in the order of $10^{-1}$ mA above the baseline). In addition, as is observed from the last row of FIG. 4, the jumps on the model-based fatigue curve (solid black curve) reflect the re-initialization of the predictive model when a most updated measurement from real-time ultrasound imaging (purple circle) is acquired. The first ultrasound measurement is used as the baseline for strain normalization and is not used to re-initialize the model. A small jump on the fatigue curve indicates a relatively good agreement between the ultrasound assessed and the model-predicted fatigue state. In contrast, a significant jump shows a considerable discrepancy between the ultrasound measurement and the model prediction at the specific time instance. However, at the current stage of our disclosure, it is difficult to determine which one is closer to the absolute ground truth because multiple uncertainties exist in both processes for identifying the fatigue model and the strain-force correlation. In fact, for the predictive fatigue model, due to its dependency on accurate model parameters and the initial condition, the bias of fatigue estimation is expected to accumulate over time. Thus, the model needs re-initialization by the real-time ultrasound measurements. However, the obtained ultrasound measurements themselves have a noisy aspect and can sometimes have inconsistent oscillations between samples on the time horizon. This is because the ultrasound measurements are separate independent data samples and do not constrain the temporal trend. This potentially brings significant variance to and affects the fatigue estimation when these samples are repeatedly used to reinitialize the model, especially when the sampling rate of the ultrasound assessment is low (every 20 s) due to the limitation of computation speed. One potential solution is to optimize the image processing platform further to increase the computation speed to obtain ultrasound measurements more frequently. In this way, when more consecutive data samples are available during a specific time window, filtering techniques can be applied to mitigate the noisy aspect of the signals. An alternative solution is to combine the predictive fatigue model and intermittently available ultrasound measurements in an observer-like structure. In this way, due to the ultrasound measurements, the predictive fatigue model no longer relies on an accurately known initial condition, while the temporal theoretical trend provided by the model can be used as a temporal constraint to regularize the ultrasound measurements. For the first time, this disclosure designs and implements a closed-loop control system of a one-DOF hybrid knee exoskeleton that integrates real-time ultrasound imaging for FES induced muscle fatigue assessment. The experiment results show the feasibility of applying ultrasound imaging for tissue strain estimation as an indicator of muscle fatigue and subsequently facilitating the control system's switch behavior. The results show that FES and powered assistance can be switched between different assistive modes when the muscle undergoes a fatigue and recovery cycle while achieving a good control performance.

This disclosure shows that ultrasound imaging as a sensing modality in assistive devices helps feedback controllers in decision-making and potentially enables unrestrained, robust fatigue-resistant limb movements for functional tasks.

Improving the prediction ability of a human-machine interface (HMI) is critical to accomplish a bio-inspired or model-based control strategy for rehabilitation interventions, which are of increased interest to assist limb function post neurological injuries. A fundamental role of the HMI is to accurately predict human intent by mapping signals from a mechanical sensor or surface electromyography (sEMG) sensor. These sensors are limited to measuring the resulting limb force or movement or the neural signal evoking the force. As the intermediate mapping in the HMI also depends on muscle contractility, a motivation exists to include architectural features of the muscle as surrogates of dynamic muscle movement, thus further improving the HMI's prediction accuracy.

The purpose of this disclosure is to investigate a non-invasive sEMG and ultrasound (US) imaging-driven Hill-type neuromuscular model (HNM) for net ankle joint plantarflexion moment prediction. The fusion of signals from sEMG and US imaging results in a more accurate net plantarflexion moment prediction than sole sEMG or US imaging.

Methods

Ten young non-disabled participants walked on a treadmill at speeds of 0.50, 0.75, 1.00, 1.25, and 1.50 m/s. The proposed HNM consists of two muscle-tendon units. The muscle activation for each unit was calculated as a weighted summation of the normalized sEMG signal and normalized muscle thickness signal from US imaging. The HNM calibration was performed under both single-speed mode and inter-speed mode, and then the calibrated HNM was validated across all walking speeds.

Results

On average, the normalized moment prediction root mean square error was reduced by 14.58% ($p=0.012$) and 36.79% ($p<0.001$) with the proposed HNM when compared to sEMG-driven and US imaging-driven HNMs, respectively. Also, the calibrated models with data from the inter-speed mode were more robust than those from single-speed modes for the moment prediction.

The proposed sEMG-US imaging-driven HNM can significantly improve the net plantarflexion moment prediction accuracy across multiple walking speeds. The findings imply that the proposed HNM can be potentially used in bio-inspired control strategies for rehabilitative devices due to its superior prediction. Locomotion mobility accounts for a dominant part of human activities of daily living, like moving around the home and community, going to work or school, doing errands, visiting friends, etc. The human lower extremity plays an essential role in achieving locomotion mobility. The human ankle plantarflexors generate a large burst of "push-off" mechanical power during the late stance phase of walking, enabling forward and upward acceleration of the body's center of mass. Due to neurological disorders or injuries like spinal cord injury, stroke, and multiple sclerosis, the weakened function or dysfunction of plantarflexors is likely to cause a dramatic decrease in the "push-off" power. Consequently, these mobility disorders impair walking function and cause poor energy economy [1], as well as disrupt both physical and emotional well-being [2].

Modern neurorehabilitation devices, such as powered ankle exoskeletons [3-5], soft exosuits [6, 7], and functional electrical stimulation [8-12], may use assist-as-needed control to actively engage and maximize recovery of users with mobility impairments [13, 14]. In turn, the efficacy of the control strategy depends on the accurate determination of continuous human volitional movement intent (net joint moment). Mechanical sensors, like force or torque sensors, installed on a rigid and bulky frame, have been often used to measure the human intent for joints without direct interaction to the ground, but limit the system's wearability. Also, inaccuracies may creep in easily due to the inevitable misalignment between the bionic joint center and human joint center, which may introduce undesired interaction force [15, 16]. Usually, it is challenging to directly measure the net ankle joint moment during walking overground with conventional force or torque sensors setup. The standard way to measure the net ankle joint moment uses a motion capture system, ground reaction force (GRF), and inverse dynamics (ID) calculations. However, there are two shortcomings of the standard approach. First, the setup is constrained to a lab environment, and not applicable for field testing. Second, the results from ID do not reveal how skeletal muscles perform during walking from a neuromuscular perspective. Therefore, a forward dynamics approach based on a neuromuscular model would be very instrumental when a motion capture system and GRF data are unavailable.

Surface electromyography (sEMG) measures electrical potentials during asynchronous muscle neurons firings, and its amplitude and frequency positively relate to muscle activation levels. Therefore, sEMG-derived signals can be used in a Hill-type neuromuscular model (HNM) or to train a machine learning approach (model-free) to predict volitional joint moment [17, 18] and angular position [19-21]. However, sEMG signals suffer from interference or cross-talking from the adjacent muscles, and an inability of measuring activations of deep-layer muscles [22, 23]. Alternatively, two-dimensional brightness mode (B-mode) ultrasound (US) imaging allows one to see the musculature of the targeted muscle in vivo. Due to its ability to directly visualize superficial and deep-layer muscles, US imaging may work as an alternative methodology to predict joint motion or motion intent. Potentially, US imaging overcomes the shortcomings of the sEMG measurements. Most frequently used architectural features from US images include pennation angle (PA) [24, 25], fascicle length (FL) [26, 27], muscle thickness (MT) [28, 29], and cross-sectional area [30]. These features have been correlated with the joint kinetics and kinematics during isometric or isokinetic joint motion by using HNM-based or model-free approaches [25, 31-33]. Motivation also exists to use a dual-modal approach that combines the measurement from sEMG and US imaging. Potentially sEMG signals and US imaging provide complementary information, and the combination between them may (1) mitigate any cross-talking effect from neighboring sEMG signals and (2) lower US imaging-derived features' drift due to the accumulated errors from cyclic joint movement. Our recent studies have shown the advantages of using the dual-modal approach over uni-modal bio-signals (sEMG or US imaging) for ankle joint moment/motion prediction under isometric/dynamic dorsiflexion studies [21, 25, 27] and isometric plantarflexion disclosure [34, 35]. Similarly, Dick et al. used both sEMG and US imaging to predict plantarflexion force during dynamic cycling tasks [32]. However, the use of the dual-modal bio-signals during more complex functional tasks, like walking across different speeds remains unexplored. In this disclosure, a dual-modal approach that takes both processed sEMG and MT from US imaging as inputs to a modified HNM, named sEMG-US imaging-driven HNM, to predict net ankle joint plantarflexion moment during the walking stance phase across multiple speeds is investigated. The proposed HNM achieves a better net plantarflexion moment prediction accuracy than sEMG-driven and US imaging-driven HNMs, and the net plantarflexion moment prediction performance is more robust if data collected from multiple speeds are included in HNMs' calibration procedure.

In previous US imaging studies, visualized architectural features, such as PA and FL, require high-resolution US imaging, which can be significantly affected by a US transducer placement site on the muscle. To mitigate the requirement of high-resolution US imaging, US imaging-derived signals such as echogenicity [27, 36, 37], tissue displacement [38], and MT [29], are more preferable to correlate with muscle or joint mechanical functions. Because ankle plantarflexors: lateral and medial gastrocnemius and soleus muscles (LGS, MGS, and SOL) are not accessible in the same US image plane, this disclosure chose to focus on LGS and SOL, which are in the same plane, and tracked their MT change during the walking experiments across multiple speeds. Therefore, the contributions of this disclosure are: (1) the use of US imaging-derived MT changes and sEMG-derived changes of LGS and SOL muscles as surrogate variables of muscle activations during walking, (2) development of a modified HNM that uses both sEMG and US imaging as inputs for single-speed modes and an inter-speed mode, and (3) evaluation of the sEMG-US imaging-driven HNM's robustness across multiple walking speeds.

Hill-Type Neuromuscular Model of Ankle Joint

Below, a modified sEMG-US imaging-driven HNM to directly build a relationship between the joint net PF moment and sEMG-US imaging-derived surrogate signals of both LGS and SOL muscles is provided. There are three sub-models involved in the HNM: (a) sEMG-US imaging-derived weighted muscle activation model, (b) muscle-tendon unit geometry model, and (c) muscle contraction dynamic model.

Weighted Muscle Activation Model

The neural activation at tk time instant Ni(tk),i=1,2, k=1, 2, 3, . . . , for SOL and LGS muscles, respectively, considers the electromechanical delay (EMD), τ, between the onset of an sEMG signal and a muscle contraction and utilizes a second-order recursive filter and is defined as [39]

$$N_i(t_k) = \alpha_i u_i(t_k - \tau) - \beta_{1i} N_i(t_{k-1}) - \beta_{2i} N_i(t_{k-2}) \tag{65}$$

where EMD, τ, is usually between 30 ms and 120 ms. Ui($t_k$) represents the sEMG's linear envelope normalized to the peak value of the specific task (with a constant peak value across all walking speeds on each subject in this disclosure). The sEMG's linear envelope was derived after raw sEMG signals' band-pass filtering, full-wave rectification, and low-pass filtering. A i, β 1i, and β 2i are coefficients that define the recursive filter's dynamics of each muscle [39], and the following set of constrains is employed to reach a positive stable solution, i.e.

$$\beta_{1i} = \gamma_{1i} + \gamma_{2i},\ \beta_{2i} = \gamma_{1i} \cdot \gamma_{2i},\ \alpha_i - \beta_{1i} - \beta_{2i} = 1 \tag{66}$$

where |γ 1i|i<1 and |γ 2i|<1. A nonlinear relationship between neural activation Ni(tk) and corresponding muscle activation a1i(tk) is given as [39]

$$\alpha_{1i} = \frac{e^{A_i N_i} - 1}{e^{A_i} - 1} \tag{67}$$

$$\alpha_{1i} = \frac{e^{A_i N_i} - 1}{e^{A_i} - 1}$$

where $A_i$ represents the nonlinear shape factor for each muscle, which is allowed to vary between −3 and 0, with $A_i$=−3 being a nonlinear and $A_i$=0 being a linear relationship. According to the reported results in [40-43], the MT change was found to correlate with the muscle contraction level or muscle activation through a linear function or piece-wise linear function. Therefore, the second part of the LGS or SOL muscle activation is calculated from the US imaging-derived MT change. The MT values of LGS and SOL muscles are denoted as $MT_i(t_k)$. According to the preliminary results in [44], there is a positive relationship between MT change and the targeted muscle contraction level during the walking stance phase. After taking normalization of the MT with respect to the lower bound (at rest state) and upper bound (peak value of the specific task) on each participant, the US imaging-derived muscle activation, α2i(tk), is proposed as $$a_{2i} = \frac{MT_i - MT_{imin}}{MT_{imax} - MT_{imin}} \tag{68}$$

where $Mt_{imax}$, and $Mt_{imin}$ represent the constant subjective MT values when the LGS and SOL muscles are at the walking task-specific maximum voluntary contraction and complete rest condition, respectively. For each individual, $Mt_{imax}$ and $M_{timin}$ are set as consistent values across different walking speeds. This normalization guarantees that the US imaging-derived muscle activations vary between 0 and 1. By introducing an allocation gain between the sEMG- and US imaging-derived muscle activations, the synthesized/weighted muscle activation levels for LGS or SOL muscle, $a_i(t_k)$, can be represented as $$a_i = \delta_i a_{1i} + (1 - \delta_i) a_{2i} \tag{69}$$

where $\delta_i \in [0,1]$ represents the muscle activation allocation gain for LGS (i=1) and SOL (i=2) muscles.

Muscle-Tendon Unit Geometry Model

Figure 35:
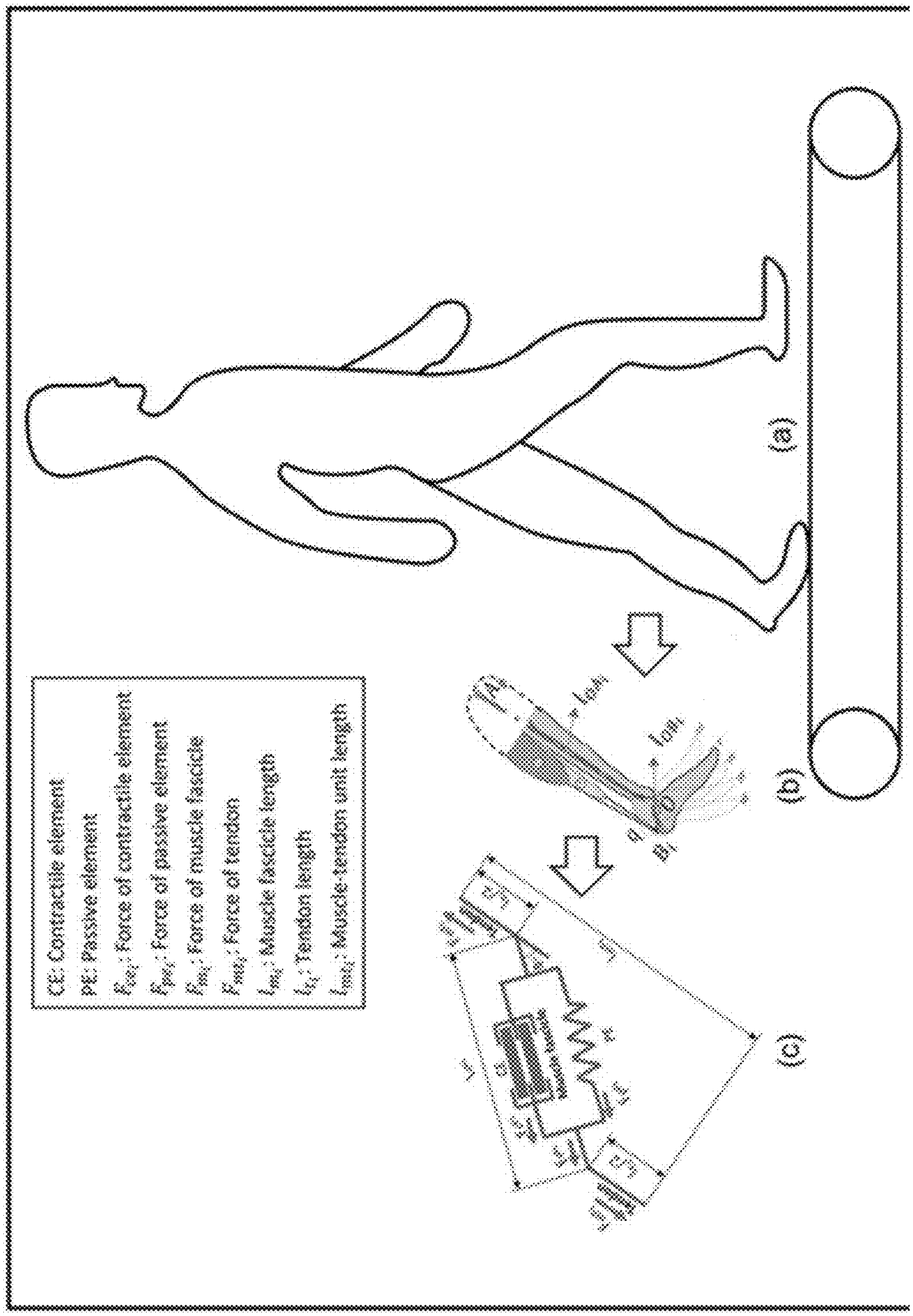
FIG. 35A-C are schematic diagrams according to implementations described herein.

As presented in FIG. 35(*b*), consider the ankle joint rotation center in the sagittal plane as O, the proximal and distal osteotendinous junction points of each muscle-tendon unit (MTU) near the knee joint and heel as Ai and Bi, and the angle between OAi and OBi as q(tk), then each MTU length, Imti(tk), is represented as the distance between Ai and Bi, and is calculated as $$l_{mt_i} = \sqrt{l_{OA_i}^2 + l_{OB_i}^2 - 2 l_{OA_i} l_{OB_i} \cos(q)} \tag{70}$$

where $l_{OAi}$ and $l_{OBi}$ represent the distance of $O_{Ai}$ and $O_{Bi}$ obtained from OpenSim (National Institutes of Health for Biomedical Computation, Stanford, USA) [45], respectively. A generic OpenSim model (gait2392) was linearly scaled to each participant in OpenSim version 4.1 [45] per [46]. According to the law of sines, the moment arm of each MTU, $l_{mti}(t_k)$, is calculated as $$r_{mt_i} = \frac{\partial l_{mt_i}(q)}{\partial(q)} = \frac{2 l_{OA_i} l_{OB_i} \sin(q)}{l_{mt_i}} \tag{71}$$

The MTU generates contraction force only when it is stretched, which indicates the current tendon length $l_{ti}(t_k)$ is equal to or longer than the tendon slack length, $$l_{ti}^{sk}.$$

From the perspective of muscle contraction dynamics that is shown in FIG. 35(*c*), the overall MTU length, $l_{mti}(t_k)$, could also be expressed as $$l_{mt_i} = l_{t_i} + l_{m_i}\cos(\phi_i) \tag{72}$$

where $l_{ti}(t_k)$ and $l_{mi}(t_k)$ represent the current tendon length and muscle fascicle length for LGS and SOL muscles, respectively. $\phi_i(t_k)$ represents the pennation angle that changes with instantaneous $l_{mi}(t_k)$. By assuming the individual muscle belly has a relatively small MT change and volume change [47, 48], $\phi_i(t_k)$ can be approximately calculated as $$\phi_i \approx \arcsin\left(\frac{l_{m_i}^0 \sin\phi_i^0}{l_{m_i}}\right) \tag{73}$$

where the term $$\Phi_i^0$$

denotes the constant pennation angle when the muscle is at optimal fascicle length $$l_{mi}^0.$$

The work in [49, 50] has shown that the optimal fascicle length increases as muscle activation decreases. Due to this coupling, the following relationship between the muscle activation and corresponding optimal fascicle length is given as $$l_{m_i}^0 = l_{mo_i}^0(\lambda(1 - a_i) + 1) \tag{74}$$

where $\lambda$ is the rate of change in the optimal fascicle length, and it is selected as 0.15 [39].

$$l_{moi}^0$$

is the optimal fascicle length at the walking task-specific maximum voluntary contraction, and $$l_{mi}^0$$

$(t_k)$ is the optimal fascicle length at time $t_k$ and muscle activation $a_i(t_k)$.

From the preliminary results of plantarflexors' US imaging in [44], it is very challenging to capture the entire fascicle length $l_{mi}(t_k)$ of LGS or SOL muscles by using the current US transducer with a small dimension (width of 38 mm). Therefore, the fascicle length parameters of either LGS or SOL muscles were not measured directly from the US images. Instead, an indirect calculation method was applied as detailed below. According to [51], the nonlinear nominal tendon force-tendon strain relationship is given as $$F_{t_i}(\xi_i) = \begin{cases} 0, & \xi \le 0 \\ 1480.3 F_i^{max} \xi_i^2, & 0 < \xi < 0.0127 \\ (37.5\xi_i - 0.2375) F_i^{max}, & \xi \ge 0.0127 \end{cases} \tag{75}$$

$$\text{Where } \xi_i = \frac{l_{t_i}(t_k) - l_{t_i}^{sk}}{l_{t_i}^{sk}}$$

represents the tendon strain and $$F_i^{max}$$

represents the muscle contraction force at the walking task-specific maximum voluntary contraction. By considering $F_{ti}(\varepsilon_i)=F_{mti}$, where $F_{mti}$ is defined in (13), $l_{ti}$ $(t_k)$ can be numerically computed based on the Runga-Kutta-Fehlberg algorithm. By substituting (6) and (9) to (8), the muscle fascile length the muscle fascicle length $l_{mi}$ $(t_k)$ will be calculated, as well as the muscle fascicle velocity $v_{mi}$ $(t_k)$ by taking the time derivative of $l_{mi}$ $(t_k)$.

Muscle Dynamic Contraction Model

In the sEMG-US imaging-driven HNM, the individual moment component produced by each muscle, $M_i(t_k)$, can be represented as $$M_i = F_{mt_i} r_{mt_i} \tag{76}$$

where $r_{mti}(t_k)$ is defined in the above geometry model and $F_{mti}$ $(t_k)$ denotes the corresponding contraction force generated on each MTU and is represented as $$F_{mt_i} = (F_{ce_i} + F_{pe_i})\cos(\phi_i) \tag{77}$$

where $\phi_i(t_k)$ represents the pennation angle defined above. $F_{cei}$ $(t_k)$ and $F_{pei}$ $(t_k)$ denote the corresponded forces generated by the parallelly located contractile element and the passive element, and can be calculated as $$F_{ce_i} = F_i^{max} f_{l_i}(l_{m_i}) f_{v_i}(v_{m_i}) a_i \quad (78)$$

$$F_{pe_i} = F_i^{max} f_{p_i}(l_{m_i})$$

In (14), $$F_i^{max}$$

of the LGS and SOL muscles will be identified based on optimization algorithm in the HNM calibration procedures. $f_{li}(l_{mi}(t_k))$, $f_{vi}(v_{mi}(t_k))$, and $f_{pi}(l_{mi}(t_k))$ denote the generic muscle contractile forcefascicle length, force-fascicle velocity, and passive elastic force-fascicle velocity curves. These curves were normalized to $$F_i^{max},$$

optimal fascicle length $$l_{mi}^0,$$

and maximum fascicle contraction velocity $$V_{mi}^{max}.$$

Figure 36:
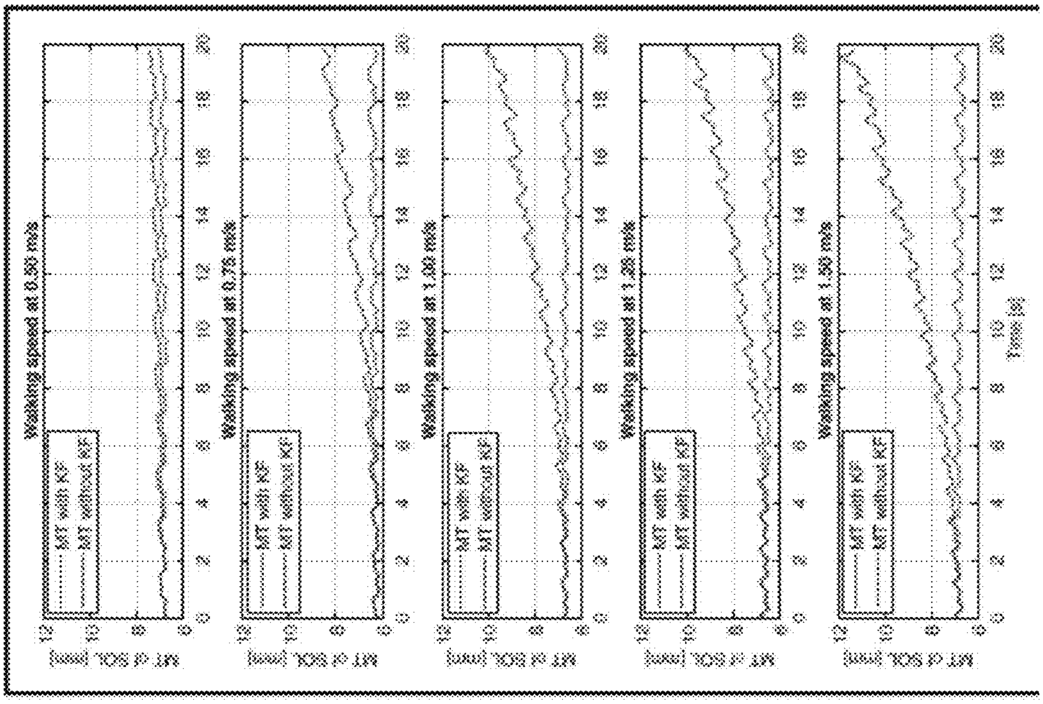
FIG. 36 is a schematic diagram according to implementations described herein.

The treadmill walking speed's effect on human ankle joint kinematics, kinematics, and lower extremities' muscles activities has been extensively investigated and discussed in a recent disclosure [57], but without results related to the architectural change of those muscles. In this disclosure, the time sequences of both LGS and SOL's muscle thickness during the recorded walking duration were extracted by using UltraTrack. Take the SOL muscle of Participant Sub08 as an example, FIG. 36 shows the MT tracking results throughout the 20 s walking duration at each walking speed. The red solid and blue dashed curves represent the MT change of the SOL muscle with and without key-frame correction, respectively. The results demonstrate that the key-frame correction could significantly reduce the time-related drift, which is due to the tracking error accumulation along with the walking duration (exampled US imaging video with the LGS and SOL's MT tracking results at multiple walking speeds can be referred to Additional files 2, 3, 4, 5, 6). The reported results here are consistent with the studies mentioned in [55].

Figure 37:
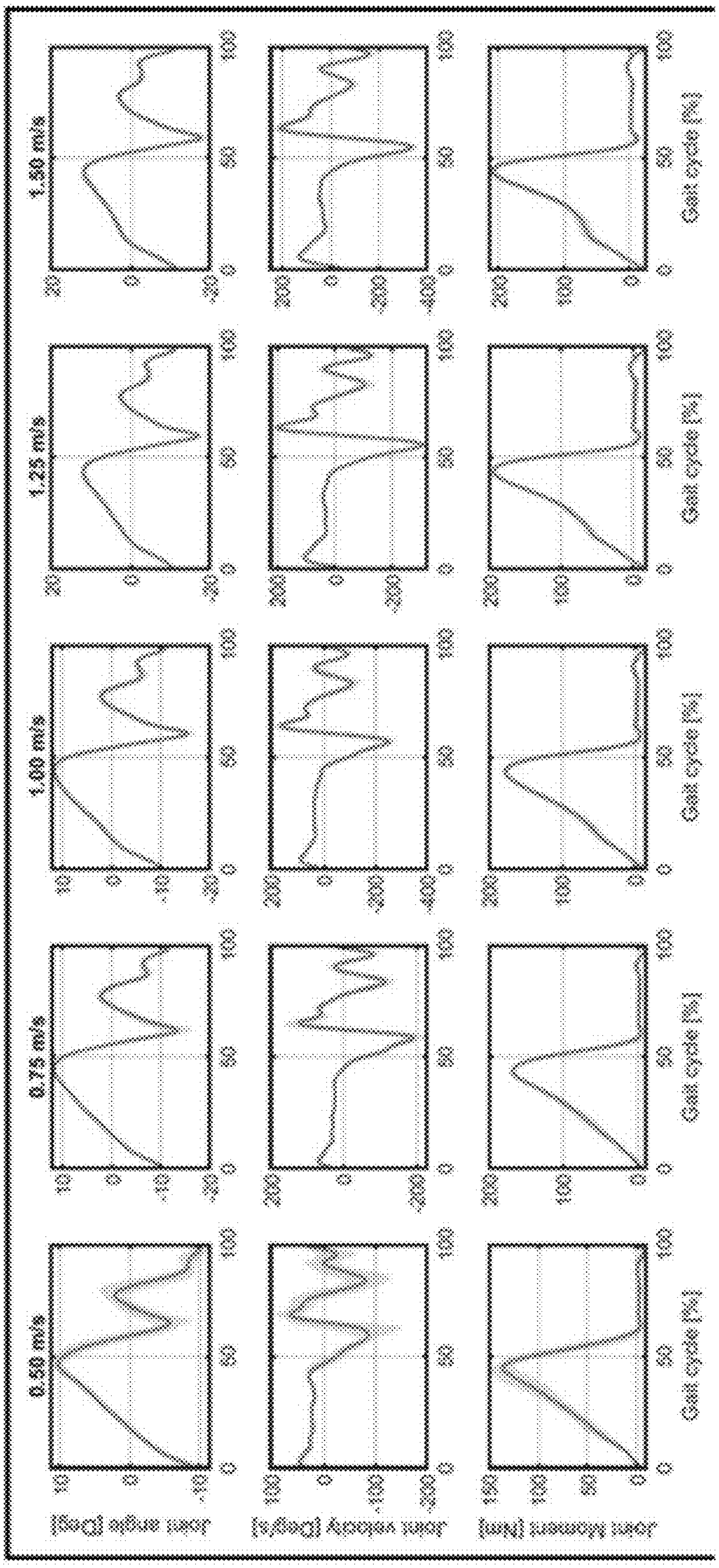
FIG. 37 is a schematic diagram according to implementations described herein.
Figure 38:
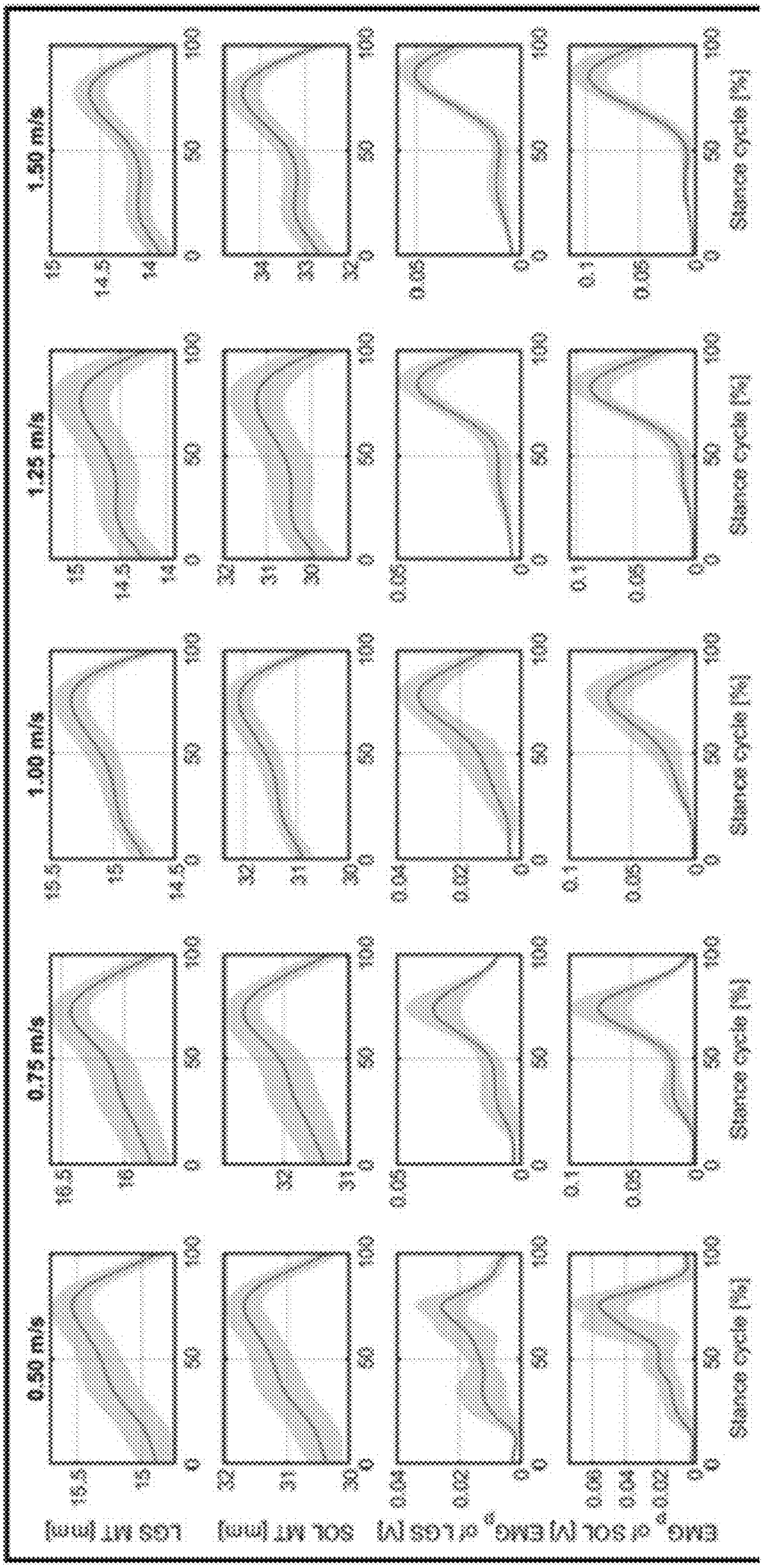
FIG. 38 is a schematic diagram according to implementations described herein.
Figure 39:
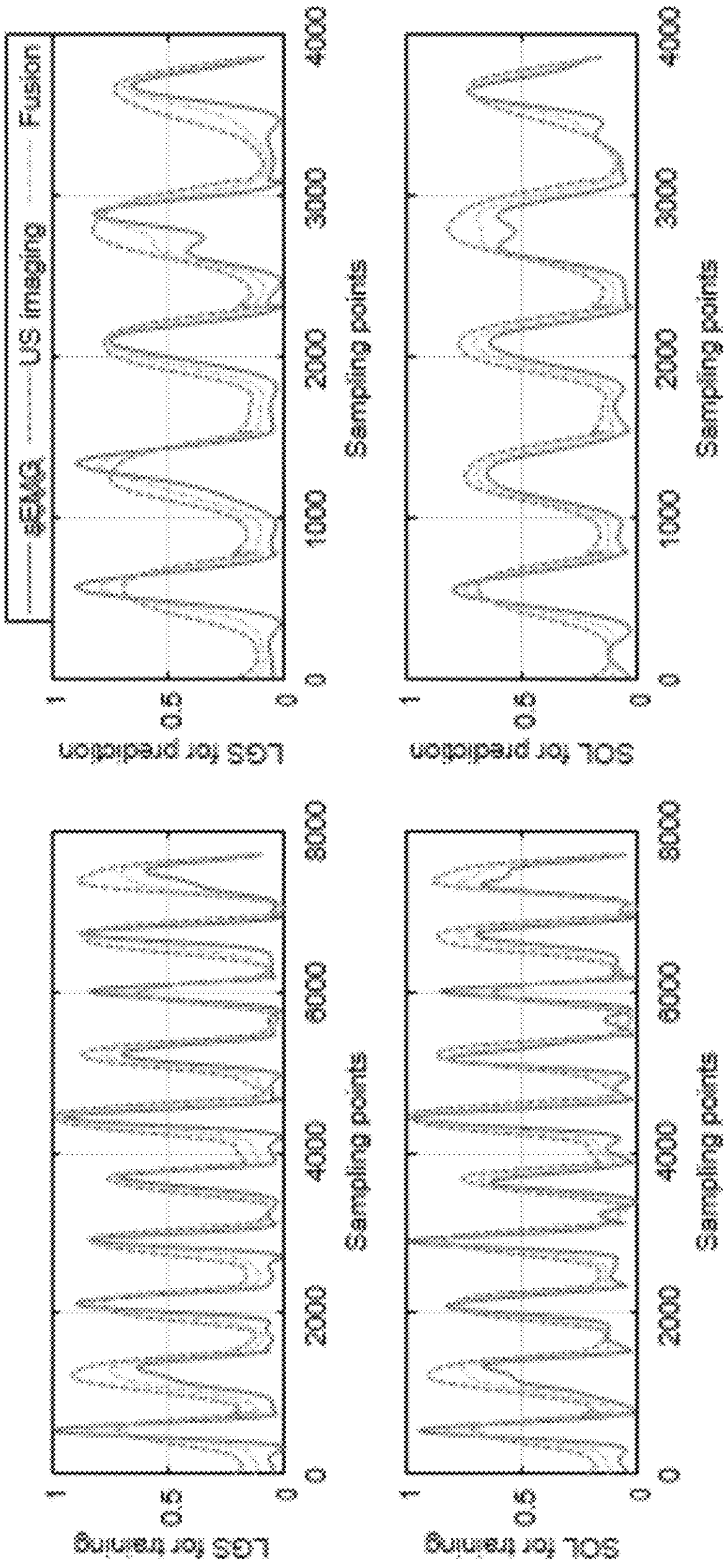
FIG. 39 is a schematic diagram according to implementations described herein.
Figures 40A, 40B, 40C, 40D, 40E:
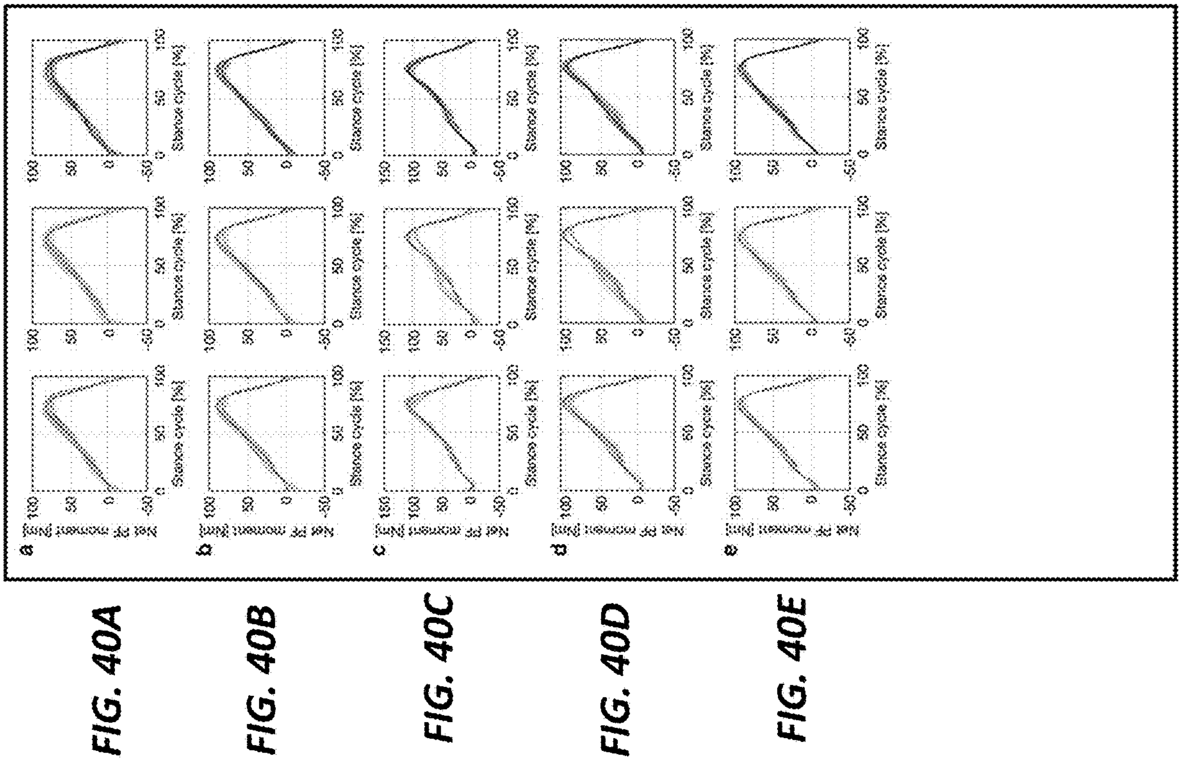
FIG. 40A-E are schematic diagrams according to implementations described herein.

The continuous results of the ankle joint kinematics and kinetics throughout the recorded 20 seconds at each speed were segmented as a percent of gait cycle from 0 to 100% according to the GRF measurements, which are shown in FIG. 37. The solid lines and light shadowed areas report the mean and one standard deviation (SD) values of the right ankle joint angular position, velocity, and net PF moment changes across all gait cycles at each walking speed on Sub01, where 0% and 100% represent the time instants when the heel-strike occurred in the current and consecutive gait cycles, respectively. By comparing the ankle joint moment calculated from ID, the averaged peak net PF moment across all walking gait cycles within each walking trial mono-tonically increased with the increase of walking speeds on each participant, indicating more power was needed for faster walking speed. The continuous results of neuromuscular features throughout the recorded walking duration were segmented as a percent of stance cycle from 0 to 100%, which are shown in FIG. 38. The solid lines and light shadowed areas report the mean and one SD values of the processed sEMG signals and US imaging-derived MT signals from the LGS and SOL muscles on the right leg during multiple stance phase cycles at each walking speed on Sub01, where 0% and 100% represent the time instants when the heel-strike and toe-off occurred in the same gait cycle, respectively. The upper two rows present the LGS and SOL MT changes during the stance phase, while the lower two rows present the muscle's low-pass filtered sEMG changes. The results show small variations of MT and sEMG for both LGS and SOL muscles at heel-strike across all walking speeds, but relatively high variations of sEMG for both LGS and SOL muscles at toe-off, where the sEMG signals increase with increased walking speed. For all five walking speeds, MT of LGS or SOL muscle is almost identical at heel-strike and toe-off, however, the processed sEMG signals of LGS or SOL muscle show higher value at toe-off than at heel-strike. By comparing the shadowed areas of the same feature across speeds, it is observed that features' deviations are higher at a slower speed, like 0.50 m/s, than those at higher speeds. This implies that keeping a steady muscle contraction pattern at a slower speed is more difficult than at a higher speed.

Results of HNM Calibration and Net PF Moment Prediction

In the HNM calibration procedures, one essential input component is the muscle activation levels of both LGS and SOL muscles, either only based on sEMG signals, US imaging-derived MT signals, or data fusion between them. The representative demonstration of three types of muscle activation levels of both LGS and SOL muscles during the walking stance phase at 0.75 m/s on Participant Sub03 are shown in FIG. 3 9. The left and right column subplots represent the time sequence points of muscle activation levels that are used in the model calibration and prediction procedures. It is observed that the data fusion could balance the muscle activation levels from both sEMG signals and MT signals and further compensate for the activation level drift from only MT signals, which is potentially beneficial for the accuracy improvement of the net plantarflexion moment prediction. FIG. 40A-E presents the representative results of HNMs calibrations on Sub05 with data collected from each individual walking speed, where each solid centered line and the shadowed area represent the mean and one SD values of the measured and calibrated net ankle joint PF moment, and each curve is composed of 10 stance cycles at each walking speed. For this participant, the mean calibration RMSE values are 8.70 N·m, 9.10 N·m, and 7.90 N·m by using sEMG-, US imaging-, and sEMG-US imaging-driven HNMs under walking speed of 0.50 m/s, respectively. Results from other walking speeds also showed that the sEMG-US imaging-driven HNM could effectively reduce the calibration RMSE under either single-speed modes or inter-speed mode. Based on the observation from FIG. 40A-E, it appears that the relative error may be inflated during specific areas of the stance cycles. The current outcomes (i.e., N-RMSE, BM-RMSE, and $R^2$ values) may not be directly sensitive to those specific areas, because the three evaluation metrics report an averaged performance across the entire stance cycle. This limitation of the current outcome metrics can be addressed in future work by identifying systematic changes in the prediction accuracy through-out the stance phase cycle rather than across the entire cycle. Overall, the calibration RMSE/R2 values by using the sEMG-US imaging-driven HNM are lower/higher than those by using the sEMG-driven and US imaging-driven HNMs, respectively, for both single-speed modes and inter-speed mode on all participants. Additionally, 97.5% of R2 values are higher than 0.80, which indicates a strong linear correlation between the calibrated and ID-calculated net PF moment values.

In contrast with mechanical signals that are used for estimating human limb motion intention, embodiments of the present disclosure relate to non-invasive surface electromyography (sEMG) signals in human-robotic systems. However, noise interference, crosstalk from adjacent muscle groups, and an inability to measure deeper muscle tissues are disadvantageous to sEMG's reliable use. In accordance with the present disclosure, a fusion between sEMG and in vivo ultrasound (US) imaging will result in more accurate detection of ankle movement intention.

Nine young able-bodied participants were included to volitionally perform isometric plantarflexion tasks with different fixed-end ankle postures, while the sEMG and US imaging data of plantarflexors were synchronously collected. Three dominant feature sets were created, sole sEMG feature set, sole US feature set, and sEMG-US feature fusion set, to calibrate and validate a support vector machine regression model (SVR) and a feedforward neural network model (FFNN) with labeled net moment measurements. The results showed that, compared to the sole sEMG feature set, the sEMG-US fusion set reduced the average net moment prediction error by 35.7% ($p<0.05$), when using SVR, and by 21.5% ($p<0.05$), when using FFNN. In SVR, the sole US feature set reduced the prediction error by 24.9% ($p<0.05$) when compared to the sole sEMG feature set. In FFNN, the sEMG-US fusion set reduced the prediction error by 28.2% ($p<0.05$) when compared to the sole US feature set.

These findings indicate that the combination of sEMG signals and US imaging is a superior sensing modality for predicting human plantarflexion intention and can enable future clinical rehabilitation devices.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system, comprising:
an ultrasound transducer; and
a controller comprising a processor and memory, the memory having computer-executable instructions stored thereon that, when executed by the processor, cause the processor to:
receive an ultrasound imaging signal associated with a subject's muscular activity from the ultrasound transducer;
process the ultrasound imaging signal to determine one or more muscle state parameters comprising at least one of echogenicity, muscle pennation angle, muscle fascicle length, muscle thickness, muscle strength, and muscle fatigue;
generate a feedback signal to suppress tremors based on the determined one or more muscle state parameters, and
control a device interfacing with the subject based on the feedback signal.

2. The system of claim 1, further comprising a sensor configured to measure the subject's muscular activity, wherein the memory has further computer-executable instructions stored thereon that, when executed by the processor, cause the processor to:
receive a sensor signal from the sensor;
combine data from the ultrasound imaging signal and the sensor signal to create a fused signal; and
process the fused signal to obtain the feedback signal.

3. The system of claim 2, wherein the sensor is at least one of an accelerometer, a gyroscope, a magnetometer, an inertial measurement unit (IMU), a force sensor, a strain sensor, or an electromyography (EMG) sensor.

4. The system of claim 1, further comprising the device.

5. The system of claim 4, wherein the device comprises a stimulus generator and at least two electrodes, wherein the at least two electrodes are operably coupled to the stimulus generator.

6. The system of claim 5, wherein controlling the device based on the feedback signal comprises adjusting a characteristic of stimulation delivered to the subject by the stimulus generator.

7. The system of claim 4, wherein the device comprises a powered joint exoskeleton.

8. The system of claim 7, wherein controlling the device based on the feedback signal comprises adjusting a torque assistance of the powered joint exoskeleton.

9. The system of claim 8, wherein controlling the device based on the feedback signal comprises stopping stimulation based on the at least one muscle state parameter.

10. The system of claim 1, wherein the subject's muscular activity is a voluntary or involuntary muscle contraction.

11. The system of claim 10, wherein the voluntary or involuntary muscle contraction is ankle dorsiflexion or plantarflexion.

12. The system of claim 10, wherein the voluntary or involuntary muscle contraction is a tremor, and wherein the tremor is detected by quantifying muscle contractility based, at least in part, on a tremor frequency measured via two or more electrodes.

13. The system of claim 1, wherein the subject's muscular activity is a stimulation-induced muscle contraction.

14. The system of claim 1, wherein the controller is configured for real-time control of the device based on the feedback signal.

15. The system of claim 1, further comprising:
processing the ultrasound imaging signal or controlling the device using a machine learning technique.

16. A system, comprising:
an ultrasound transducer;
a plurality of kinematic sensors;
a stimulation device comprising a stimulus generator and at least two electrodes, wherein the at least two electrodes are operably coupled to the stimulus generator; and
a controller comprising a processor and memory, the memory having computer-executable instructions stored thereon that, when executed by the processor, cause the processor to:
receive an ultrasound imaging signal associated with a subject's muscular activity from the ultrasound transducer;
process the ultrasound imaging signal to obtain a first feedback signal by determining one or more muscle state parameters comprising at least one of echogenicity, muscle pennation angle, muscle fascicle length, muscle thickness, muscle strength, and muscle fatigue;

process respective kinematic sensor signals from the kinematic sensors to obtain a second feedback signal; and control the stimulation device to suppress tremors based on the first and second feedback signals.

17. The system of claim 16, wherein the kinematic sensors comprise one or more of a ground force sensor, an inertial measurement unit, or a joint angle encoder.

18. The system of claim 16, wherein processing the ultrasound imaging signal comprises sampling the ultrasound imaging signal at a first sampling rate, wherein processing the respective kinematic signals comprises sampling the respective kinematic sensor signals at a second sampling rate, and wherein the first sampling rate is less than the second sampling rate.

19. The system of claim 18, wherein the controller comprises a sampled-data based observer (SDO) module configured to sample the ultrasound imaging signal at the first sampling rate.

20. The system of claim 16, wherein the controller comprises a dynamic surface control-delay compensation (DSC-DC) module configured to account for the subject's muscle activation dynamics and electromechanical delay.

21. The system of claim 16, wherein processing the ultrasound imaging signal comprises determining a feature associated with a muscle.

22. The system of claim 16, wherein the subject's muscular activity is a stimulation-induced muscle contraction.

23. The system of claim 22, wherein the stimulation-induced muscle contraction is ankle dorsiflexion.

24. The system of claim 16, wherein the controller is configured for real-time control of the stimulation device based on the first and second feedback signals.

25. The system of claim 24, wherein the controller is configured to stop the stimulation device based on detected echogenicity or muscle strength.

26. A system, comprising:

an ultrasound transducer;

a sensor configured to measure a subject's muscular activity;

a powered joint exoskeleton; and a controller comprising a processor and memory, the memory having computer-executable instructions stored thereon that, when executed by the processor, cause the processor to:

receive an ultrasound imaging signal associated with the subject's muscular activity from the ultrasound transducer;

receive a sensor signal from the sensor;

combine data from the ultrasound imaging signal and the sensor signal to create a fused signal;

analyze the fused signal to determine one or more muscle state parameters comprising at least one of echogenicity, muscle pennation angle, muscle fascicle length, muscle thickness, muscle strength, and muscle fatigue;

predict a joint torque based on the determined one or more muscle state parameters; and control a torque assistance of the powered joint exoskeleton to suppress tremors based on the predicted joint torque.

27. The system of claim 26, wherein the sensor is a surface electromyography (sEMG) sensor.

28. The system of claim 26, wherein combining data from the ultrasound imaging signal and the sensor signal comprises sampling the ultrasound imaging signal at a first sampling rate and sampling the sensor signal at a second sampling rate, and wherein the first sampling rate is less than the second sampling rate.

29. The system of claim 28, wherein the controller comprises a multi-rate observer module configured to sample the ultrasound imaging signal and the sensor signal at the first and second sampling rates, respectively.

30. The system of claim 26, wherein the controller comprises a neuromuscular model module configured to predict the joint torque based on the subject's detected muscular activity.

31. The system of claim 26, wherein the controller comprises an adaptive impedance control (AIC) module configured to control the torque assistance of the powered joint exoskeleton based on the predicted joint torque.

32. The system of claim 26, wherein the subject's muscular activity is ankle plantarflexion.

33. The system of claim 26, wherein the powered joint exoskeleton comprises a frame, an actuation unit, an end-effector unit, and a cable, and wherein the cable operably couples the actuation unit and the end-effector unit.

34. The system of claim 26, wherein the controller is configured for real-time control of the torque assistance of the powered joint exoskeleton based on the predicted joint torque.

35. The system of claim 26, wherein the controller is configured to stop torque assistance of the powered joint exoskeleton based on a detected echogenicity or muscle strength.

36. A system, comprising:

an ultrasound transducer;

a stimulation device comprising a stimulus generator and at least two electrodes, wherein the at least two electrodes are operably coupled to the stimulus generator; and a controller comprising a processor and memory, the memory having computer-executable instructions stored thereon that, when executed by the processor, cause the processor to:

receive an ultrasound imaging signal associated with a subject's muscular activity from the ultrasound transducer;

process the ultrasound imaging signal to quantify the subject's muscular activity; and control the stimulation device based on based on the subject's quantified muscular activity to suppress a tremor, and wherein the tremor is detected by quantifying muscle contractility based, at least in part, on a tremor frequency measured via the at least two electrodes.

37. The system of claim 36, wherein processing the ultrasound imaging signal to quantify the subject's muscular activity comprises determining a frequency of muscle contraction.

38. The system of claim 36, wherein controlling the stimulation device based on based on the subject's detected muscular activity to suppress the tremor comprises selecting a characteristic of stimulation delivered to the subject by the stimulus generator.

39. The system of claim 36, wherein the memory has further computer-executable instructions stored thereon that, when executed by the processor, cause the processor to differentiate between involuntary tremor and volitional muscle contraction.

40. The system of claim 36, wherein the controller is configured for real-time control of the stimulation device based on based on the subject's detected muscular activity to suppress the tremor.

* * * * *